US009186171B2

(12) United States Patent
Esarey et al.

(10) Patent No.: US 9,186,171 B2
(45) Date of Patent: Nov. 17, 2015

(54) POWER OPERATED DEBRIDEMENT TOOL WITH DISK KNIFE BLADE

(71) Applicants: Bernard J. Esarey, Avon, OH (US); Jeffrey A. Whited, Amherst, OH (US)

(72) Inventors: Bernard J. Esarey, Avon, OH (US); Jeffrey A. Whited, Amherst, OH (US)

(73) Assignee: Exsurco Medical, Inc., Birmingham, OH (US)

( * ) Notice: Subject to any disclaimer, the term of this patent is extended or adjusted under 35 U.S.C. 154(b) by 234 days.

(21) Appl. No.: 13/786,996

(22) Filed: Mar. 6, 2013

(65) Prior Publication Data

US 2014/0074119 A1 Mar. 13, 2014

Related U.S. Application Data

(63) Continuation-in-part of application No. 13/606,836, filed on Sep. 7, 2012.

(51) Int. Cl.
*A61B 17/322* (2006.01)
*A22B 5/16* (2006.01)
*A61B 19/00* (2006.01)

(52) U.S. Cl.
CPC .............. *A61B 17/322* (2013.01); *A22B 5/16* (2013.01); *A61B 2019/303* (2013.01)

(58) Field of Classification Search
CPC ............. A61B 17/32; A61B 17/32002; A61B 17/3205; A61B 17/320758; A61B 17/3209; A61B 17/32093; A61B 17/322; A61B 2017/00761; A61B 2017/3225; A61B 2019/303; A61B 2019/306; A61F 9/00736; A61F 9/00754; A61F 9/00763; A61F 9/013; A61F 9/0133; A22B 5/16; A22B 5/165; A01D 34/16; A01D 34/90; A01D 34/4161; A01D 34/4163; B26B 25/002; B25F 5/003
See application file for complete search history.

(56) References Cited

U.S. PATENT DOCUMENTS 324,435 A * 8/1885 Underwood .................... 30/139
941,829 A * 11/1909 Wallader et al. ................ 30/276
(Continued)

OTHER PUBLICATIONS

International Search Report dated Dec. 12, 2013 and Written Opinion of the International Searching Authority dated Dec. 12, 2013 for PCT International Application No. PCT/US2013/058133, filed Sep. 5, 2013. PCT International Application No. PCT/US2013/058133 corresponds to and claims priority from U.S. Appl. No. 13/606,836, filed Sep. 7, 2012. The present application is a continuation-in-part of and claims priority from U.S. Appl. No. 13/606,836. (10 pages) (Exhibit A).

(Continued)

*Primary Examiner* — Katherine Rodjom
*Assistant Examiner* — Christian Knauss
(74) *Attorney, Agent, or Firm* — Tarolli, Sundheim, Covell & Tummino LLP

(57) ABSTRACT

A hand-held, power operated debridement tool (2000) includes a rotary disk knife blade (2300) with a cutting edge (2360) on an outer peripheral edge (2362) of the knife blade, the cutting edge defining a cutting plane (CP) of the disk knife blade. The debridement tool further includes an annular skin guide (2700) including an outer wall (2716) defining a skin contact surface (2720) disposed above the cutting plane (CP) of the disk knife blade and positioned radially inwardly of the disk knife blade cutting edge to receive and direct an excised layer of skin tissue (EST) cut by the disk knife blade upwardly away from the blade cutting edge. The debridement tool additionally includes an axially adjustable depth gauge (2620) including a depth gauge plate (2622) disposed above the cutting plane of the disk knife blade and positioned radially outwardly of the cutting edge of the disk knife blade.

28 Claims, 33 Drawing Sheets

(56) References Cited

U.S. PATENT DOCUMENTS

| | | | |
|---|---|---|---|
| 1,379,153 A * | 5/1921 | Young | 30/276 |
| 2,263,431 A * | 11/1941 | White | 56/13.4 |
| 2,540,462 A * | 2/1951 | Smith | 606/132 |
| 2,582,511 A * | 1/1952 | Stryker | 606/132 |
| 2,730,100 A * | 1/1956 | Hood | 606/132 |
| 2,730,102 A * | 1/1956 | Hood | 606/132 |
| 3,126,889 A * | 3/1964 | Blumenfeld | 606/180 |
| 3,197,808 A | 8/1965 | Mears | |
| 3,269,010 A | 8/1966 | Bettcher | |
| 3,461,557 A | 8/1969 | Behring | |
| 3,670,734 A * | 6/1972 | Hardy, Jr. | 606/132 |
| 3,688,403 A | 9/1972 | Bettcher | |
| 4,142,291 A | 3/1979 | Bettcher | |
| 4,170,063 A | 10/1979 | Bettcher | |
| 4,198,750 A | 4/1980 | Bettcher | |
| 4,236,531 A | 12/1980 | McCullough | |
| 4,363,170 A | 12/1982 | McCullough | |
| 4,439,924 A | 4/1984 | Bettcher | |
| 4,492,027 A | 1/1985 | Bettcher | |
| 4,494,311 A | 1/1985 | McCullough | |
| 4,516,323 A | 5/1985 | Bettcher et al. | |
| 4,575,937 A | 3/1986 | McCullough | |
| 4,575,938 A | 3/1986 | McCullough | |
| 4,590,676 A | 5/1986 | Bettcher | |
| 4,854,046 A | 8/1989 | Decker et al. | |
| 4,858,321 A | 8/1989 | McCullough | |
| 5,163,288 A * | 11/1992 | Doley | 606/133 |
| 5,230,154 A | 7/1993 | Decker et al. | |
| 5,522,142 A * | 6/1996 | Whited | 30/276 |
| 5,529,532 A | 6/1996 | Desrosiers | |
| 5,632,090 A | 5/1997 | Smith | |
| 5,664,332 A | 9/1997 | Whited et al. | |
| 5,692,307 A | 12/1997 | Whited et al. | |
| 5,761,817 A | 6/1998 | Whited et al. | |
| 5,940,972 A | 8/1999 | Baris et al. | |
| 6,327,783 B1 * | 12/2001 | Ming | 30/292 |
| 6,460,254 B1 * | 10/2002 | Mori et al. | 30/286 |
| 6,604,288 B2 | 8/2003 | Whited et al. | |
| 6,615,494 B2 | 9/2003 | Long et al. | |
| 6,665,943 B1 * | 12/2003 | Sloane et al. | 30/276 |
| 6,694,649 B2 | 2/2004 | Whited et al. | |
| 6,751,872 B1 | 6/2004 | Whited et al. | |
| 6,769,184 B1 | 8/2004 | Whited | |
| 6,880,249 B2 | 4/2005 | Long et al. | |
| 6,978,548 B2 | 12/2005 | Whited et al. | |
| 8,037,611 B2 | 10/2011 | Levsen | |
| 8,661,692 B2 | 3/2014 | Whited et al. | |
| 8,739,416 B2 | 6/2014 | Mascari et al. | |
| 8,752,299 B2 | 6/2014 | Rosu et al. | |
| 8,756,819 B2 | 6/2014 | Whited et al. | |
| 8,806,761 B2 | 8/2014 | Whited et al. | |
| 2002/0096027 A1 | 7/2002 | Whited et al. | |
| 2003/0070301 A1 | 4/2003 | Hermann et al. | |
| 2003/0084576 A1 | 5/2003 | Whited et al. | |
| 2003/0131482 A1 | 7/2003 | Long et al. | |
| 2003/0196333 A1 | 10/2003 | Whited | |
| 2004/0187316 A1 | 9/2004 | Whited et al. | |
| 2005/0126015 A1 | 6/2005 | Whited | |
| 2005/0178009 A1 | 8/2005 | Whited | |
| 2005/0217119 A1 | 10/2005 | Rapp | |
| 2006/0037200 A1 | 2/2006 | Rosu et al. | |
| 2006/0137193 A1 | 6/2006 | Whited | |
| 2007/0283573 A1 | 12/2007 | Levsen | |
| 2007/0283574 A1 | 12/2007 | Levsen | |
| 2008/0022537 A1 * | 1/2008 | Clarke et al. | 30/390 |
| 2008/0098605 A1 | 5/2008 | Whited et al. | |
| 2008/0168667 A1 * | 7/2008 | Spinato | 30/391 |
| 2009/0138027 A1 * | 5/2009 | Lucas et al. | 606/132 |
| 2009/0157095 A1 * | 6/2009 | Barker et al. | 606/132 |
| 2011/0185580 A1 | 8/2011 | Whited | |
| 2011/0247220 A1 | 10/2011 | Whited et al. | |
| 2013/0025134 A1 | 1/2013 | Mascari et al. | |
| 2013/0025139 A1 | 1/2013 | Whited et al. | |
| 2013/0174424 A1 | 7/2013 | Whited et al. | |

OTHER PUBLICATIONS

International Search Report dated Dec. 12, 2013 and Written Opinion of the International Searching Authority dated Dec. 12, 2013 for PCT International Application No. PCT/US2013/058142, filed Sep. 5, 2013. PCT International Application No. PCT/US2013/058142 corresponds to and claims priority from U.S. Appl. No. 13/842,224, filed Mar. 15, 2013 and from U.S. Appl. No. 13/606,836, filed Sep. 7, 2012. The present application is a continuation-in-part of and claims priority from U.S. Appl. No. 13/606,836. (9 pages) (Exhibit B).

Oct. 3, 2011 Decision and Opinion of the United States Court of Appeals for the Federal Circuit (Appeal No. 2011-1038,—1046) regarding the case styled *Bettcher Industries, Inc.* v. *Bunzi USA, Inc. and Bunzl Processor Distribution, LLC*, Case No. 3:08 CV 2423, U.S. District Court for the Northern District of Ohio, Judge Zouhary. The Decision and Opinion relates to U.S. Patent No. 7,000,325, owned by the assignee of the present application. (47 pages) (Exhibit C).

Catalog entitled "Ball Bearing Cages", Publication No. WLK 100 E, Publication Date—Sep. 2004, Published by International Customized Bearings. (34 pages) (Exhibit D).

Operators Manual for Integra Model C Air Dermatome Manufactured by Integra LifeSciences Corporation, Copyright 2009, Cincinnati, OH (82 pages) (Exhibit E).

Instruction Manual for Zimmer™ Air Dermatome, Manufactured by Zimmer Surgical, Inc., Dover, OH, Copyright 1992 (127 pages) (Exhibit F).

Operators Manual, Integra TM, Model SB Dermatome, Manufactured by Integra LifeSciences Corporation, Plainsboro, New Jersey, Copyright 2005 (6 pages) (Exhibit G).

Informational Brochure for Humeca Dermatome Blades, Manufactured by Humeca BV, Enschede, The Netherlands, publication date Oct. 2008 (1 page) (Exhibit H).

Image of Super Gyros Knife-Metal, manufactured by Optimal Automatics, Inc., Chicago, IL. Advertisement [online]. Retrieved from the Internet: URL:http://www.autodoner.com/autodoner/products/gyro-knife/super-gyros-knife-metal.aspx. The Super Gyros Knife depicted in the Internet printout is prior art to the present application. (3 pages) (Exhibit I).

14 Photographs of Super Gyros Knife, Model P, Manufactured by Optimal Automatics, Inc., Chicago, IL. The Super Gyros Knife depicted in the 6 photos is prior art to the present application (6 pages) (Exhibit J).

3 Photographs of Power Operated Gyros Knife, Manufacturer, Unknown. The Power Operated Gyros Knife depicted in the 3 photographs is prior art to present application (3 pages) (Exhibit K).

Image of Super Gyros Knife-Plastic, manufactured by Optimal Automatics, Inc., Chicago, IL. Advertisement [online]. Retrieved from the Internet: URL:http://www.autodoner.com/autodoner/products/gyro-knife/super-gyros-knife-plastic.aspx. The Super Gyros Knife depicted in the Internet printout is prior art to the present application. (4 pages) (Exhibit L).

* cited by examiner

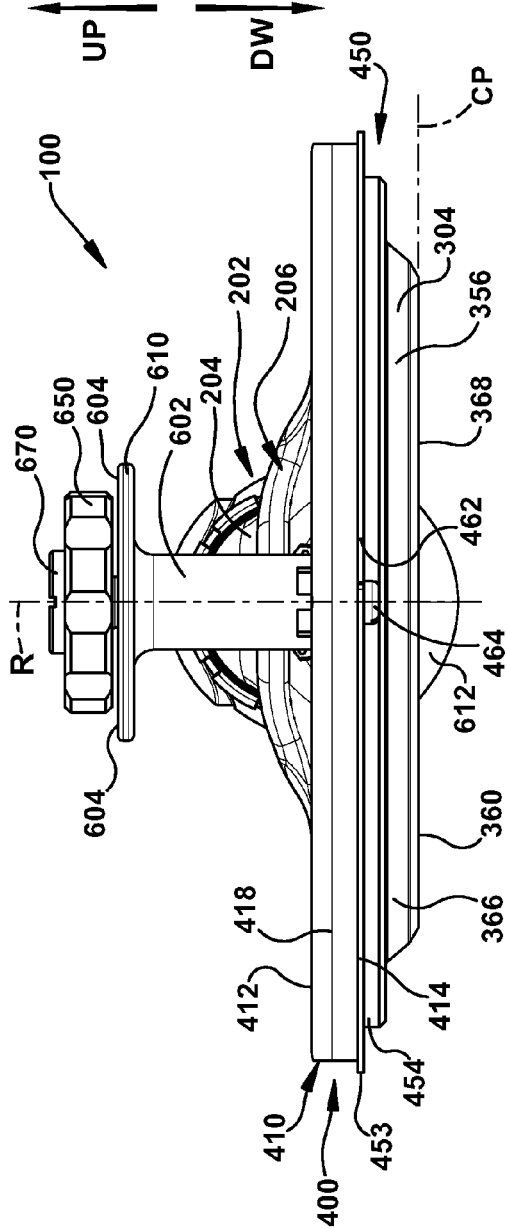
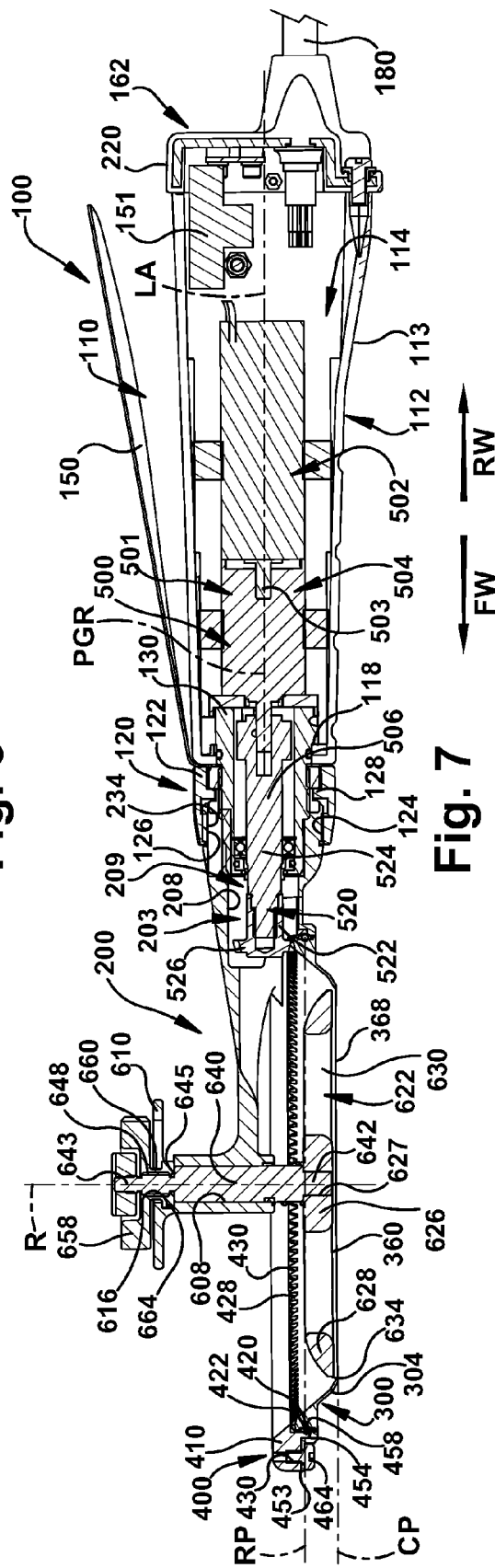

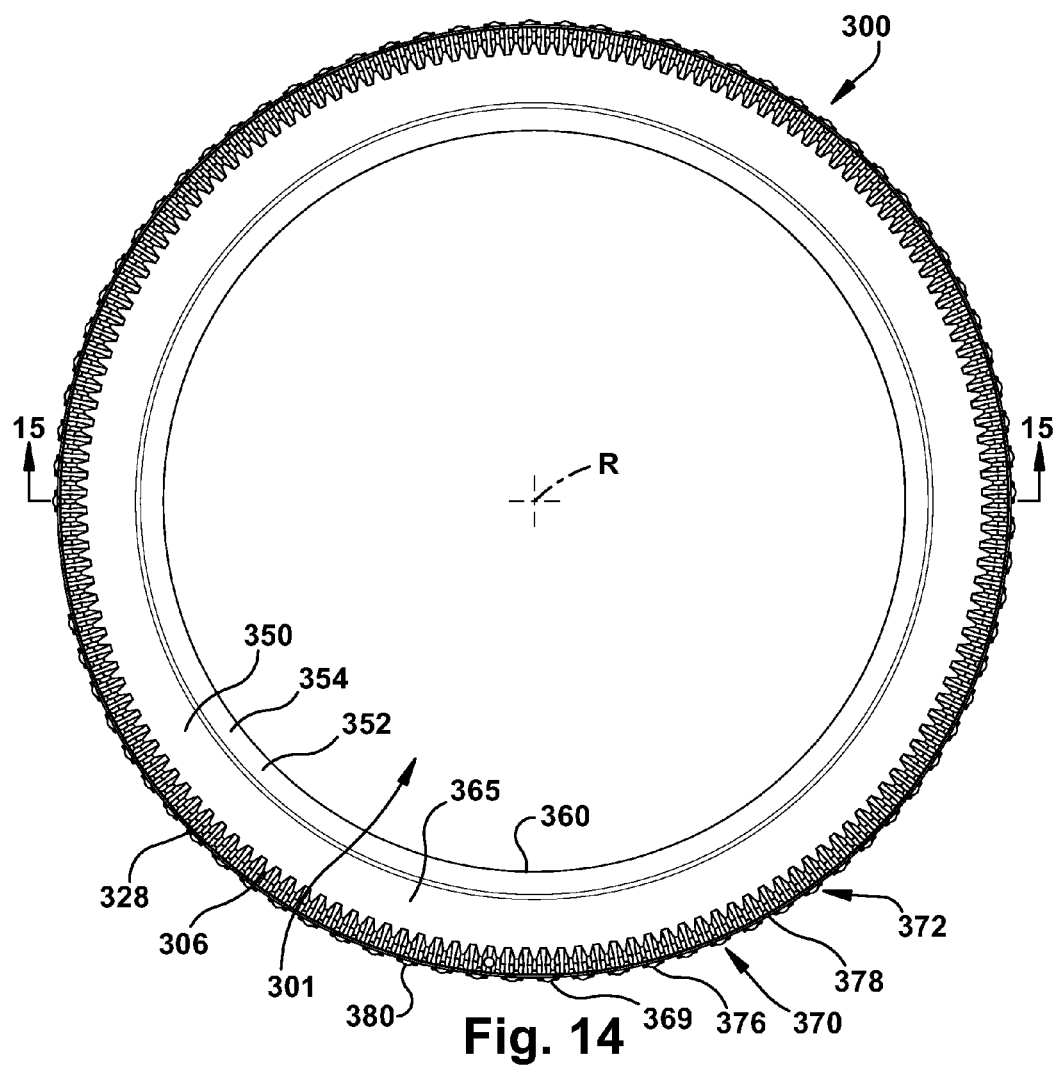
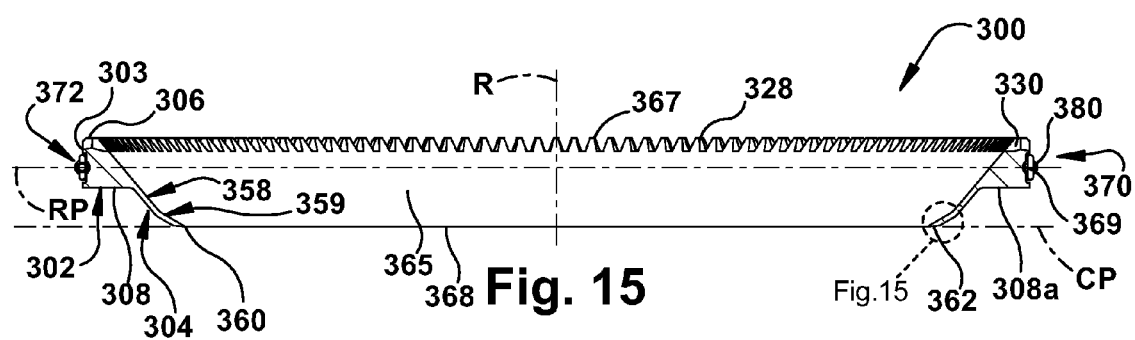

POWER OPERATED DEBRIDEMENT TOOL WITH DISK KNIFE BLADE

CROSS-REFERENCE TO RELATED APPLICATION

The present application is a continuation-in-part application of co-pending U.S. application Ser. No. 13/606,836, filed Sep. 7, 2012 and entitled POWER OPERATED DERMATOME WITH ROTARY KNIFE BLADE. The present application claims priority from above-identified application Ser. No. 13/606,836, which is incorporated herein in its entirety by reference, for all purposes.

TECHNICAL FIELD

The present disclosure relates to a hand-held, power operated debridement tool including a rotary disk knife blade with a cutting edge on an outer peripheral edge of the knife blade, the cutting edge defining a cutting plane of the disk knife blade, an axially adjustable depth gauge including a depth gauge plate disposed above the cutting plane of the disk knife blade and positioned radially outwardly of the cutting edge of the disk knife blade, and an annular skin guide including a skin contact outer surface disposed above the cutting plane of the disk knife blade and positioned radially inwardly of the disk knife blade cutting edge to receive and direct a layer of skin tissue cut by the disk knife blade upwardly away from the blade cutting edge.

BACKGROUND

Dermatomes are hand-held surgical instruments used by a physician or medical professional (hereinafter operator) for cutting thin layers or sections of skin tissue. Dermatomes are used in hospitals and other medical facilities for excising or removal of skin tissue from patients in connection with various medical procedures including split-thickness and full-thickness skin grafting, skin debriding (e.g., removal of burned skin tissue), tumor/lesion removal, and breast reduction, among other procedures. Dermatomes are also used in to remove skin tissue from deceased human or animal donors for skin grafting purposes.

Prior dermatomes included both manual operated and power operated dermatomes. Manual dermatomes typically included a fixed blade and a handle projecting from the blade. Manual dermatomes were often found tedious to use and prone to operator fatigue, especially when large sections of skin tissue needed to be removed, requiring multiple sections of skin tissue to be removed. For example, a deceased human donor may provide from 6-9 square feet of recoverable skin tissue.

It is generally desired that an excised skin section be of uniform or consistent thickness along the longitudinal extent of the skin section and across the width of the skin section. The thickness of an excised skin section is dependent on the depth of cut of the dermatome cutting blade. Use of manual dermatomes often resulted in excised skin sections of varying thickness and having irregular edges. The uniformity of the depth of cut was largely dependent on the skill of the operator. While limited numbers of manual dermatomes continue to be used, power operated dermatomes are favored in procedures where large sections of skin tissue need to be removed in an efficient manner and/or operator fatigue is an issue.

Prior power operated dermatomes typically included a reciprocating cutting blade disposed at a front or leading edge of the dermatome with a guard or depth gauge to allow the operator to set a depth of cut of the dermatome to remove a desired thickness of skin tissue. The blade was typically disposed orthogonally to a rearward extending handle or hand piece of the dermatome. Because the cutting direction of the blade of prior power operated dermatomes was forward facing, such dermatome configurations required the operator to move the dermatome in a direction generally away from the operator's body to excise or cut a section of skin tissue. This direction of movement of the operator's hand and the dermatome away from the operator's body is less natural and less precise that a direction of movement of the operator's hand and dermatome toward the operator. Moreover, in moving the dermatome away from the operator's body, the position of the dermatome tends to block the area of the skin tissue being excised from the view of the operator. This is especially problematic where the tissue to be removed is adjacent to, for example, a raised or bony prominence of the body that must be carefully navigated around with the cutting edge of the dermatome cutting blade.

Additionally, with prior power operated dermatomes, in order to cut a skin tissue section with a desired, consistent depth of cut, the angle of cut, the speed of the dermatome along the skin, and the pressure applied to the dermatome had to be carefully controlled by the operator. The angle of cut of the dermatome refers to an acute angle between the dermatome cutting blade and the skin tissue being removed or excised. If the angle of cut of the dermatome is too shallow, the desired depth of cut will not be achieved. If the angle of cut of the dermatome is too steep, gouging or trenching of the excised skin tissue will occur. Further, if the angle of cut is changed as the power operated dermatome is moved along the skin tissue, the depth of cut will vary along a longitudinal extent of the excised section of skin tissue.

The speed or rate of forward movement of prior power operated dermatomes also had to be carefully controlled by the operator. If the speed of the dermatome was too fast or too slow, the depth of cut of the excised skin section may be greater or less than the desired depth of cut as set by the operator using the dermatome depth gauge.

The operator using a typical prior power operated dermatome also was required to apply considerable pressure to the dermatome to insure that the entire extent or length of the cutting edge of the reciprocating blade remained in contact with the skin tissue. The pressure applied by the operator to the dermatome needed to remain constant. If the pressure applied by the operator to the dermatome was too high or too low during a cutting operation, the depth of cut could change and the excised skin section would have portions that were of greater or less depth than the desired depth of cut as set with the dermatome depth gauge. If the pressure applied by the operator to the dermatome was too low, the excised skin tissue may be too thin resulting in holes in the excised skin tissue and/or chattered edges.

Uniformity in the depth of cut of excised skin sections is especially important in split thickness skin grafts where it desired to remove only the outer epidermis and a portion of the dermis. Desired skin tissue thickness in a thin-type split-thickness skin graft is on the order of 0.127 to 0.304 mm. Thus, there is little margin for error where the desired skin thickness and depth of cut is very thin.

With prior dermatomes using a reciprocating blade, it was sometimes necessary for the operator to have an assistant provide counter-traction to flatten the skin surface in front of or behind the path of travel of the dermatome to allow the dermatome blade to make an initial cut. Adding an additional person to the procedure not only increases the cost of the procedure, but also increases the risk of infection and contamination due to the presence of another person in the operating or procedure room.

What is needed is a power operated dermatome wherein obtaining a desired, consistent thickness of an excised skin tissue section is less dependent on operator skill in maintaining a constant, desired angle of cut, speed and pressure on the dermatome. What is needed is a power operated dermatome that reduces operator fatigue when removing large sections of skin tissue. What is needed is a power operated dermatome that facilitates the removal of skin tissue in tight spaces and around boney prominences. What is needed is a power operated dermatome that facilitates improved control of the dermatome by the operator by moving the blade cutting edge along a path toward the operator, instead of moving the blade away from the operator. What is needed is a power operated dermatome that allows for improved visibility of the skin site being excised by the operator. What is needed is a power operated dermatome that facilitates removal of very thin layers of skin tissue and tangential excision of burn tissue. What is needed is a power operated dermatome that does not require an additional person involved in the procedure to provide counter-traction at the skin removal site to permit an initial cut to be made by the dermatome.

SUMMARY

In one aspect, the present disclosure relates to a head assembly for a power operated dermatome, the head assembly comprising: a frame body supporting a gear train, a blade housing assembly, an annular rotary knife blade supported for rotation about an axis of rotation by the blade housing assembly, the rotary knife blade including an inner wall defining an interior region of the rotary knife blade and having a cutting edge at one end of the rotary knife blade defining a cutting plane orthogonal to the axis of rotation of the rotary knife blade, and a depth gauge assembly including a depth gauge support and a depth gauge including a depth gauge plate supported by the depth gauge for axial movement along the axis of rotation of the rotary knife blade, the depth gauge plate extending into the interior region of the rotary knife blade and the depth gauge support attached to and extending from the frame body.

In another aspect, the present disclosure relates to a power operated dermatome comprising: an elongated handle assembly and a head assembly removably coupled to the handle assembly, the head assembly including a frame body supporting a gear train, a blade housing assembly, an annular rotary knife blade supported for rotation about an axis of rotation by the blade housing assembly, the rotary knife blade including an inner wall defining an interior region of the rotary knife blade and having a cutting edge at one end of the rotary knife blade defining a cutting plane orthogonal to the axis of rotation of the rotary knife blade, and a depth gauge assembly including a depth gauge support and a depth gauge including a depth gauge plate supported by the depth gauge for axial movement along the axis of rotation of the rotary knife blade, the depth gauge plate extending into the interior region of the rotary knife blade and the depth gauge support attached to and extending from the frame housing.

In another aspect, the present disclosure relates to a head assembly for a power operated debridement tool, the head assembly comprising: a frame body supporting a drive assembly of the power operated debridement tool; a disk knife blade coupled to the frame body and rotated by the drive assembly about an axis of rotation, the disk knife blade including a cutting edge on an outer peripheral edge of the disk knife blade defining a cutting plane of the disk knife blade that is orthogonal to the axis of rotation; and an annular skin guide including an upper end, an axially spaced apart lower end adjacent the disk knife blade, and an outer wall defining a skin contact surface extending between the upper and lower ends of the annular skin guide, the skin contact surface positioned above the cutting plane of the disk knife blade and radially inwardly of the disk knife blade cutting edge to receive and direct a layer of skin tissue cut by the disk knife blade upwardly away from the blade cutting edge, the skin contact surface being recessed radially inwardly in a direction proceeding toward the disk knife blade axis of rotation with respect to a line segment extending between a first outer edge of the skin contact surface adjacent the upper end of the annular skin guide and a second outer edge of the skin contact surface adjacent the lower end of the annular skin guide.

In another aspect, the present disclosure relates to a power operated debridement tool comprising: a frame body; a drive assembly supported by the frame body; a disk knife blade coupled to the frame body and rotated by the drive assembly about an axis of rotation, the disk knife blade including a cutting edge on an outer peripheral edge of the disk knife blade defining a cutting plane of the disk knife blade that is orthogonal to the axis of rotation; and an annular skin guide including an upper end, an axially spaced apart lower end adjacent the disk knife blade, and an outer wall defining a skin contact surface extending between the upper and lower ends of the annular skin guide, the skin contact surface positioned above the cutting plane of the disk knife blade and radially inwardly of the disk knife blade cutting edge to receive and direct a layer of skin tissue cut by the disk knife blade upwardly away from the blade cutting edge, the skin contact surface being recessed radially inwardly in a direction proceeding toward the disk knife blade axis of rotation with respect to a line segment extending between a first outer edge of the skin contact surface adjacent the upper end of the annular skin guide and a second outer edge of the skin contact surface adjacent the lower end of the annular skin guide.

BRIEF DESCRIPTION OF THE DRAWINGS

The foregoing and other features and advantages of the present disclosure will become apparent to one skilled in the art to which the present disclosure relates upon consideration of the following description of the invention with reference to the accompanying drawings, wherein like reference numerals, unless otherwise described refer to like parts throughout the drawings and in which:

FIG. 6 is a schematic front elevation view of the power operated dermatome of FIG. 1;

FIG. 7 is a schematic longitudinal section view of the power operated dermatome of FIG. 1, as viewed along a longitudinal axis LA of the handle assembly of the dermatome;

FIG. 14 is a schematic front elevation view of an exemplary embodiment of the rotary knife blade of the power operated dermatome of FIG. 1;

FIG. 15 is a schematic section view of the rotary knife of FIG. 14, as seen from a plane indicated by the line 15-15 in FIG. 14;

FIG. 17 is a schematic section view of the power operated dermatome of FIG. 1, as manipulated to make an initial incision or cut in skin tissue for a thin type, split thickness skin graft wherein a depth of a layer of skin tissue being excised from a patient or donor graft site is on the order of 0.005 in. to 0.012 in.;

FIG. 18 is a schematic view, partially in perspective and partially in section, of the power operated dermatome of FIG. 1, as manipulated to cut or excise a thin type, split thickness skin graft wherein a depth of a layer of skin tissue being excised from a patient or donor graft site is on the order of 0.005 in. to 0.012 in.;

FIG. 19 is a schematic view, partially in perspective and partially in section, of the power operated dermatome of FIG. 1, as manipulated to terminate an incision in a thin type, split thickness skin graft wherein a depth of a layer of skin tissue being excised from a patent or donor graft site is on the order of 0.005 in. to 0.012 in.;

FIG. 20 is a schematic view, partially in perspective and partially in section, of the power operated dermatome of FIG. 1, as used in a full thickness skin graft wherein a depth of a layer of skin tissue being excised from a donor graft site is on the order of 0.030 in. to 0.043 in.;

DETAILED DESCRIPTION

The present disclosure relates to a hand-held, power operated dermatome 100 for medical use in removing a layer of skin tissue SK (FIGS. 17-21) from a patient or donor in connection with various medical procedures including split-thickness and full-thickness skin grafting, skin debriding, e.g., removal of burned skin tissue, tumor/lesion removal, breast reduction, among other procedures, including removing a layer of skin tissue from a deceased human or animal donor for skin grafting/transplanting purposes. Advantageously, the dermatome 100 of the present disclosure includes an annular rotary knife blade 300 that is driven about a central axis of rotation R at a high rotational speed (on the order of 500-1,500 RPM) by a drive assembly 500 of the dermatome 100 and further includes a depth gauge assembly 600 to allow precise setting and adjustment of a depth of cut DOC of the dermatome 100.

Figure 18:
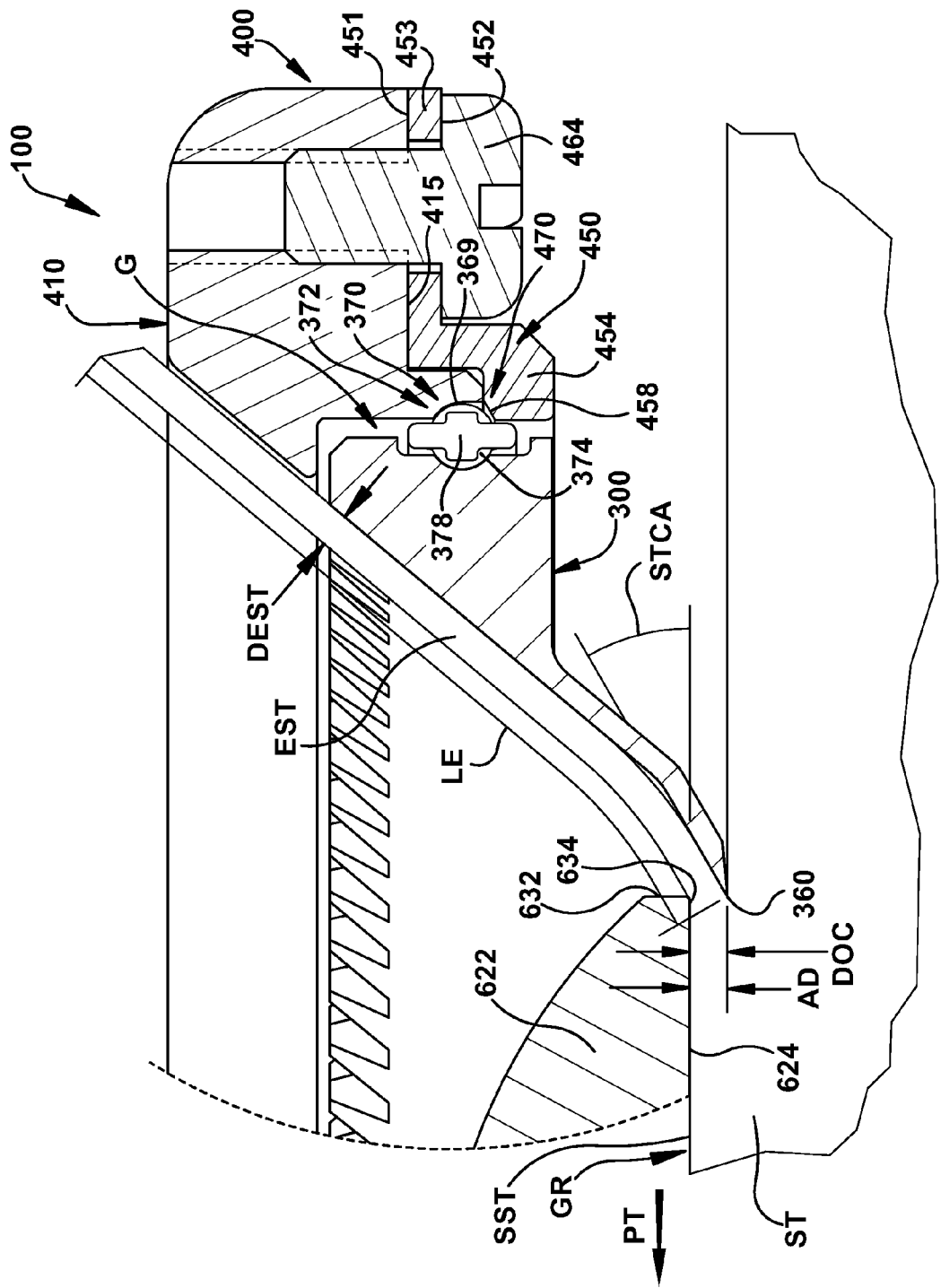
Figure 19:
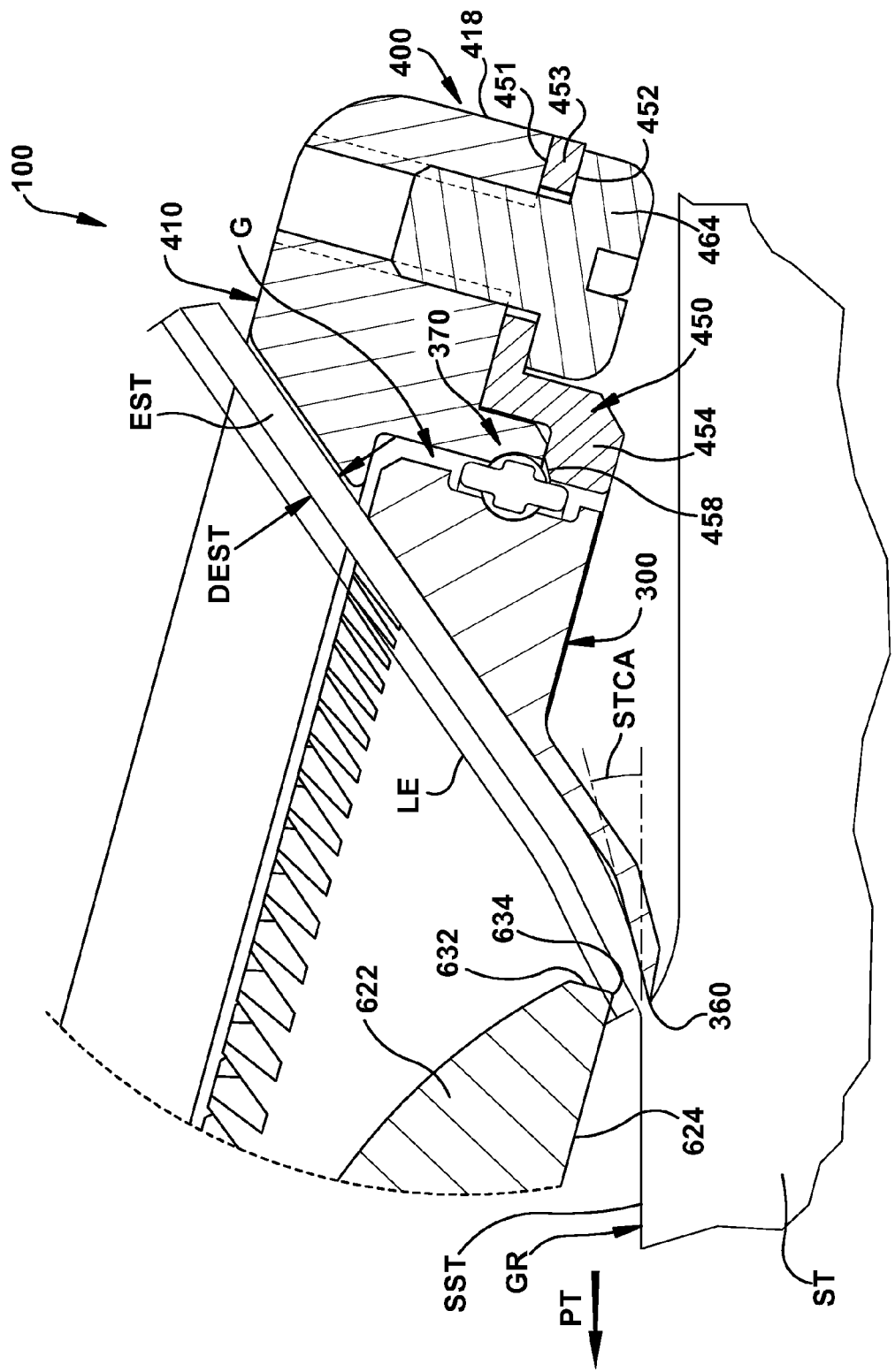
Figure 20:
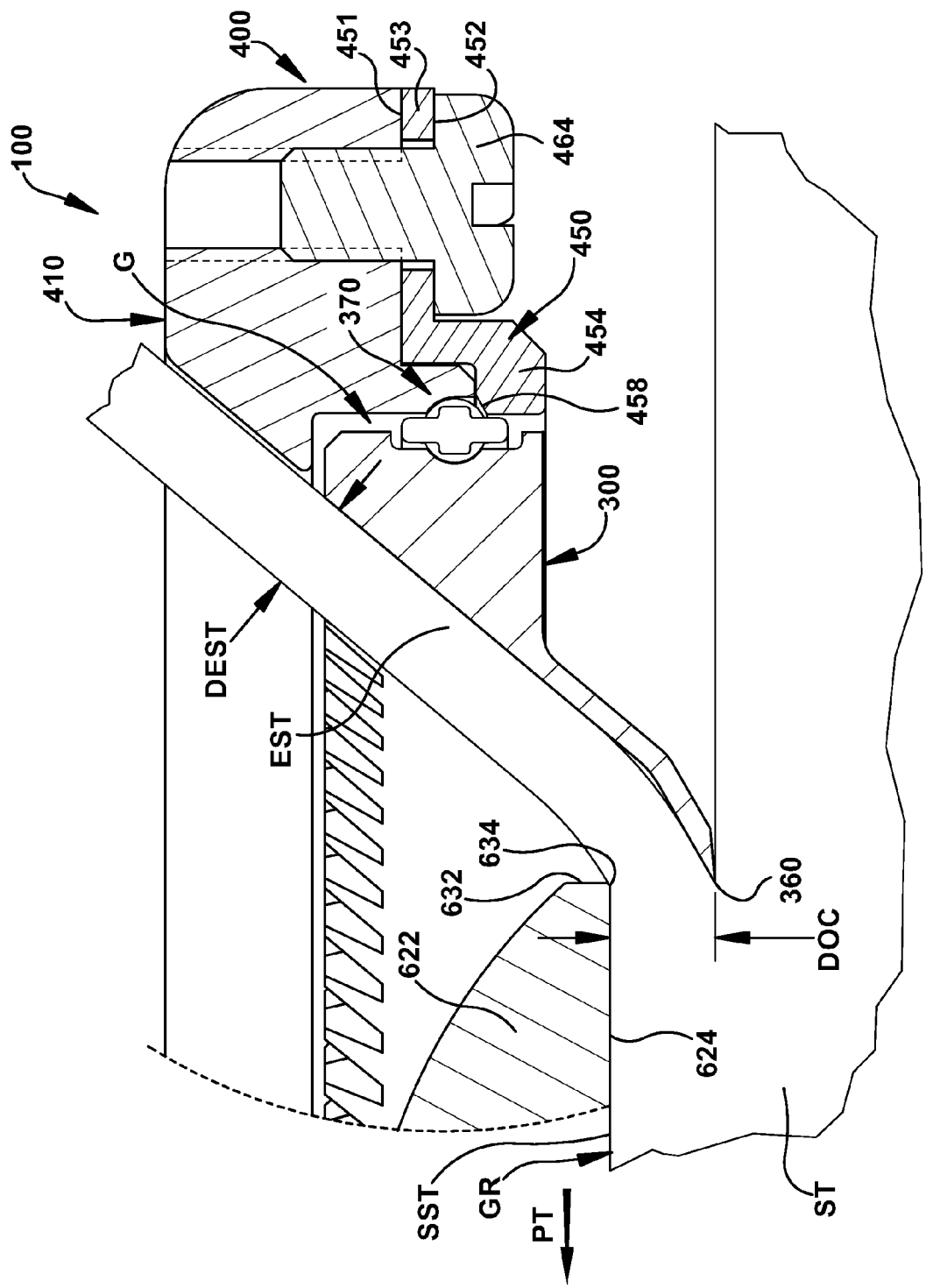

A cutting edge 360 of the rotary knife blade 300 cuts or excises an upper layer of skin tissue SK from a grafting region GR, resulting in an excised section or layer of skin tissue EST, as illustrated in FIGS. 18-20. In the dermatome 100 of the present disclosure, a cutting angle CA (FIGS. 7, 12, 13 and 16) of the blade section 304 adjacent the cutting edge 360 with respect to a cutting plane CP of the rotary knife blade 300 is relatively shallow. In one exemplary embodiment, the cutting angle CA is approximately 30° with respect to the cutting plane CP. The depth gauge assembly 600 of the dermatome 100 includes an axially adjustable depth gauge 620. The axially adjustable depth gauge 620 includes a depth gauge plate 622 and a depth gauge shaft 640 affixed to the depth gauge plate 622. The depth gauge 620 extends into a central opening 301 defined by the rotary knife blade 300.

An axial position of the depth gauge plate 622 with respect to the cutting edge 360 of the rotary knife blade 300 is determined by a rotation position of a depth adjustment knob 650 of the depth gauge assembly 600. The axial position of the gauge plate 622 of the depth gauge 620 with respect to the cutting edge 360 of the rotary knife blade 300 sets the depth of cut DOC of the dermatome 100. The depth of cut DOC of the dermatome 100 determines the depth or thickness of a section of skin tissue SK excised by the dermatome 100. The depth or thickness of an excised skin tissue section or layer is labeled as DEST in FIGS. 18-20. That is, the depth or thickness of an excised skin tissue section DEST of a patient or donor is determined by the depth of cut DOC of the dermatome 100, as precisely set by the operator of the dermatome 100 using the depth adjustment knob 650.

As compared to prior manual or power operated dermatomes, the high rotary speed of the rotary knife blade 300 of the dermatome 100 of the present disclosure, in combination with a shallow cutting angle CA of the knife blade 300 and configuration of the depth gauge assembly 600 and, specifically, the depth gauge plate 622, facilitate an operator's ability to cut or harvest an excised layer of skin tissue EST having a desired depth of cut of the excised tissue DEST that is more uniform and consistent along a longitudinal extend LE (FIGS. 18 and 19) of the excised skin tissue EST than what would be expected using a prior manual dermatome or a prior power operated dermatome. The dermatome 100 of the present disclosure advantageously provides for improved control and manipulation of the dermatome 100 by an operator, using one hand, as the dermatome 100 is moved along a path of travel PT to cut the skin tissue SK to produce the excised skin section EST. Moreover, the high rotary speed of the rotary knife blade 300 of the dermatome 100 reduces operator fatigue when removing large sections of skin tissue ST in a grafting region GR. The high rotary speed of the rotary knife blade 300 also facilitates making an initial incision (FIG. 17) in a layer of skin tissue SK at the cutting edge 360 of the rotary knife blade 300 without the need for applying counter traction to the skin tissue ST in the grafting region GR.

Advantageously, rotation of the depth adjustment knob 650 of the depth gauge assembly 600 quickly and precisely changes the axial position of the depth gauge plate 622 with respect to the cutting edge of the rotary knife blade 300, thereby allowing the operator to change the depth of cut DOC of the dermatome 100, as desired. The depth of cut DOC of the dermatome 100 directly determines the resulting excised skin tissue depth of cut DEST. By way of example and without limitation, the dermatome 100 of the present invention may be advantageously used for split thickness skin grafting (schematically depicted in FIGS. 17-19) and full thickness skin grafts (schematically depicted in FIG. 20). Approximate depth or thickness ranges for split thickness skin grafting may be categorized into three types of split thickness skin grafting: a) thin-type—skin tissue depth range 0.005 in.-0.012 in.; b) intermediate-type—depth range 0.012 in.-0.018 in.; and c) thick-type—depth range 0.018 in-0.030 in. The approximate depth or thickness range for full thickness skin grafting is 0.030 in.-0.043 in.

Figure 17:
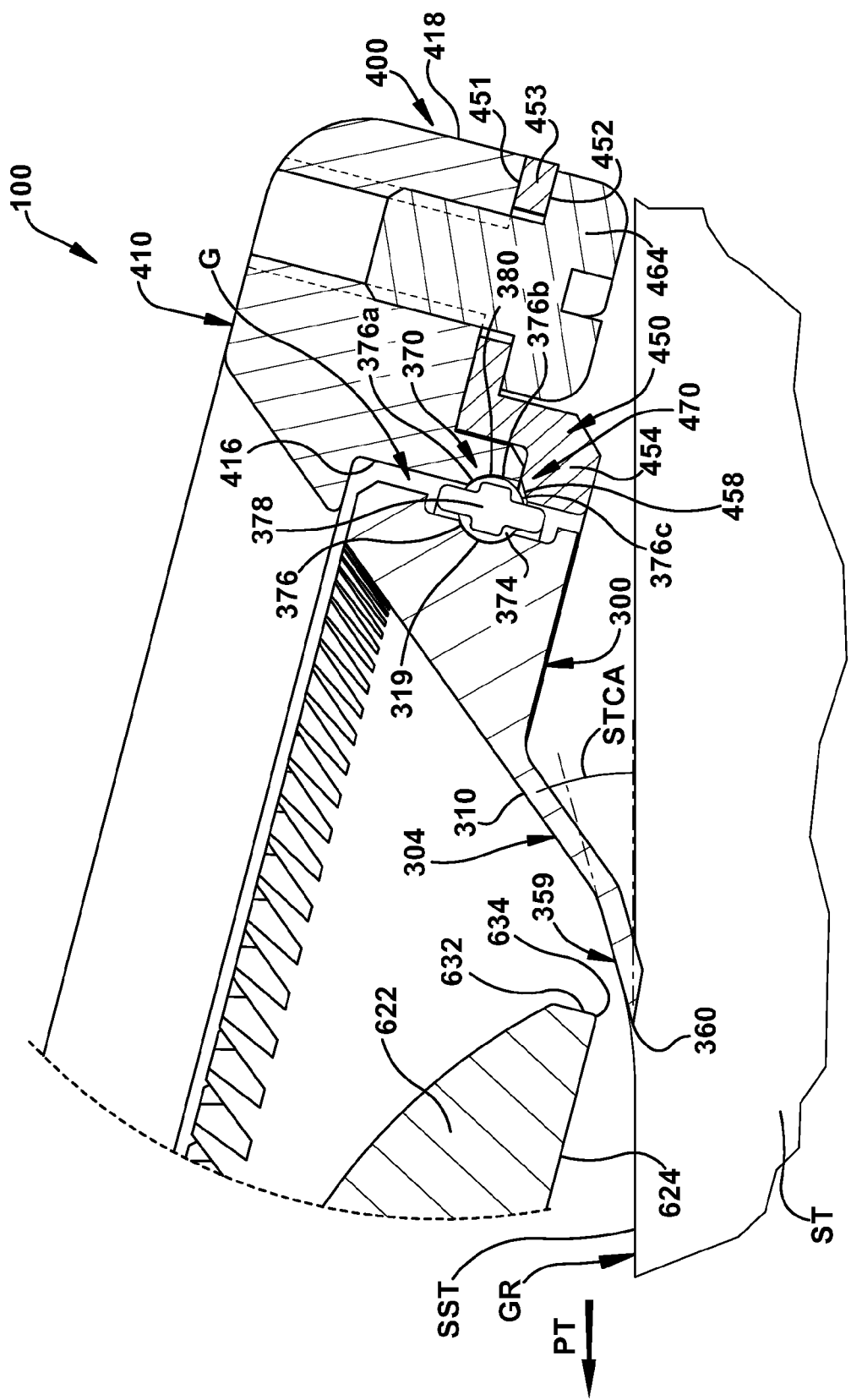

The dermatome 100 of the present disclosure provides for both rapid and precise adjustment of the dermatome depth of cut DOC and improved control and manipulation of the dermatome 100. These features enhance the ability of an operator to produce an excised skin tissue section EST having a desired depth of excised skin tissue DEST and having a consistent or uniform depth along the longitudinal extent LE of the excised skin tissue section EST, even when undertaking thin-type, split-thickness skin grafts wherein the desired depth or thickness of the excised skin tissue EST is in a range of approximately 0.005 in. to 0.012 in. in depth (FIGS. 17-19). Advantageously, the operator need only keep the cutting edge 360 of the dermatome 100 flush or flat against the skin tissue ST as the dermatome 100 is moved along its path of travel PT to excise a section of skin tissue EST. This makes the cutting procedure less dependent on operator skill level, as opposed to a cutting procedure where the operator was required to maintain a particular angle of the dermatome with respect to the skin tissue as the dermatome is moved along its path of travel or where the operator was required to change the angle of the dermatome with respect to the skin tissue as the dermatome is moved along its path of travel. The characteristics of the dermatome 100 of the present disclosure allow an operator to cut excised skin tissue sections EST of desired depth and substantially uniform depth from a patient/donor grafting region GR with less dependence on operator skill and more dependence on the attributes and characteristics of the dermatome 100.

Figure 5:
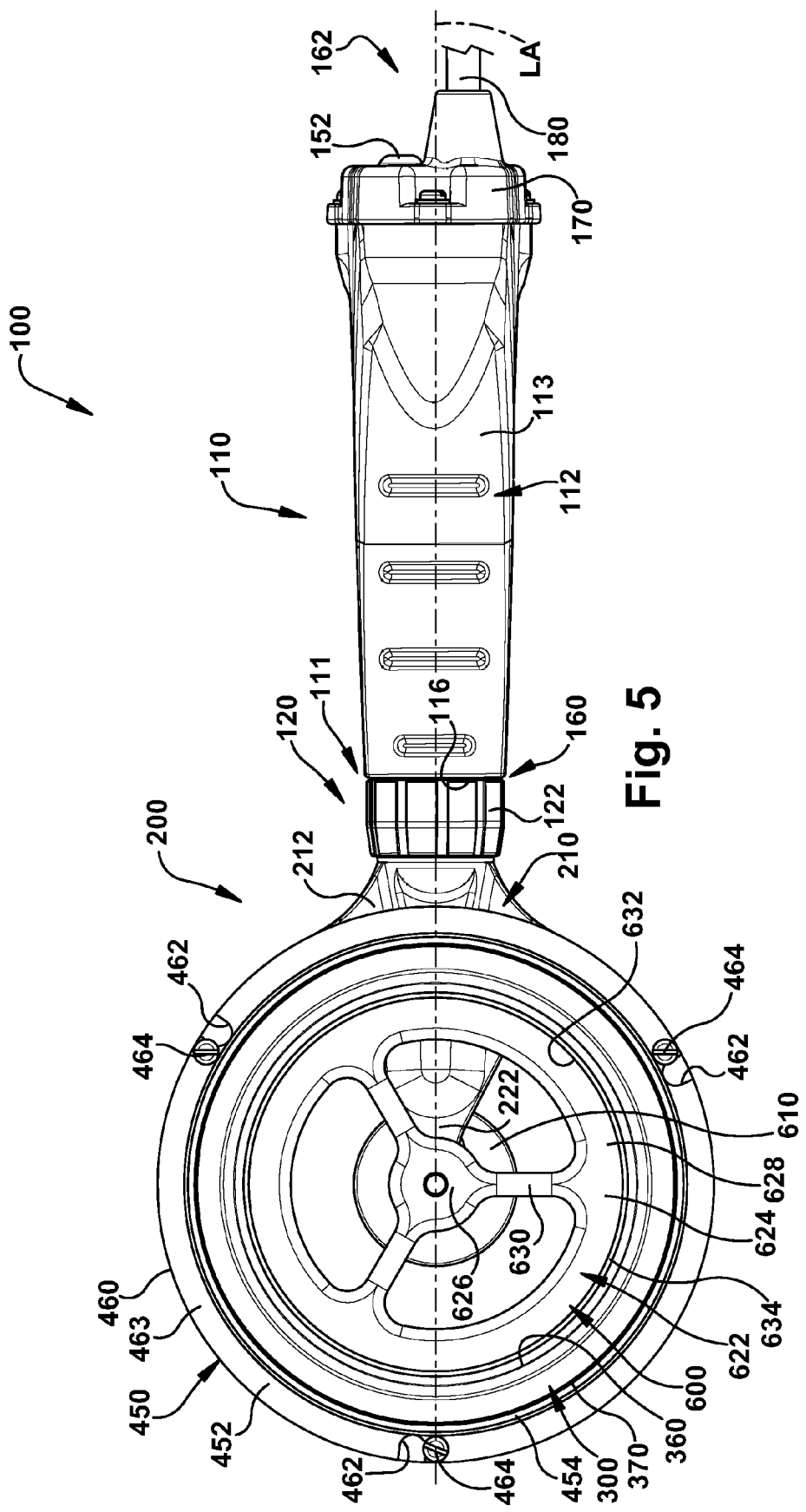
FIG. 5 is a schematic bottom plan view of the power operated dermatome of FIG. 1.
Figure 8:
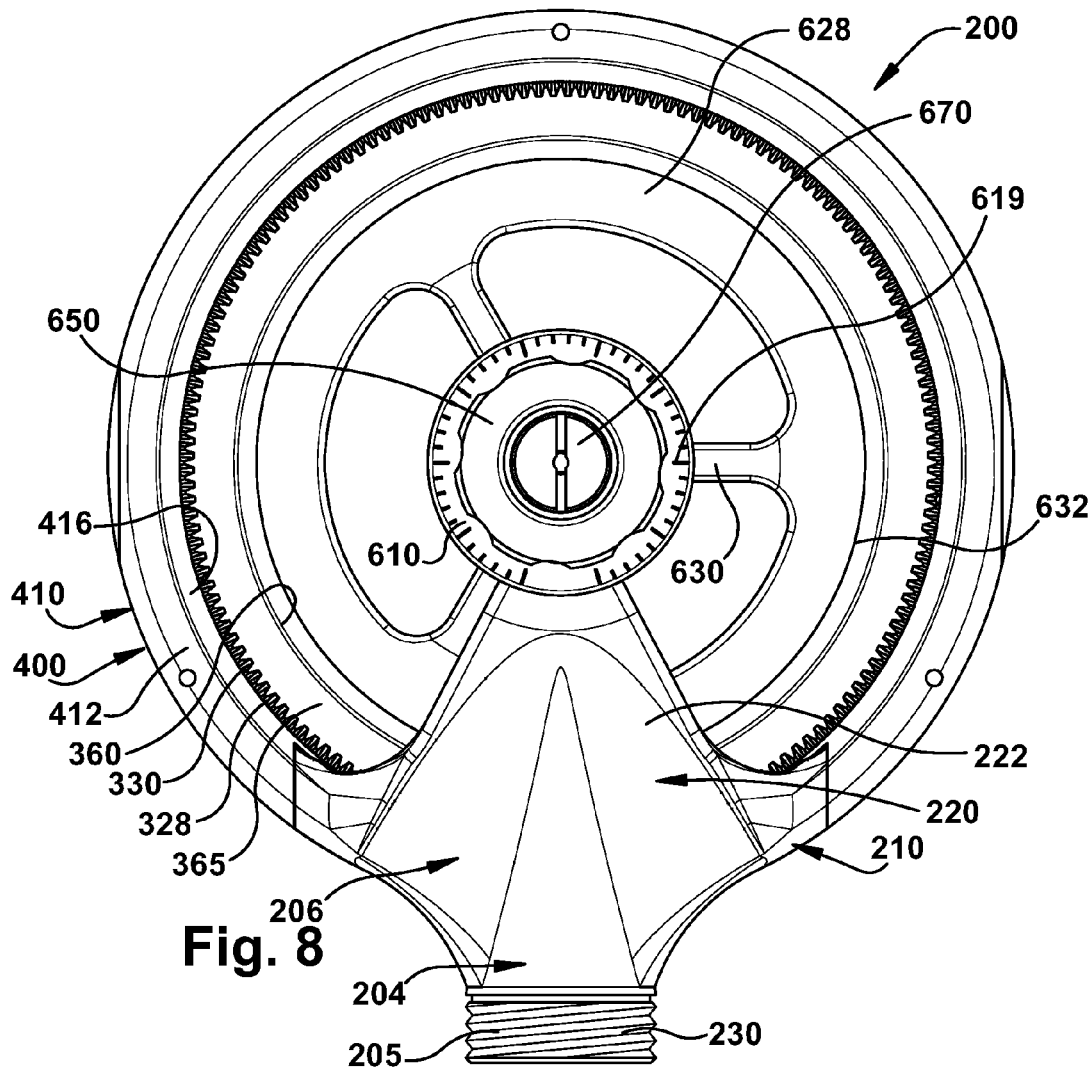
FIG. 8 is a schematic top plan view of the head assembly of the power operated dermatome of FIG. 1, with a gear train of the head assembly removed for clarity.
Figure 9:
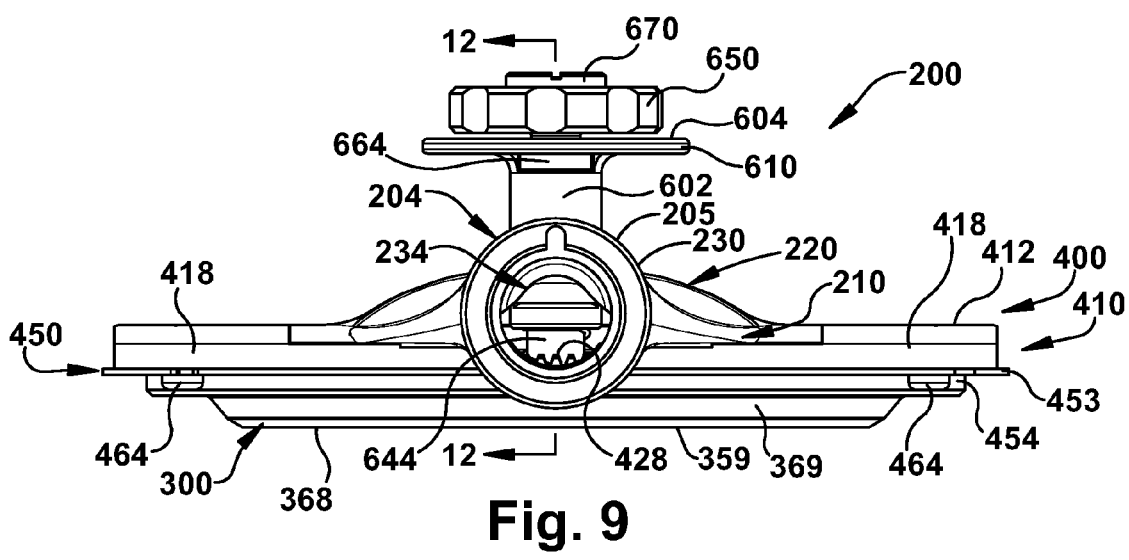
FIG. 9 is a schematic rear elevation view of the head assembly of FIG. 8.

Moreover, as can be seen in FIG. 5, because the cutting edge 360 of the rotary knife blade 300 of the dermatome 100 extends around the entire 360° circumference of the rotary knife blade 300, a cutting region of the dermatome 100 likewise extends 360° around the cutting edge 360. Thus, unlike prior manual or power operated dermatomes having a straight cutting blade and, therefore, were generally limited to a single cutting direction, the dermatome 100 of the present disclosure may advantageously used in any desired cutting direction—toward the operator, away from the operator, parallel to the operator, and any direction therebetween. Thus, the dermatome 100 of the present disclosure can be moved in various directions, as desired by the operator, to cut skin tissue SK from a grafting region GR, including a natural movement of sweeping the operator's hand and arm in a generally arcuate path inwardly toward the operator's body, thereby cutting the skin tissue section ST as the dermatome 100 along a generally arcuate path toward the operator's body. Advantageously, such a "toward the operator" cutting direction of the dermatome 100 facilitates a clear view of the grafting region GR by the operator. Further, advantageously, the range of cutting directions afforded by the dermatome 100 of the present disclosure facilitates maneuvering of the dermatome 100 around tight spaces and/or boney prominences in the grafting region GR.

First Exemplary Embodiment—Power Operated Dermatome 100

Figure 16:
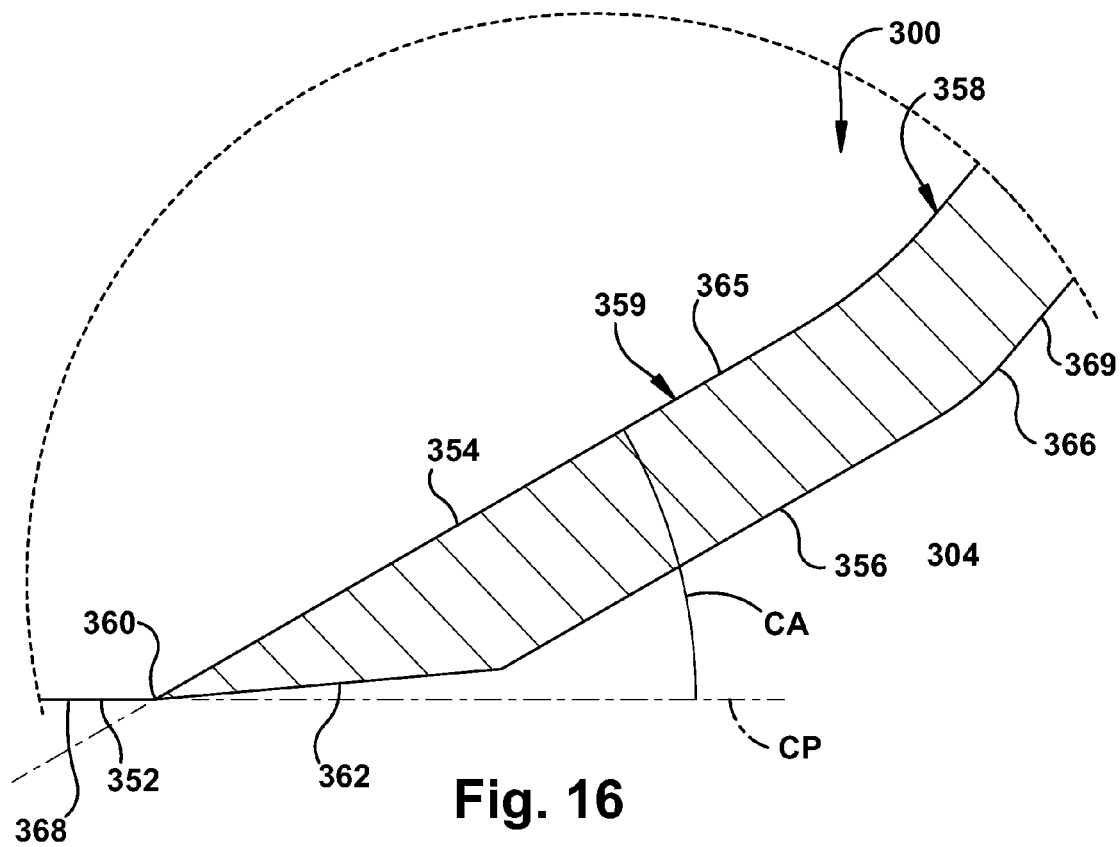
FIG. 16 is a schematic enlarged section view of a cutting edge portion of the rotary knife blade shown FIG. 15 that is within a dashed circle labeled FIG. 16 in FIG. 15.

A first exemplary embodiment of a hand-held, power operated dermatome of the present disclosure is schematically shown at 100 in FIGS. 1-7. The power operated dermatome 100 includes an elongated handle assembly 110 and a head assembly 200 extending from a forward or distal end 160 of the handle assembly 110. An attachment assembly 120 releasably affixes the head assembly 200 to the handle assembly 110. As is best seen in FIGS. 8-13, the head assembly 200 includes a frame body or frame housing 202, the rotary knife blade 300, an annular blade housing assembly 400 which rotatably supports the rotary knife blade 300 for rotation about the central axis of rotation R and the depth gauge assembly 600. The blade housing assembly 400 includes an annular blade housing 410 and a blade lock ring 450 which is releasably affixed to the blade housing 410 to trap and secure the rotary knife blade 300 for rotation with respect to the blade housing assembly 400. As is best seen in FIGS. 14-16, the rotary knife blade 300 includes a body section 302, a blade section 304 and a continuous rolling bearing structure 370 defining a portion of an outer peripheral surface 369 (FIG. 13) of the rotary knife blade 300. As can best be seen in FIG. 17, the continuous rolling bearing structure 370 is permanently affixed to a concave bearing surface 319 of the rotary knife blade body section 302 and, in turn, defines a convex bearing surface 380 of the rotary knife blade 300.

As can be seen schematically in FIG. 7, the rotary knife blade 300 is rotated with respect to the blade housing assembly 400 about the central axis of rotation R by a drive assembly 500 which includes a drive motor assembly 501 and a gear train 520. In one exemplary embodiment, the drive motor assembly 501 is supported by the handle assembly 110, while the gear train 520 is supported by a gearbox housing 203 of the frame body 202 of the head assembly 200. The depth gauge assembly 600 is also supported by the frame body 202 and includes a depth gauge support 602. The depth gauge support 602, which extends from the frame body 202, in turn, supports the depth gauge 620 including the depth gauge plate 622 and depth gauge shaft 640. The depth gauge 620 extends into the central interior region 301 of the rotary knife blade 300.

Handle Assembly 110 & Attachment Assembly 120

As can best be seen in FIGS. 1-5 and 7, the handle assembly 110 extends between the forward or distal end 160 and a rearward or proximal end 162 and includes an elongated handle 112 and a proximal or rear handle cover 170. The handle assembly 110 establishes and extends along a longitudinal axis LA. The longitudinal axis LA of the handle assembly 110 establishes a longitudinal axis of the dermatome 100. In one exemplary embodiment, the handle assembly longitudinal axis LA is substantially orthogonal to and intersects the central axis of rotation R of the rotary knife blade 300. An outer surface 113 of the handle 112 is contoured for easy gripping by the operator. The handle 112 includes a generally cylindrical, longitudinal throughbore 114 which supports the drive motor assembly 501 of the drive assembly 500. A forward or front end 116 of the handle 112 includes a radially inwardly stepped portion 118 that serves as an attachment point for the attachment assembly 120.

In one exemplary embodiment, the drive motor assembly 501 is actuated by a combination of an actuation lever 150 which is pivotally mounted with respect to the handle 112, a lever sensing switch 151, and an actuation switch 152. When the actuation lever 150 is pivoted to an "on" position, generally parallel to the outer surface 113 of the handle 112, a lever sensing switch 151 disposed within the handle throughbore is tripped. An actuation switch 152 is located on the cover 170 at the proximal end 162 of the handle assembly 110. When the actuation lever 150 is pivoted to the "on" position and the actuation switch 152 is pressed within five seconds of the tripping of the lever sensing switch 151, the drive assembly 500 is actuated to rotate the rotary knife blade 300. If the actuation switch 152 is not pressed within five seconds of the tripping of the lever sensing switch 151, the actuation lever 150 must be released and again pivoted to the "on" position. Alternately, the drive motor assembly 501 may be actuated by a foot pedal valve positioned at the feet of the operator affixed to the handle assembly 110 or a toggle or rocker switch mounted on the handle assembly 110.

The handle assembly 110 extends orthogonally in a rearward direction RW (FIG. 7) away from the head assembly 200 along the handle axis longitudinal axis LA. The longitudinal axis LA is substantially orthogonal to the blade central axis of rotation R and parallel to the cutting plane CP of the rotary knife blade 300. This configuration allows the operator of the dermatome 100 to wield and manipulate the dermatome 100 effectively using one hand. The rear handle cover 170 of the handle assembly 110 overlies a proximal end of the handle 112 and is coupled to an air line or air hose 180 which provides a source of high pressure air to provide motive power to the drive motor assembly 501.

The attachment assembly 120 includes a coupling collar 122, a retainer 128 and an inner sleeve 130 that attaches to the inwardly stepped portion 118 at the front end 116 of the handle 112. The coupling collar 122 includes an inner surface 124 having a threaded portion 126. As can best be seen in FIG. 7, the coupling collar 122 is rotatably secured to the handle 112 by the retainer 128 and the inner sleeve 130. In turn, the coupling collar 122 threads onto a threaded outer surface 230 of the frame body 202 to releasably secure the head assembly 200 to the forward end 160 of the handle assembly 110. Advantageously, the attachment assembly 120 allows for easy coupling and decoupling of the head assembly 200 from the handle assembly 110 to facilitate disassembly and sterilization of components of the head assembly 200 upon completion of a skin grafting or other medical procedure performed with the dermatome 100.

As used herein, axial, upper and lower shall mean movement or a dimension in a direction generally along or parallel to an extent of the central axis of rotation R. Forward or distal shall mean in a direction generally along a direction labeled FW in FIG. 7, the forward direction FW being generally parallel to or along the longitudinal axis LA. Rearward or proximal shall mean a direction generally along a direction labeled RW (opposite of the forward direction FW) in FIG. 7.

Drive Assembly 500

As best seen in FIG. 7, the drive assembly 500 includes the drive motor assembly 501 and the gear train 520. The present disclosure contemplates at least three different drive motor assemblies, an air motor embodiment (schematically shown in FIG. 7) and, alternatively, an electric motor disposed in the handle assembly (not shown), and a flexible drive shaft embodiment (not shown) to provide motive power to rotate the rotary knife blade 300 within the blade housing assembly 400. In one exemplary embodiment, the drive motor assembly 501 includes a vane-type air or pneumatic motor 502 and a planetary gear reduction unit 504 disposed within the longitudinal throughbore 114 of the handle 112. High pressure air is communicated via the air hose 180 coupled to the cover 170 at the proximal end 162 of the handle assembly 110 and directed into the motor 502. The air is routed through the motor body and directed against a plurality of vanes to rotate a rotor of the motor 502. The rotor includes an output shaft 503 coupled to the planetary gear reduction unit 504. The planetary gear reduction unit 504 serves to convert the high rotational speed of the rotor shaft to a drive coupling 506 that rotates at a lower speed but a higher torque output than the rotor shaft 503.

Figure 1:
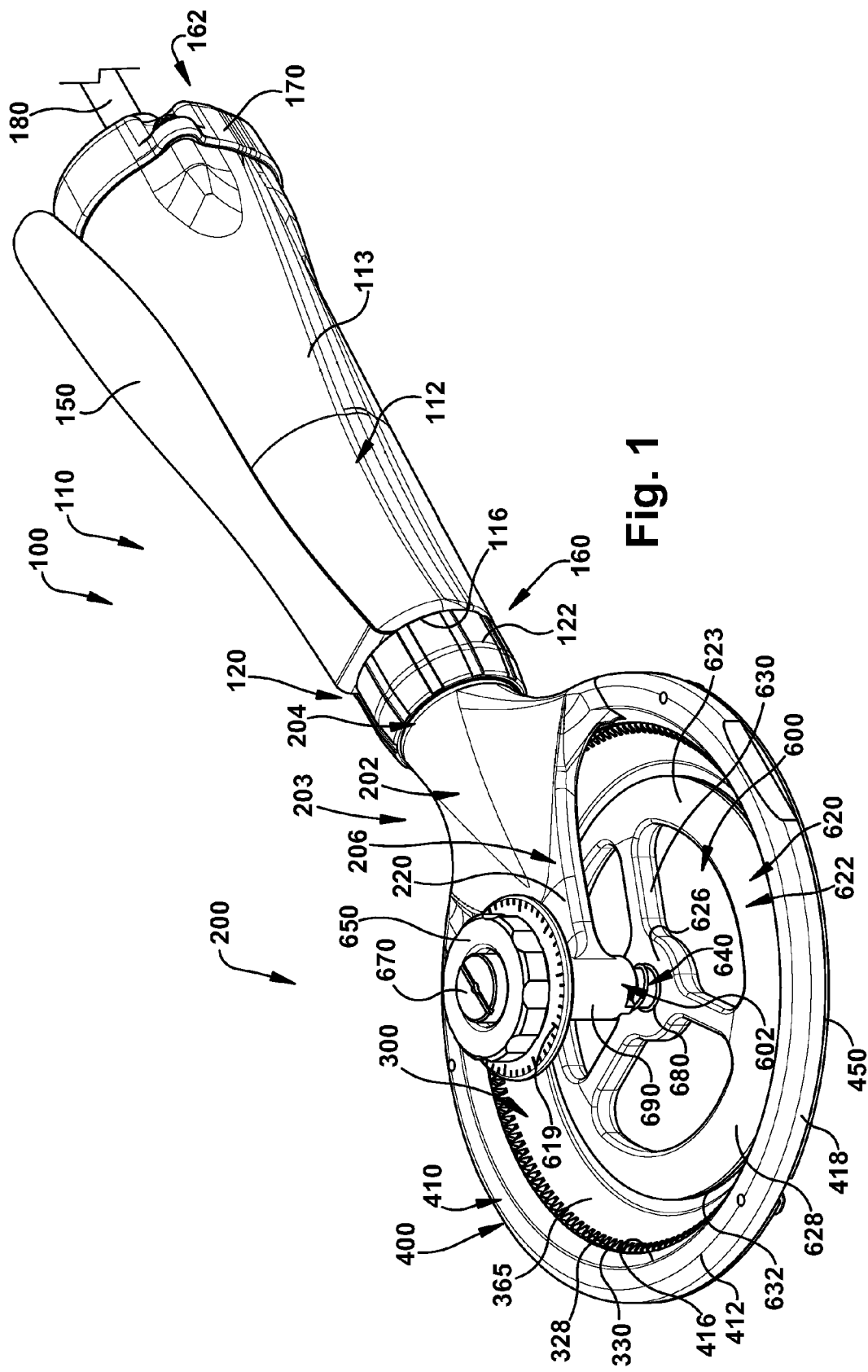
FIG. 1 is a schematic perspective view of a first exemplary embodiment of a hand-held, power operated dermatome of the present disclosure including a handle assembly and a head assembly including a rotary knife blade and a depth gauge assembly extending into a central, interior region defined by the rotary knife blade.
Figure 2:
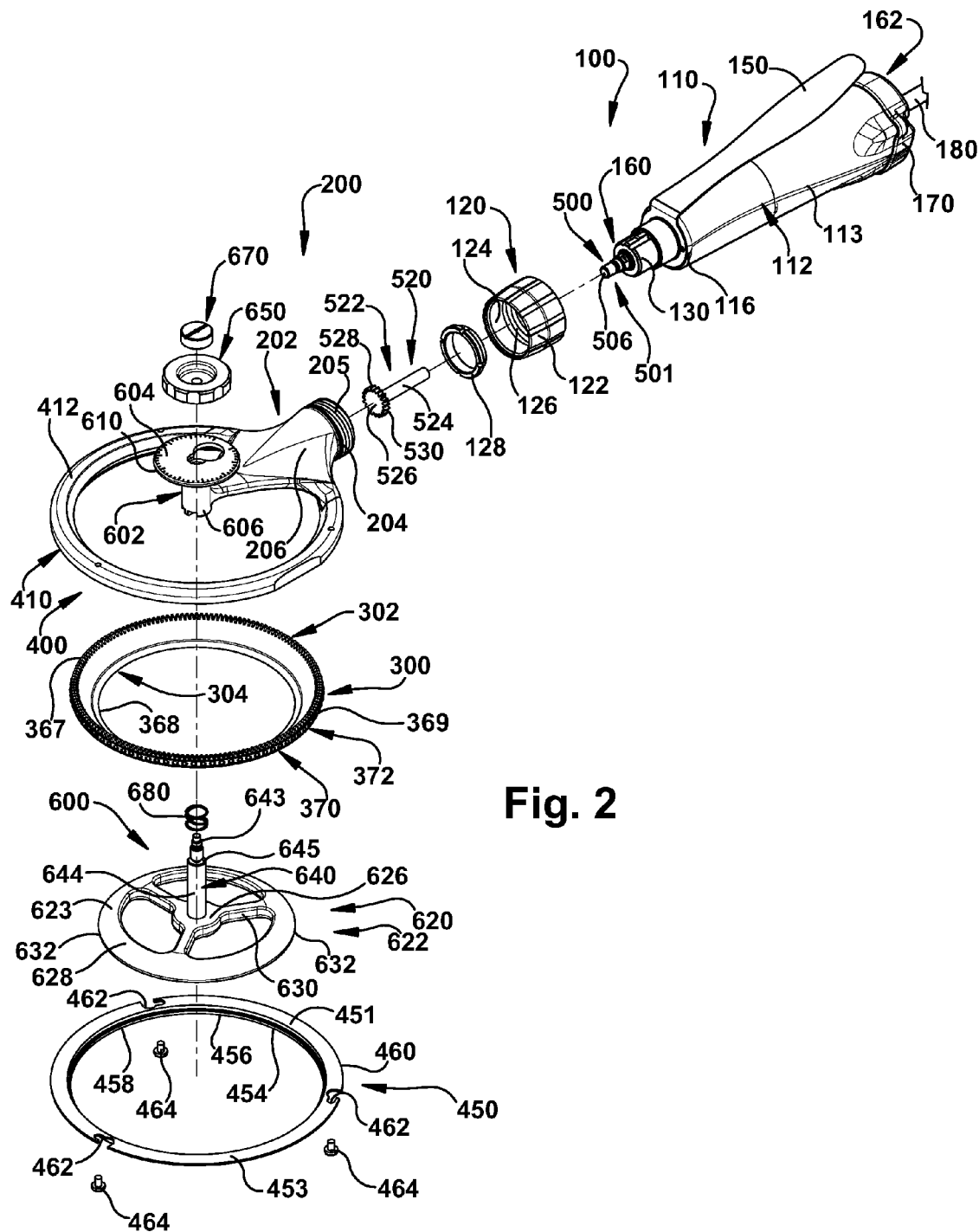
FIG. 2 is a schematic exploded perspective view of the power operated dermatome of FIG. 1.
Figure 3:
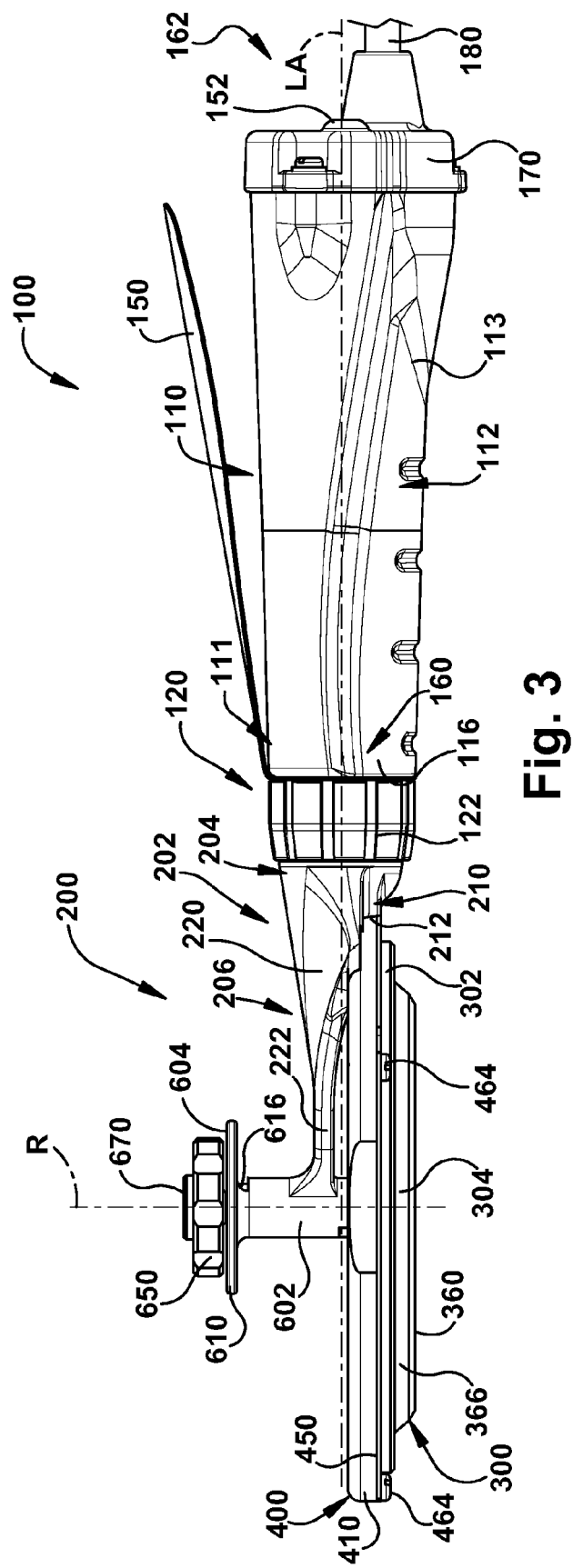
FIG. 3 is a schematic side elevation view of the power operated dermatome of FIG. 1.
Figure 4:
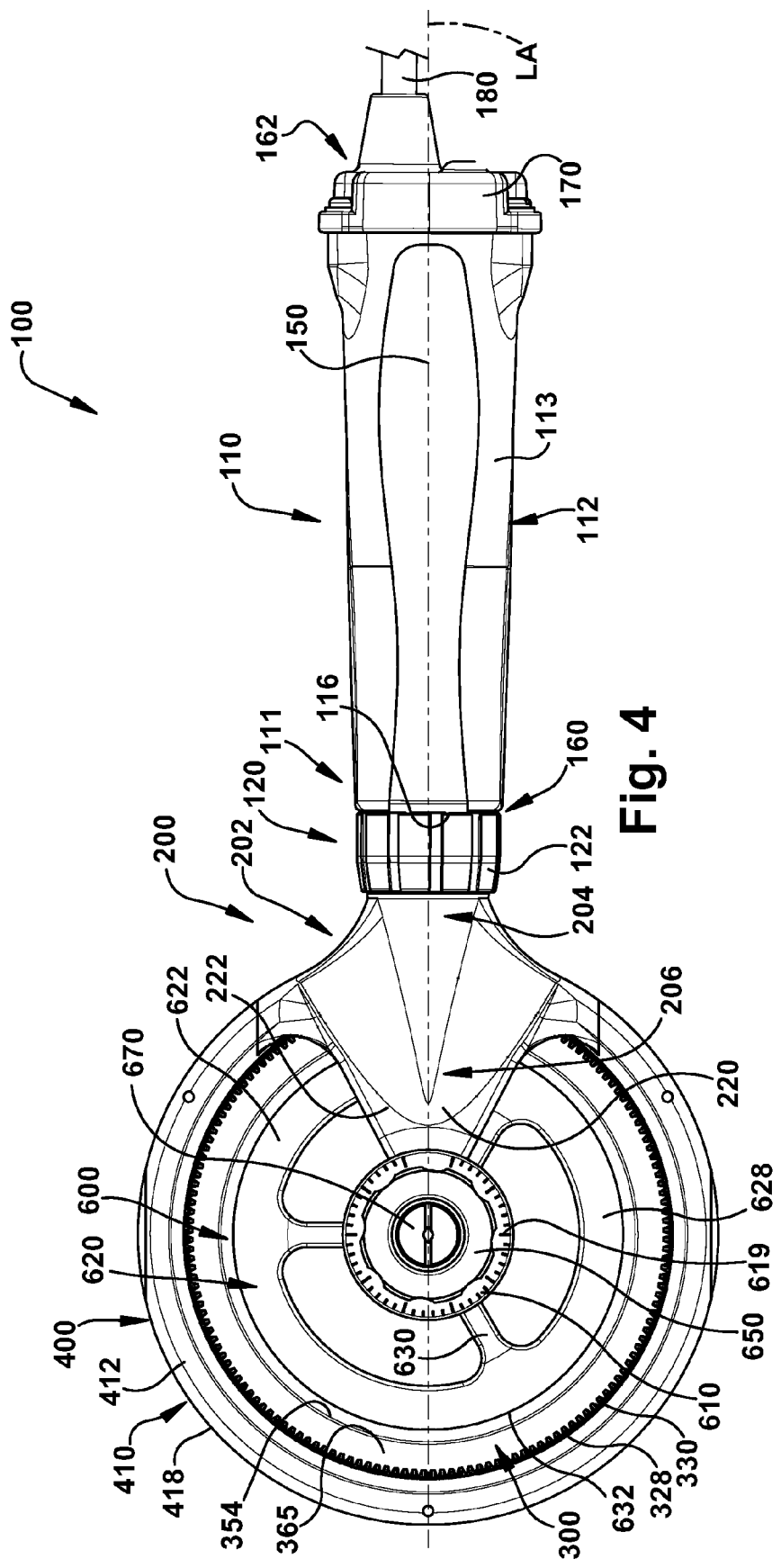
FIG. 4 is a schematic top plan view of the power operated dermatome of FIG. 1.

In one exemplary embodiment, the gear train 520 comprises a pinion gear 522 (FIG. 2). An input shaft 524 at a proximal end of the pinion gear 522 receives the drive coupling 506 of the drive motor assembly 501. The pinion gear 522 includes a gear head 526 at its distal end. In one exemplary embodiment, the gear head 526 defines a bevel gear 528 including a set of bevel gear teeth 530. The pinion gear 522 is supported for rotation in the gearbox housing 203 of the frame body 202 about a pinion gear axis of rotation PGR (FIG. 7) and is positioned such that the set of bevel gear teeth 530 of the pinion gear 522 meshes with a mating set of bevel gear teeth 330 of a driven gear 328 of the rotary knife blade 300. The gear head 526 of the pinion gear 522 engages and drives the driven gear of the rotary knife blade 300 to rotate the blade 300 about its axis of rotation R.

As can be seen in FIG. 7, the pinion gear axis of rotation PGR is substantially congruent with the handle assembly longitudinal axis LA. As the drive coupling 506 of the drive motor assembly 501 rotates the pinion gear 522 within the gearbox housing 203. Rotation of the pinion gear 522, in turn, rotates the rotary knife blade 300 about its axis of rotation R. A suitable pneumatic motor/planetary gear reduction unit configuration is disclosed in U.S. patent application Ser. No. 13/073,207 to Whited et al., filed Mar. 28, 2011, and entitled Power Operated Rotary Knife With Disposable Blade Support Assembly ("the '207 application"). The '207 application is assigned to the assignee of the present application and is incorporated herein, in its entirety, by reference.

Alternatively, the drive motor assembly 501 may comprise an external drive motor, for example, an external brushless DC servo motor, and a flexible shaft drive transmission (not shown). The drive motor assembly rotates a drive shaft of a flexible shaft drive transmission. A portion of the flexible shaft drive transmission extends through the longitudinal throughbore 114 of the elongated handle 112 of the handle assembly 110. A suitable DC motor/flexible drive shaft transmission configuration is disclosed in U.S. patent application Ser. No. 13/344,760 to Rapp et al., filed Jan. 6, 2012, and entitled Flex Shaft—Drive Motor Connection For Power Operated Rotary Knife ("the '760 application"). The '760 application is assigned to the assignee of the present application and is incorporated herein, in its entirety, by reference.

Alternately, the drive motor assembly 501 may comprise an electric drive motor disposed within the longitudinal throughbore 114 of the handle 112. In one exemplary embodiment, the electric drive motor is a DC motor. A suitable DC electric motor, for example, the Maxon Model No. EC22 386680 and an associated gear reduction unit, for example, the Maxon Model No. GPM 22M 305130, may be obtained from Maxon Motor AG, Sachsein, Switzerland (www.maxonmotor.com).

Head Assembly 200

Turning to FIGS. 8-13, the head assembly 200 of the power operated dermatome 100 of the present disclosure includes the frame body 202, the rotary knife blade 300, the annular blade housing assembly 400, and the depth gauge assembly 600. In the dermatome 100, both the depth gauge assembly 600 and the blade housing assembly 400 are supported by and extend from the frame body 202. The depth gauge plate 622 of the depth gauge assembly 600 extends into the interior region 301 of the rotary knife blade 300. A lower edge region 634 of the depth gauge plate 622, in combination with the cutting edge 360 of the rotary knife blade 300, determine the depth of cut DOC of the dermatome 100.

Frame Body 202

As best seen in FIGS. 8-13, the frame body 202 includes a rearward handle attachment portion 204 and a forward interface portion 206. The rearward handle attachment portion 204 comprises a generally cylindrical body 205 defining the threaded outer surface 230 of the frame body 202. The threaded outer surface 230 of the frame body cylindrical body 205 is engaged by the attachment assembly 120 to releasably affix the head assembly 200 to the handle assembly 110.

The frame body 202 includes a gearbox housing 203 which rotatably supports gear train 520 of the drive assembly 500, specifically, the pinion gear 522. The gearbox housing 203 includes an inner surface 208 of the frame body 202. The inner surface 208 defines a longitudinally extending throughbore 209. As seen in FIG. 7, the pinion gear 522 is seated in the throughbore 209. A front opening 232 (FIGS. 11 and 12) of the throughbore 209 is configured to allow the gear head 526 of the pinion gear 522 to engage the driven gear 328 of the rotary knife blade 300. A rear opening 234 (FIGS. 9 and 12) of the throughbore 209 allows entry of the drive coupling 506 of the drive motor assembly 501 into the pinion gear input shaft 524 when the head assembly 200 is releasably affixed to the handle assembly 110.

The forward interface portion 206 of the frame body 202 includes an upper interface region 220 that extends or transitions between the cylindrical body 205 of the rearward handle attachment portion 204 and the central cylindrical support 602 of the depth gauge assembly 600. In one exemplary embodiment, the upper interface region 220, when viewed from above in plan view, comprises a generally V-shaped rib 222 wherein the V-shaped rib 222 is widest adjacent to the cylindrical body 205 and tapers or converges in a direction proceeding toward the central cylindrical support 602, that is, the central cylindrical support 602 can be viewed as serving as a termination or vertex of the rib 222. Thus, the central cylindrical support 602 of the depth gauge assembly 600 is attached to and extends from the frame body 202 and, more specifically, the depth gauge assembly 600 is attached to and extends from the upper interface region 220 of the frame body 202.

Positioned axially below the upper interface region 220 is a lower interface region 210 that extends or transitions between the cylindrical body 205 of the rearward handle attachment portion 204 and the annular blade housing 410 of the blade housing assembly 400. In one exemplary embodiment, the lower interface region 210, when viewed from below in plan view, comprised a Y-shaped support 212 that includes arms that extend circumferentially about the annular blade housing 410. Thus, the annular blade housing 410 of the blade housing assembly 400 is attached to and extends from the frame body 202 and, more specifically, the lower interface region interface region 220 of the frame body 202.

Rotary Knife Blade 300

As can best be seen in FIGS. 14-17, in one exemplary embodiment, the annular rotary knife blade 300 includes an inner wall 365 and an outer wall 366 and a first upper end 367 and a second lower end 368. The inner wall 365 defines the open, interior region 301 of the rotary knife blade 300. The rotary knife blade 300 includes the upper body section 302, the lower blade section 304 and the continuous rolling bearing structure 370. The continuous rolling bearing structure 370 forms a portion of a peripheral outer surface 303 of the body section 302 and define the convex bearing surface 380 of the rotary knife blade 300. The upper body section 302 extends between a first upper end 306 and a second lower end 308. The upper end 306 corresponds to and is congruent with the first upper end 367 of the rotary knife blade 300. A radially extending shoulder 308a between the body section 302 and the blade section 304 defines the second lower end 308 of the body 302. The body section 302 includes an inner wall 310 and a radially spaced apart outer wall 312. The first upper end 306 of the body section 302 defines the driven gear 328 of the rotary knife blade 300. The driven gear 328 comprises the set of bevel gear teeth 330 that operatively engage and mesh with the bevel gear 528 of the pinion gear 522, as previously discussed, such that rotation of the bevel gear 528 results in rotation of the rotary knife blade 300 about its axis of rotation R.

The body section 302 of the rotary knife blade 300 includes a bearing surface 319 formed in the outer wall 312 of the body 302. In one exemplary embodiment, the bearing surface 319 comprises a bearing race 320 that extends radially inwardly into the outer wall 312. The bearing race 320 includes a generally convex arcuate bearing face 322. The bearing face 322 provides a seating surface for the continuous rolling bearing structure 370 of the rotary knife blade 300. The continuous rolling bearing structure 370 defines the convex bearing surface 380 of the rotary knife blade 300 that projects radially outwardly from the outer wall 312 of the body section 302 of the blade 300 and thereby forms a portion of a peripheral outer surface 303 of the body section 302 and forms a portion of a peripheral outer surface 369 of the rotary knife blade 300. The continuous rolling bearing structure 370 rotationally supports the rotary knife blade 300 with respect to the blade housing assembly 400.

The continuous rolling bearing structure 370 comprises an annular rolling bearing strip 372 that extends continuously 360° around the periphery of the outer wall 312 of the body section 302 and is disposed in the bearing race 320. The rolling bearing strip 372 includes a plurality of spaced apart ball bearings 376 rotatably supported in radially spaced apart pockets of a separator cage 378. In one exemplary embodiment, the separator cage is flexible and a diameter of each of the ball bearings 376 is approximately 2 mm., although it should be understood that the diameter could be larger or smaller. Portions of the plurality of ball bearings 376 extend radially outwardly from the outer wall 310 of the blade body section 302 and thus form a part of the outer periphery 303 of the body section 302. Specific details concerning the structure and configuration of the plurality of spaced apart ball bearings and the flexible separator cage are disclosed in U.S. patent application Ser. No. 13/189,951, filed Jul. 25, 2011 to Whited et al., and entitled Power Operated Rotary Knife ("the '951 application"). The '951 application is assigned to the assignee of the present application and is incorporated herein, in its entirety, by reference.

The rolling bearing strip 372 is disposed in an annular gap G defined between opposing faces of the rotary knife blade 300, the blade housing 410 and a blade lock ring 450 of the blade housing assembly 400, in the region of the rotary knife blade bearing race 320. Specifically, the plurality of ball bearings 376 of the rolling bearing strip 372 are disposed within an annular passageway 374, which is circular in cross section and defined by the opposing arcuate bearing surfaces 319, 426, 458 of the rotary knife blade 300, the blade housing 410 and the blade lock ring 450, respectively.

By virtue of the annular rolling bearing strip 372 being continuous and disposed within the bearing race 320, the strip 372 is permanently affixed to and thus is part of the blade 300. However, as the plurality of ball bearings 376 of the rolling bearing strip 372 contact the blade bearing race 320, the rolling bearing may rotate with respect to the blade body 302 and the blade section 304 of the blade 300. When rotary knife blade 300 is rotated by the drive assembly 500 and, specifically, the pinion gear 522, at a specific, desired RPM, the separator cage 378 also moves or translates in a circle along the annular gap G, although the rotational speed of the separator cage 378 within the gap G is less than the RPM of the rotary knife blade 300. Thus, when the dermatome is in operation, the continuous, annular rolling bearing strip 372 traverses through the annular passageway 374 forming a circle about the knife blade axis of rotation R. Similarly, when the dermatome 100 is in operation, the separator cage 378, due to its movement or translation along the annular gap G about the knife blade axis of rotation R, can be considered as forming a complete cylinder within the gap G. Additionally, when the rotary knife blade 300 is rotated, the plurality of ball bearings 376 both rotate with respect to the separator cage 378 and also move or translate along the annular passageway 374 about the knife blade axis of rotation R as the separator cage 378 moves or translates along the annular gap G. A plane passing through the respective centers of the plurality of ball bearings 376 define a rotational plane RP (FIGS. 13 and 15) of the rotary knife blade 300. The rotational plane RP of the rotary knife blade 300 is substantially parallel to the cutting plane CP of the blade 300 and substantially orthogonal to the axis of rotation R of the blade 300.

The rotary knife blade 300 also includes the blade section 304 extending between a first upper end 350 (adjacent the shoulder 308a of the body section 302) and a second lower end 352. The second lower end 352 corresponds to and is congruent with the lower end 368 of the rotary knife blade 300. The blade section includes an inner wall 354 and a radially spaced apart outer wall 356. The inner and outer walls 354, 356 are generally parallel and frustoconical, converging in a direction proceeding downwardly or toward the cutting edge 360 of the blade. The cutting edge 360 of the rotary knife blade 300 is generally circular. The inner wall 310 of the body section 302 and the inner wall 354 of the blade section 304 combine to form the inner wall 365 of the rotary knife blade 300 and define the interior region 301 of the blade 300. The interior region 301 of the rotary knife blade is generally frustoconical, converging in a direction toward the cutting edge 360 of the blade 300. A plane aligned with the generally circular cutting edge 360 of the rotary knife blade 300 defines the cutting plane CP (FIG. 15) of the blade 300.

In one exemplary embodiment, the blade section 304 includes an upper region 358 and a lower region 359 separated by a knee or discontinuity between the two regions. Of course, it should be recognized that the blade section 304 may comprise a single region with no discontinuity. The lower region 359 defines the cutting angle CA of the blade and is defined by an angle between the inner wall 354 in the lower region 359 of the blade section 304 and the cutting plane CP. In one exemplary embodiment, the cutting angle CA is approximately 30°, although it should be understood that the cutting angle CA could be greater or smaller. As can be best seen in FIG. 16, the lower end 352 of the blade section 304 which defines the cutting edge 360, includes a short section of wall 362 bridging the inner and outer walls 354, 356. The cutting edge 360 is formed at the intersection of the short section of wall 362 and the inner wall 354. The short section of wall 362 is slightly angled with respect to the cutting plane CP, at about 5° in one exemplary embodiment, to provide relief for the cutting edge 360.

In one exemplary embodiment, the inner diameter (defined by the cutting edge 360) of the rotary knife blade 300 is approximately 4.000 in., while the outer diameter (defined by the outer periphery of the plurality of ball bearings 376 the rolling bearing strip 372 is approximately 5.189 in., although it should be understood that the diameters could be larger or smaller.

Blade Housing Assembly 400

As can best be seen in FIGS. 10-13 and 16-17, the blade housing assembly 400 includes the annular blade housing 410 and the blade lock ring 450. The annular blade housing 410 extends from and is supported by the Y-shaped support 212 of the lower interface region 210 of the forward interface portion 206 of the frame body 202. The blade housing 410 includes a first upper end 412 and an axially spaced apart second lower end 414. The blade housing 410 further includes an inner wall 416 and a radially spaced apart outer wall 418. The blade housing 410 includes three peripherally spaced apart threaded openings 430 of the blade housing 410. The three threaded openings 430 extend from the second lower end 414 through the first upper end 412. The inner wall 416 of the blade housing 410 includes a bearing surface 420. In one exemplary embodiment, the bearing surface 420 comprises a bearing race 422 that extending radially inwardly into the inner wall 416 of the blade housing 410. The bearing race 422 includes the concave, arcuate bearing surface or face 426.

Figure 13:
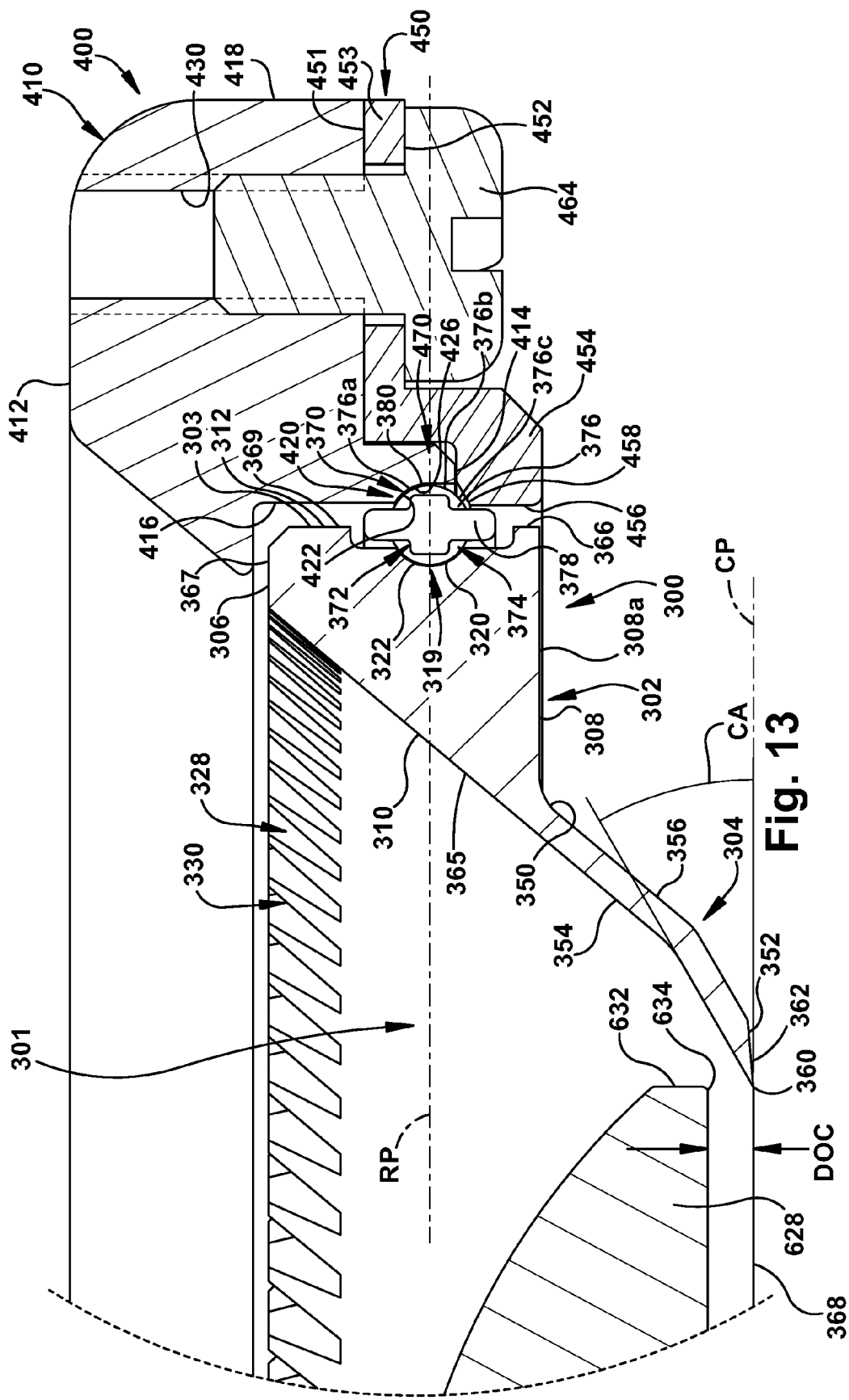
FIG. 13 is a schematic enlarged section view of a portion of the head assembly of FIG. 8 that is within a dashed circle labeled FIG. 13 in FIG. 12.

As can be best be seen in FIGS. 13, 17 and 18, in axial extent, the arcuate bearing face 426 is a curved bearing surface that extends from an upper region 376a of the ball bearing 376 and generally conforms to the curvature of the ball bearing 376 to about a midpoint 376b of the ball bearing 376. The arcuate bearing face 426 does not, however, extend all the way to a lower region 376c of the ball bearing 376. Instead, an arcuate bearing surface or face 458 formed on an inner surface 456 of the blade lock ring 450 constitutes a portion of a total bearing race 470 (FIGS. 17 and 18) provided by the blade housing assembly 400. The total bearing race 470 defined by the blade housing assembly 400 results from a combination of the bearing surfaces of the blade housing 410 and the blade lock ring 450, specifically, the arcuate bearing face 426 of the blade housing 410 and the arcuate bearing face 458 of the blade lock ring 450. The total bearing race 470 serves as an arcuate bearing surface for the annular rolling bearing strip 372 of the rotary knife blade 300 when the blade lock ring 450 is secured to the blade housing 410 and the rotary knife blade 300 is captured or sandwiched therebetween.

The blade lock ring 450 includes an upper surface 451 and a lower surface 452 and comprises an upper seating region 453 and a radially inwardly offset lower bearing region 454. The upper seating region 453 seats flush against the blade housing 410 and includes three peripherally spaced apart slots 462 in an outer periphery 460 of the blade lock ring 450. The blade lock ring 450 adapted to be secured to a stepped shoulder 415 (FIG. 18) near the lower end 414 of the blade housing 410. The blade lock ring 450 is secured to the stepped shoulder 415 of the blade housing 410 via three threaded fasteners 464, each of which passes through a correspond peripherally spaced apart slot 462 in an outer periphery 460 of the blade lock ring 450.

To install or affix the rotary knife blade 300 to the blade housing assembly 400, with the blade lock ring removed, the head assembly 200 is turned upside down and the rotary knife blade 300 is placed in the upside down blade housing 410. The plurality of ball bearings 376 of the rotary knife blade 300 rest on the bearing race 422 of the blade housing 410 thereby the rotary knife blade 300 is supported by the blade housing 410. The three slots 462 of the blade lock ring 450 are aligned with the threaded openings 430 of the blade housing 410. The three threaded fasteners 464 pass through the slots 462 and are threaded into the threaded openings 430 of the blade housing 410 to complete the installation. Because of the configuration of the three slots 462, it is only necessary to loosen the three threaded fasteners 464 a sufficient amount to rotate the blade lock ring 450 with respect to the blade housing 410. This allows the blade lock ring 450 to be removed from the blade housing 410 without removing the three threaded fasteners 464 from the threaded openings 430 of the blade housing 410. When the blade lock ring 450 is removed from the blade housing 410 turning the head assembly 200 upside down causes the rotary knife blade 300 to fall out of the blade housing 410 thereby removing the blade 300 from the blade housing assembly 400.

Depth Gauge Assembly 600

Figure 10:
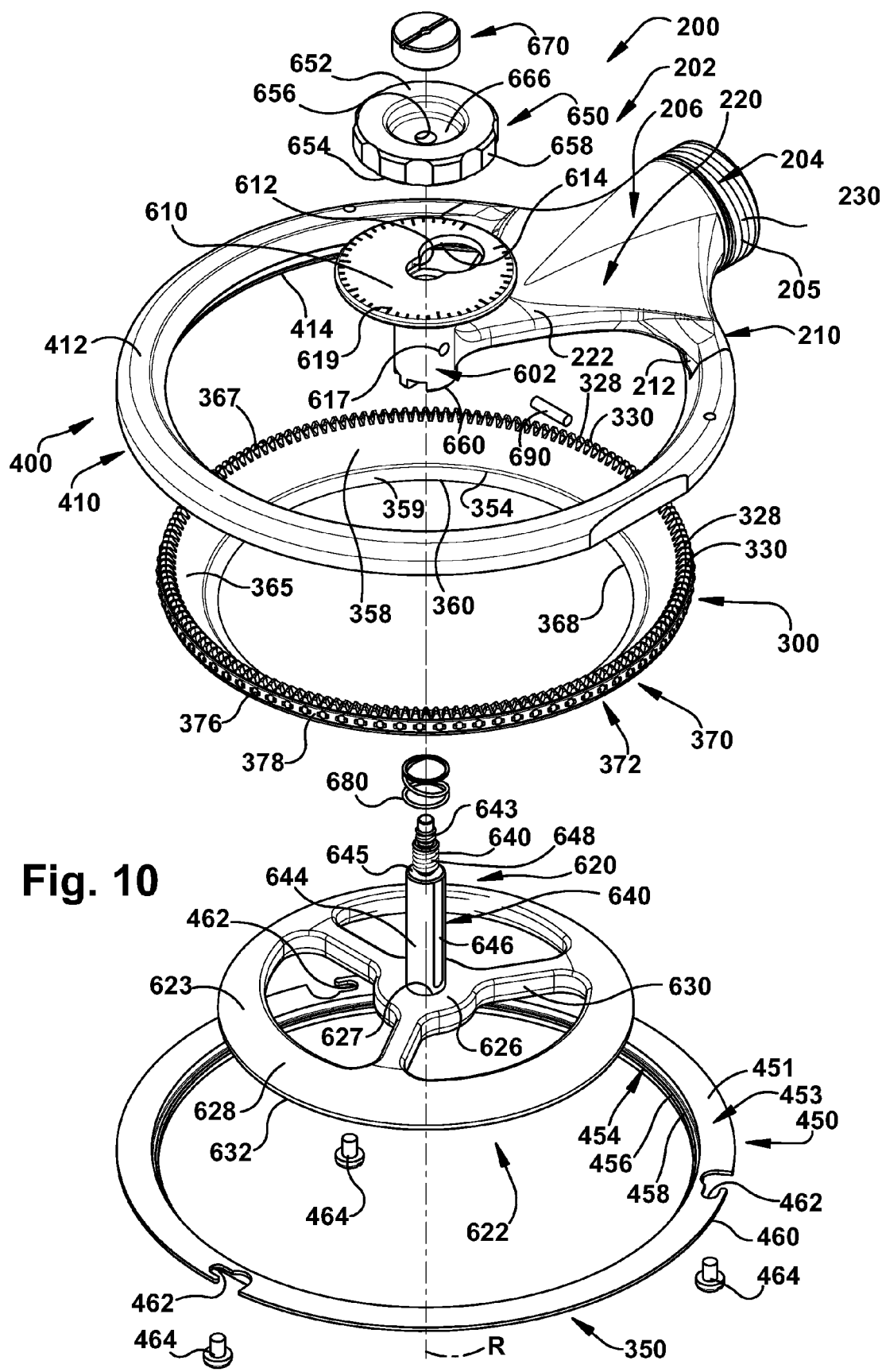
FIG. 10 is a schematic exploded top perspective view of the head assembly of FIG. 8.
Figure 11:
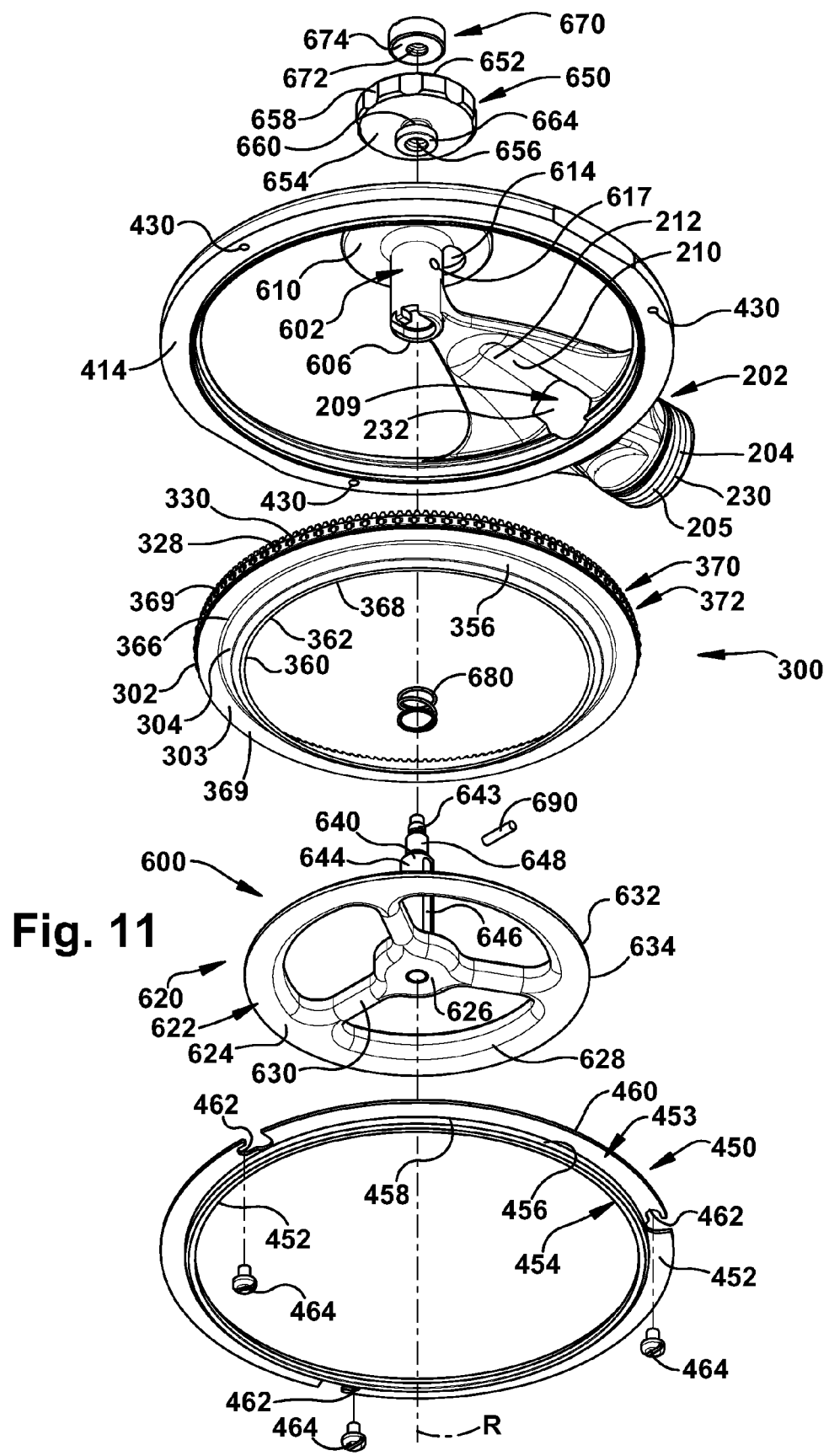
FIG. 11 is a schematic exploded bottom perspective view of the head assembly of FIG. 8.

As can best be seen in FIGS. 10-13 and 17-21, the depth gauge assembly 600 includes the depth gauge support 602 and the depth gauge 620. The depth gauge 620 includes the depth gauge shaft 640 and the depth gauge plate 622. The depth gauge assembly 600 further includes the depth adjustment knob 650, a stop ring 670, a biasing spring 680 and a dowel pin 690 (FIGS. 10 and 11). Advantageously, the depth gauge assembly 600 permits an operator to quickly and accurately change the depth of cut DOC of the dermatome from essentially 0.000 in. (no depth of cut of skin tissue ST—shown schematically in FIG. 21) to 0.045 in. (full depth of cut of skin tissue ST—shown schematically in FIGS. 12 and 20). Obviously, the range of depth of cut DOC may be changed based on the configuration of the depth gauge assembly 600 and the present invention is not limited to the exemplary depth of cut range set forth herein. As changing the depth of cut DOC of the dermatome 100 is accomplished by rotation of the depth adjustment knob 650, the depth of cut DOC is infinitely variable between the 0.000 in. and 0.045 in. endpoints. That is, the operator can precisely dial in an exact desired depth of cut DOC for the dermatome 100.

Depth Gauge Cylindrical Support 602

As best seen in FIGS. 8 and 10-12, the depth gauge cylindrical support 602 extends from and is supported by the V-shaped rib 222 of the upper interface region 220 of the forward interface portion 206 of the frame body 202. The depth gauge support 602, in one exemplary embodiment, is generally cylindrical and includes an upper end 604 and an axially spaced apart lower end 606. The depth gauge cylindrical support 602 defines an axially extending central opening 608 (FIG. 12) passing through the support 602. A radially outwardly extending flange 610 is disposed at the upper end 604 of the depth gauge cylindrical support 602. As can be seen in FIG. 10, the flange 610 includes a first smaller opening 612 that is axially aligned with the central opening 608 and a second larger opening 614 that is connected to but offset from the first smaller opening 612. A radially outwardly extending slot 616 (FIG. 12) is disposed between the flange 610 and the central opening 608 of the depth gauge cylindrical support 602.

An upper surface 618 of the flange 610 includes indicia or markings 619 (FIG. 10) representing gradations for the depth of cut DOC of the dermatome 100 as the depth adjustment knob 650 is rotated. Specifically, each of the smaller gradations represent a change in the set depth of cut DOC of 0.001 in., while the larger gradations represent a change in the set depth of cut of 0.005 in. The indicia 619 facilitate precise setting of the dermatome depth of cut DOC by the operator.

The depth gauge shaft 640 is received in the axially extending central opening 608 of the cylindrical support 602. The depth gauge shaft 640 is supported by the cylindrical support 602 for axial movement with respect to the cylindrical support 602. Specifically, the cylindrical support 640 contacts and supports the depth gauge shaft 640 over an axial length labeled AL in FIG. 12. In one exemplary embodiment, the axial length AL of the cylindrical support 602 is approximately 1.05 in., while the overall axial length of the cylindrical support 602 extending between the upper end 604 of the cylindrical support 602 and the lower end 606 of the cylindrical support 602 is approximately 1.25 in.

Depth Gauge 620

Figure 12:
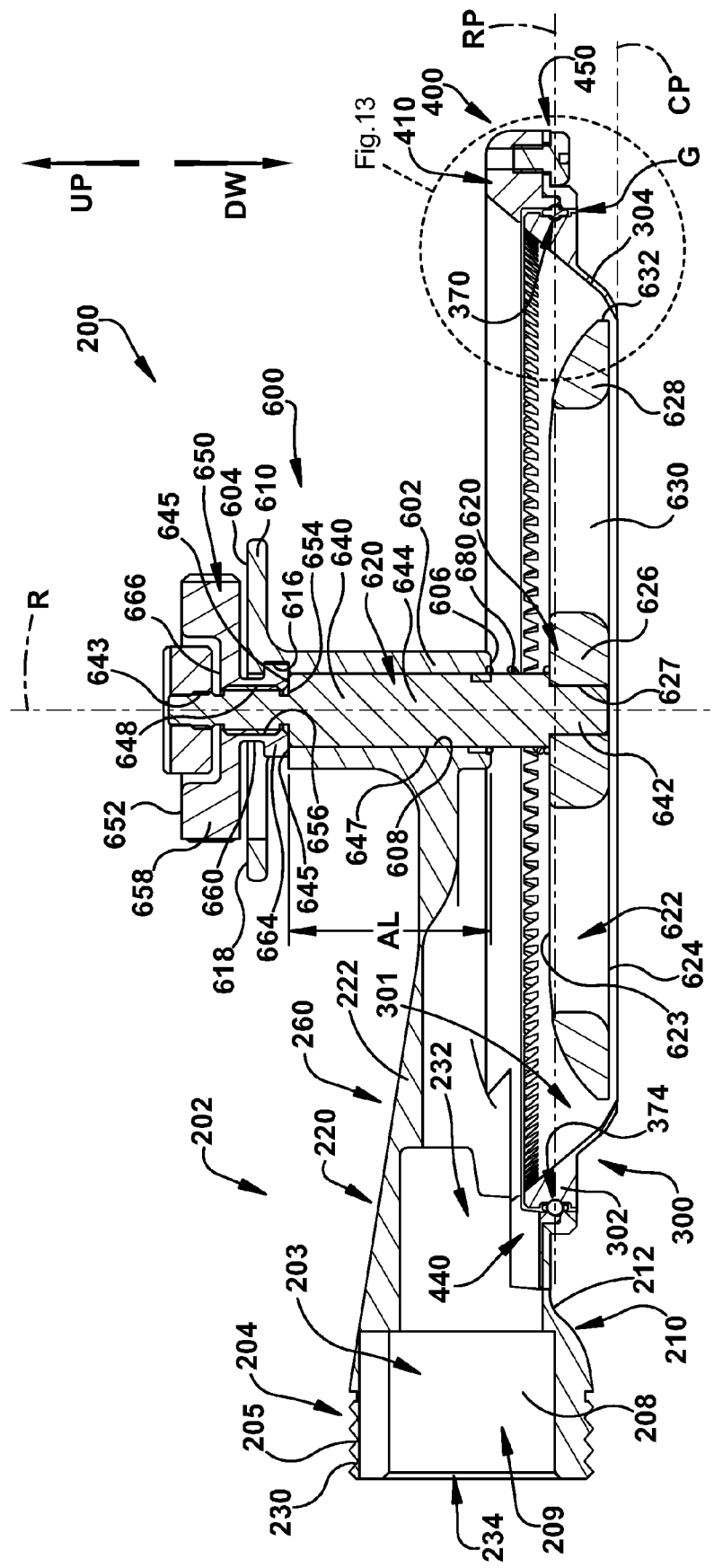
FIG. 12 is a schematic section view of the head assembly of FIG. 8 as viewed from a plane indicated by the line 12-12 in FIG. 9.

The depth gauge 620 is supported by the depth gauge support 602 and includes the depth gauge plate 622 and the depth gauge shaft 640. As can be seen in FIG. 12, the depth gauge shaft 640 and the depth gauge plate 622 are substantially concentric with the knife blade axis of rotation R. The depth gauge 20 is adjustable to move axially along the axis of rotation R, that is, the depth gauge moves axially respect to the depth gauge support 602 and with respect to the cutting plane CP of the rotary knife blade 300. Movement of the depth gauge plate 622 with respect to the cutting plane CP of the rotary knife blade 300 changes the dermatome depth of cut DOC. The depth gauge plate 622 and a portion of the depth gauge shaft 640 extend into the interior region 301 of the rotary knife blade 300. The depth gauge 620 also includes the stop ring 670 which is affixed to an upper end of the depth gauge shaft 640 and moves with the shaft 640 axially to limit downward movement of the depth gauge 620. That is, the stop ring 670 insures that the minimum depth of cut DOC is 0.000 in., as opposed to the depth gauge plate 622 moving in a downward direction DW to a negative depth of cut DOC position.

Depth Gauge Plate 622

The depth gauge plate 622 is generally disc-shaped and includes an upper surface 623 and an axially spaced apart generally planar lower surface 624. The depth gauge plate 622 includes a central body 626 and a radially outwardly spaced annular rim 628. The central body 626 and the annular rim 628 are connected by three radially extending ribs 630. The central body 626 of the depth gauge plate 622 includes a central opening 627 that receives a lower connecting end 642 of the depth gauge shaft 640 to secure the depth gauge plate 622 to the depth gauge shaft 640.

The depth gauge plate 622 includes a radially outer peripheral surface 632. A lower edge region 634 of the depth gauge plate 622 is an intersection region between the planar lower surface 624 of depth gauge plate 622 and outer peripheral surface 632 of depth gauge plate. At any axial position of the depth gauge plate 622, the lower edge region 634 of the depth gauge plate 622 is the closest portion of the depth gauge 620 to the cutting edge 360 of the rotary knife blade 300. The lower edge region 634 is nearly (but not exactly) axially aligned with the rotary knife blade cutting edge 360. As such, an axial distance between the lower edge region 634 of the depth gauge plate 622 and the cutting edge 360 of the rotary knife blade 300 determines the depth of cut DOC of the dermatome 100. Recall that the cutting edge 360 defines the cutting plane CP of the rotary knife blade 300, therefore, stated another way, an axial distance AD (FIG. 18) between the lower edge region 634 of the depth gauge plate 622 and the cutting plane CP of the rotary knife blade 300 determines the depth of cut DOC of the dermatome 100.

Depth Gauge Shaft 640

As best seen in FIG. 12, the depth gauge shaft 640 is generally cylindrical and includes the lower connecting end 642 that is received in the central opening 627 of the central body 626 of the depth gauge plate 622 to attach the depth gauge shaft 640 and the depth gauge plate 622. The depth gauge shaft 640 includes a reduced diameter threaded upper portion 643. When the depth gauge shaft 640 is inserted into the axially extending central opening 608 of the depth gauge support 602, first, the second threaded portion 648 of the depth gauge shaft 640 is threaded into the central threaded opening 656 of the depth adjustment knob 650, then, the stop ring 670 is threaded onto the upper threaded portion 643 of the depth gauge shaft 640 to secure the depth gauge shaft 640 (and attached depth gauge plate 622) to the depth gauge support 602. When it is desired to remove the depth gauge shaft 640 from the depth gauge support 602, the stop ring 670 is unthreaded and removed from the depth gauge shaft 640 and the depth gauge shaft 640 is unthreaded from the central threaded opening 656 of the depth adjustment knob 650, allowing the depth gauge shaft 640 to drop out of the depth gauge support 602 for cleaning/sterilization purposes.

The depth gauge shaft 640 includes an outer surface 647 defining an axially extending slot 646. The axially extending slot 646 receives the dowel pin 690 (FIGS. 10 and 11) that passes through a radial opening 617 in the depth gauge cylindrical support 602 to prevent relative rotation between the depth gauge shaft 640 as supported within the cylindrical support 602. The depth gauge shaft 640 also includes a second threaded portion 648 that is disposed below the threaded upper portion 643. The second threaded portion 648 of the depth gauge shaft 640 is threadedly received in a threaded central opening 656 of the depth adjustment knob 650.

Depth Adjustment Knob 650

The depth adjustment knob 650 includes an upper end 652 and a lower end 654. The depth adjustment knob 650 includes a central threaded opening 656 which is threaded onto the second threaded portion 648 of the depth gauge shaft 640. The dowel pin 690 and the axially extending slot 646 of the depth gauge shaft 656 allow the depth gauge shaft 656 to move axially within the axially extending central opening 608 of the depth gauge cylindrical support 602. The depth adjustment knob 650, when rotated, drives the depth gauge shaft 656 upward or downward with respect to the depth gauge cylindrical support 602.

The depth adjustment knob 650 includes a central stem 660, an enlarged upper head 658 above the stem 660, and an enlarged lower head 664 below the stem 660. The enlarged lower head 664 is sized to pass though the larger offset opening 614 of the flange 610 of the depth gauge cylindrical support 602 and is received in the slot 616 of the cylindrical support 602 to restrain axial movement between the depth adjustment knob 650 and the cylindrical support 602. The enlarged upper head 658 of the depth adjustment knob 650 includes a recessed contact surface 666 that is configured to be contacted by a lower surface 674 of the stop ring 670. An upper surface of the enlarged upper head 658 will include an arrow or some other marking that can be aligned with the indicia 619 marked on the upper surface 618 of the cylindrical support flange 610 to aid the operator in adjusting and setting the depth of cut DOC of the dermatome 100.

As the depth adjustment knob 650 is rotated by the operator, the dowel pin 690 extending into the axially extending slot 646 prohibits the depth gauge shaft 640 and the depth gauge plate 622 from rotating with the depth adjustment knob 650. The dowel pin/axially extending slot configuration 690/646 does permit the depth gauge shaft 640 to move up and down axially within the depth gauge cylindrical support 602 to change the depth of cut DOC of the dermatome 100. However, the depth gauge shaft 640 is constrained from rotating with the depth adjustment knob 650 by virtue of the dowel pin 690 fitting into the axially extending slot 646. The depth gauge shaft 640 is constrained from rotating with the depth adjustment knob 650 and the knob 650 is constrained from axial movement by virtue of the enlarged lower head 664 of the knob 664 being confined in the radially outwardly extending slot 616 of the depth gauge cylindrical support 602. Thus, rotation of the depth adjustment knob 650 drives the depth gauge shaft 640 axially in the upward direction UP or the downward direction DW with respect to the depth gauge cylindrical support, depending on the direction of rotation of the depth adjustment knob 650.

When depth adjustment knob 650 is rotated to move the depth gauge 620 in the downward direction DW, the dowel pin 690 prevents rotation of the depth gauge 620 with the depth adjustment knob 650. Thus, depending on the direction of rotation of the depth adjustment knob 650, the depth gauge 620 will be moved in the upward direction UP or the downward direction DW with respect to the cylindrical support 602 and the rotary knife blade 300. Movement of the depth gauge 620 in the upward direction is limited by contact between the upper surface 645 of the central portion 644 of the depth shaft 640 and a lower end 654 of the depth adjustment knob 650 such that a maximum depth of cut DOC is 0.045 in. This maximum depth of cut DOC configuration is shown in FIGS. 12 and 13 and is referred to as the fully open position of the dermatome 100.

Figure 21:
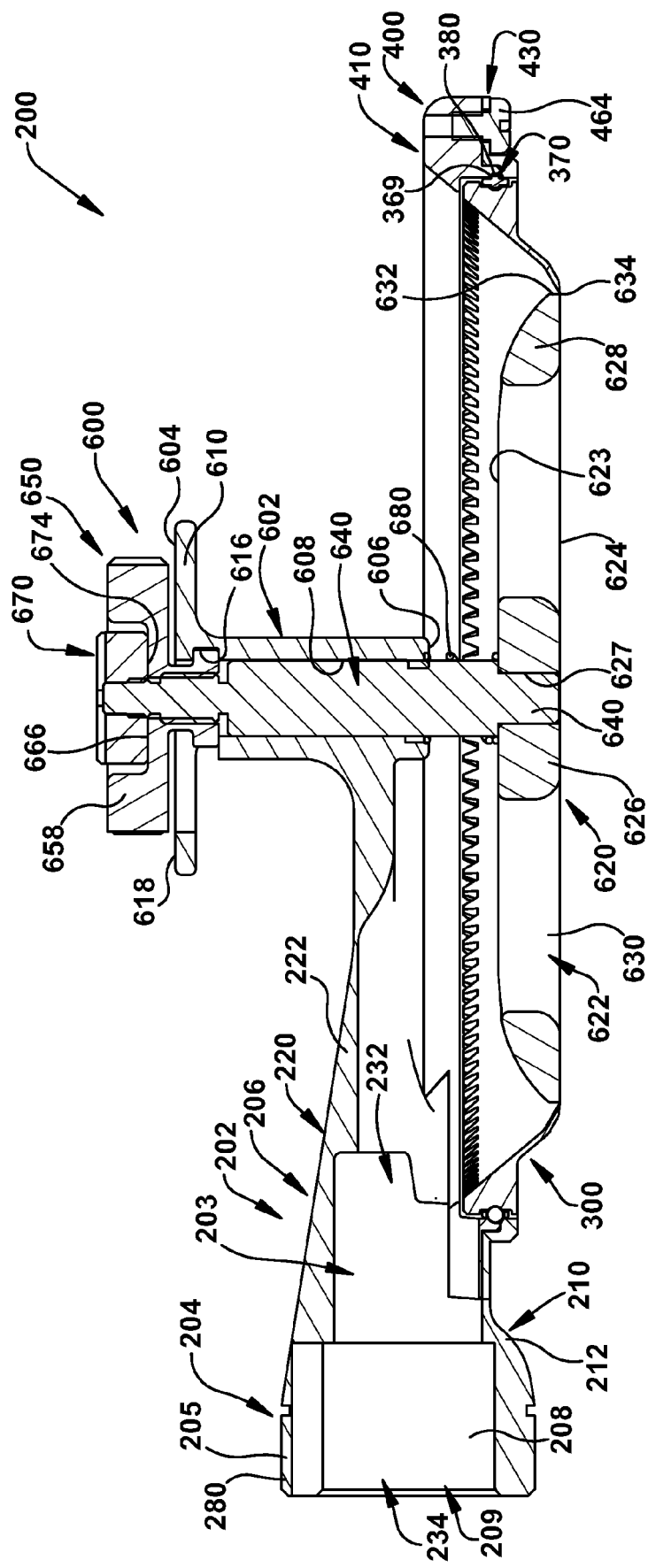
FIG. 21 is a schematic section view of a portion of the dermatome of FIG. 1 showing the depth gauge assembly in a fully closed position providing a minimum depth of cut of the dermatome.

Movement of the depth gauge in the downward direction DW is limited by contact between the lower surface 674 of the stop ring 670 and the recessed contact surface 666 of the enlarged upper head 658 of the depth adjustment knob 650. This minimum depth of cut DOC configuration is shown in FIG. 21 and is referred to as the fully closed position of the dermatome 100. The biasing spring 680 is trapped between the central body 626 of the depth gauge plate 622 and the lower end 606 of the depth gauge cylindrical support 602 to bias the depth gauge 620 to the fully closed position.

In one exemplary embodiment, the handle assembly 110 may be fabricated of plastic or other material or materials known to have comparable properties and may be formed by molding and/or machining. The attachment assembly 120, the frame body 202, and the depth gauge assembly 600 may be fabricated of aluminum or stainless steel or other material or materials known to have comparable properties and may be formed/shaped by casting and/or machining The rotary knife blade 300 and the blade housing assembly 400 may be fabricated of a hardenable grade of alloy steel or a hardenable grade of stainless steel, or other material or materials known to have comparable properties and may be formed/shaped by machining, forming, casting, forging, extrusion, metal injection molding, and/or electrical discharge machining or another suitable process or combination of processes.

Operation of Dermatome 100

FIGS. 17-19 schematically illustrate use of the dermatome 100 of the present disclosure for excising a layer skin tissue ST in a donor grafting region GR and, in particular, obtaining a thin type, split thickness skin graft wherein a depth of a layer of skin tissue being excised from the graft region GR is on the order of 0.005 in. to 0.012 in. FIG. 17 schematically shows the initial incision into an upper layer or surface SST of the skin tissue ST with the dermatome 100. Recall that in the illustrated and exemplary embodiment, the cutting angle CA of the rotary knife blade 300 is approximately 30°. In making the incision into the skin tissue surface SST, the angle of the dermatome 100 is manipulated such that a skin tissue cutting angle STCA is shallower than the cutting angle CA of the knife blade 300. In one exemplary embodiment, the cutting angle of the inner wall 310 in the lower region 359 of the blade section 304 adjacent the cutting edge 360 with respect to the surface SST of the skin tissue ST being excised lower is approximately 15°. Thus, the skin tissue cutting angle STCA (approximately) 15° is less than the blade cutting angle CA. (approximately 30°). Thus, the outer wall 418 of the blade housing 410 is not vertical, but rather is slightly angled downwardly toward the skin tissue ST.

FIG. 18 schematically shows the cutting or excising of the skin tissue ST. As the actuated dermatome 100 moves along a path of travel PT, the dermatome 100 produces an excised section of skin tissue EST which flows along the inner wall 365 and through the central interior region 301 of the rotary knife blade 300 and slanted or frustoconical upper portion of the blade housing inner wall 416. The slanted upper portion of the blade housing inner wall 416 generally continues the frustoconical inner wall 365 of the rotary knife blade 300. The excised section of skin tissue EST is a flexible, generally rectangular piece or section of skin tissue ST that exits the dermatome 100 by moving or "flopping" (since the skin tissue is flexible or flaccid) over the upper end or wall 412 of the blade housing 410. As schematically depicted in FIG. 18, a longitudinal extent LE of the excised section EST, a depth or thickness of excised skin tissue DEST should be uniform and should conform in thickness to the depth of cut DOC set by the operator of the dermatome 100. In moving along the path of travel PT, the angle of the dermatome 100 is held relatively flat, that is, the skin tissue cutting angle STCA is approximately equal to the rotary knife blade cutting angle CA. The skin tissue cutting angle STCA and the rotary knife blade cutting angle CA both being approximately 30°. Advantageously, the operator need only keep the cutting plane CP of the dermatome 100 flush or flat against the surface SST of the skin tissue ST as the dermatome 100 is moved along its path of travel PT to excise a section of skin tissue EST. Thus, with the dermatome 100 of the present disclosure, undertaking a successful excising procedure which results in an excised skin tissue section EST having a consistent and desired depth or thickness is more straightforward and less dependent on operator skill level.

FIG. 19 schematically shows the termination of the excising procedure, that is, ending of the cutting of the skin tissue ST in the grafting region GR with the dermatome 100. Like with the incision, the dermatome 100 is manipulated by the operator to have a shallower skin tissue cutting angle STCA of approximately 15°. This shallow skin tissue cutting angle STCA causes the blade 300 to tend to move upwardly through the skin tissue SK. If necessary, the operator can slightly wiggle the dermatome 100 in a side-to-side motion to facilitate the rotary knife blade in cutting upwardly and through the surface of the skin tissue ST. When the blade 300 comes through or emerges from the surface SST of the skin tissue ST, this terminates the cut or excision and determines or fixes the total longitudinal extent LE of the excised skin tissue section EST.

FIG. 20 schematically depicts the excising of a thicker layer of skin tissue ST with the dermatome 100. Here, the dermatome 100 is used for obtaining a full thickness skin graft from a donor graft region GR wherein a depth of a layer DEST of skin tissue EST being excised from a donor graft region GR is on the order of 0.030 in. to 0.043 in.

It should be understood by one of ordinary skill in the art that an apparatus described as the dermatome 100 could be adapted and utilized for a wide variety of other medical applications including, but not limited to, soft tissue harvesting and/or removal, bone harvesting and/or removal, dermatological treatment needs, and other medical procedures.

Second Exemplary Embodiment—Power Operated Dermatome 1000

Figure 22:
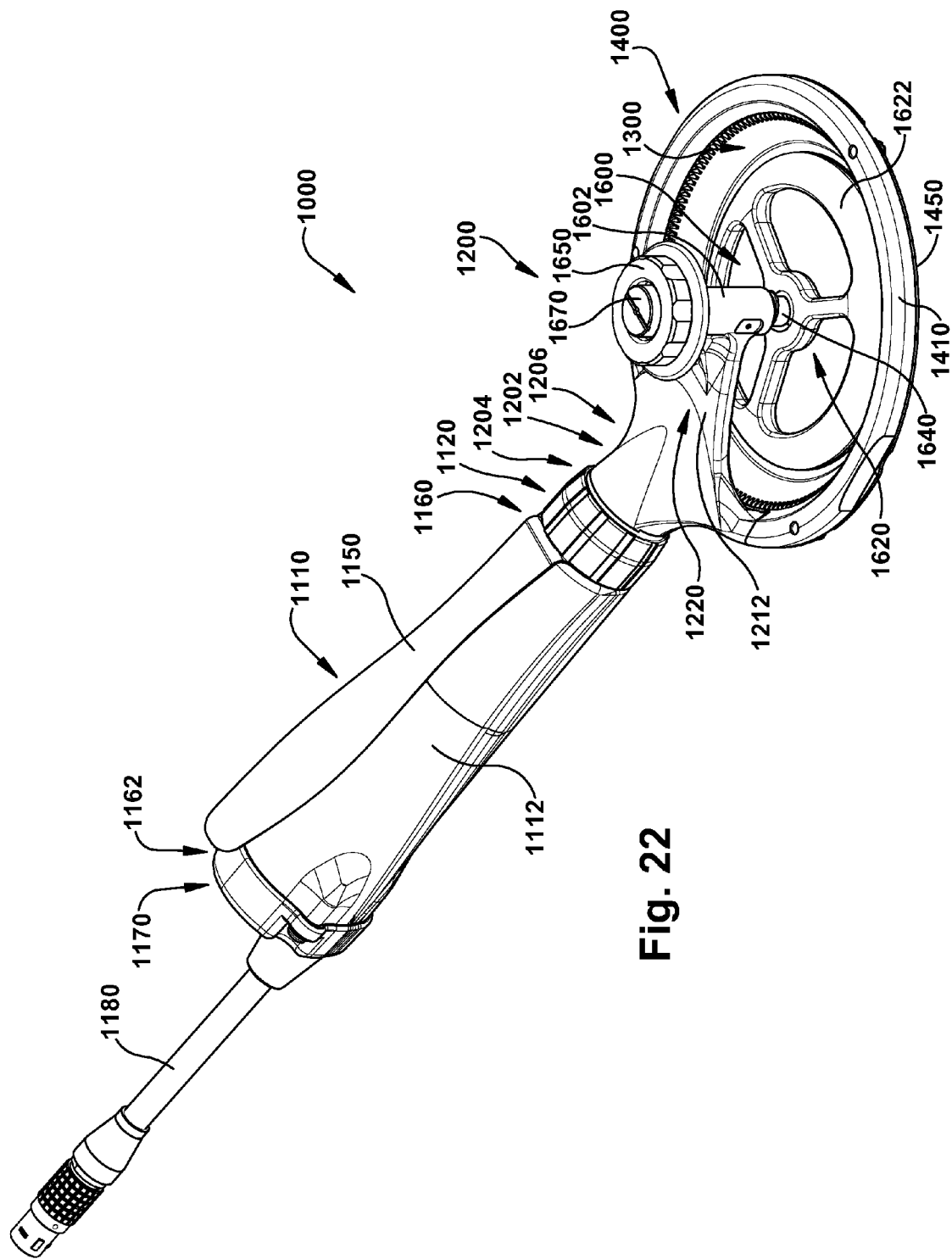
FIG. 22 is a schematic perspective view of a second exemplary embodiment of a hand-held, power operated dermatome of the present disclosure including a handle assembly and a head assembly including a rotary knife blade and a depth gauge assembly extending into a central, interior region defined by the rotary knife blade.
Figure 23:
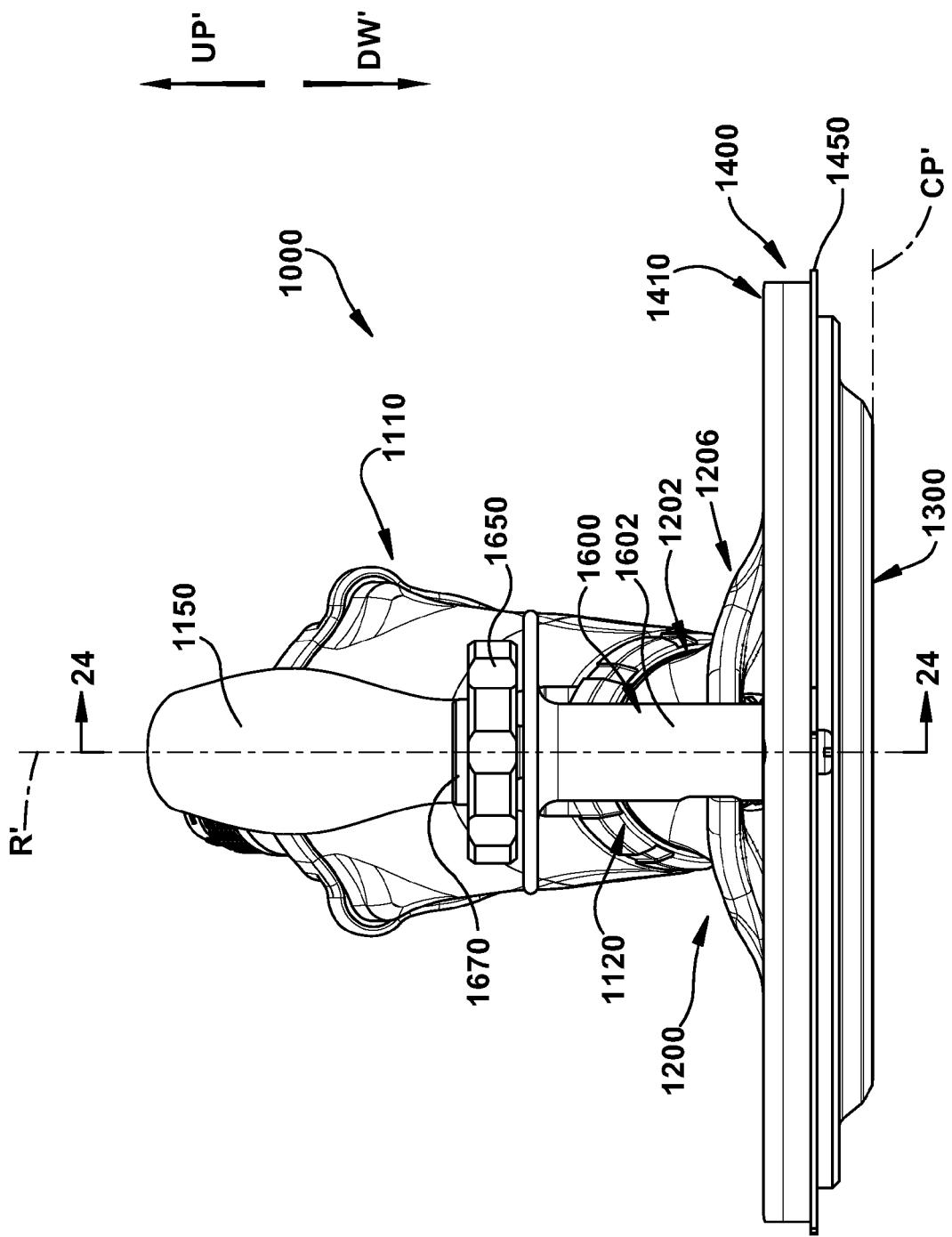
FIG. 23 is a schematic front elevation view of the power operated dermatome of FIG. 22.
Figure 24:
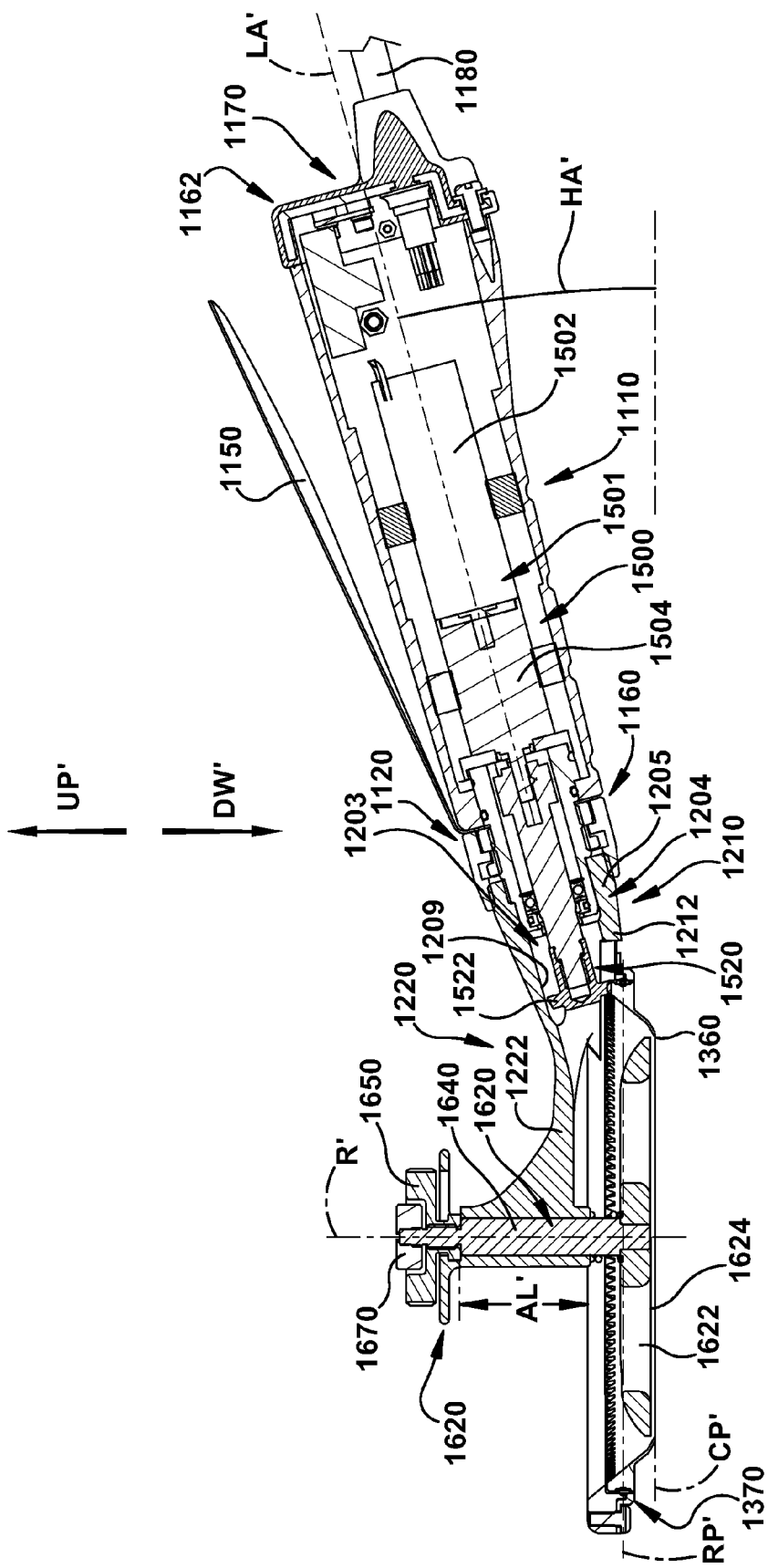
FIG. 24 is a schematic longitudinal section view of the power operated dermatome of FIG. 22, as viewed along a longitudinal axis LA' of the handle assembly of the dermatome and as seen from a plane indicated by the line 24-24 in FIG. 23.
Figure 25:
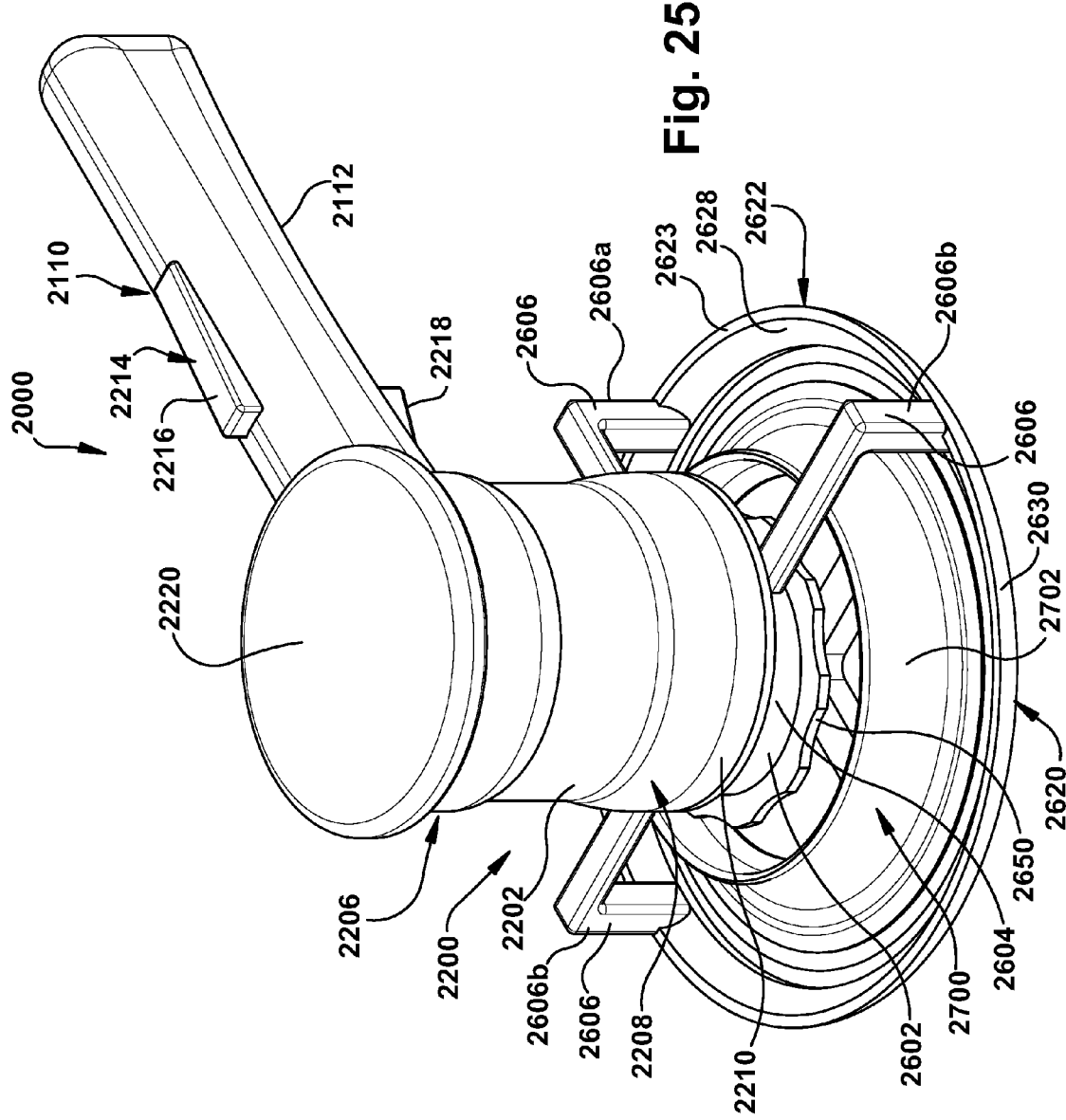
FIG. 25 is a schematic top perspective view of a first exemplary embodiment of a hand-held, power operated debridement tool including a head assembly having a disk-shaped rotary knife blade, a skin guide assembly and a depth gauge assembly.
Figure 26:
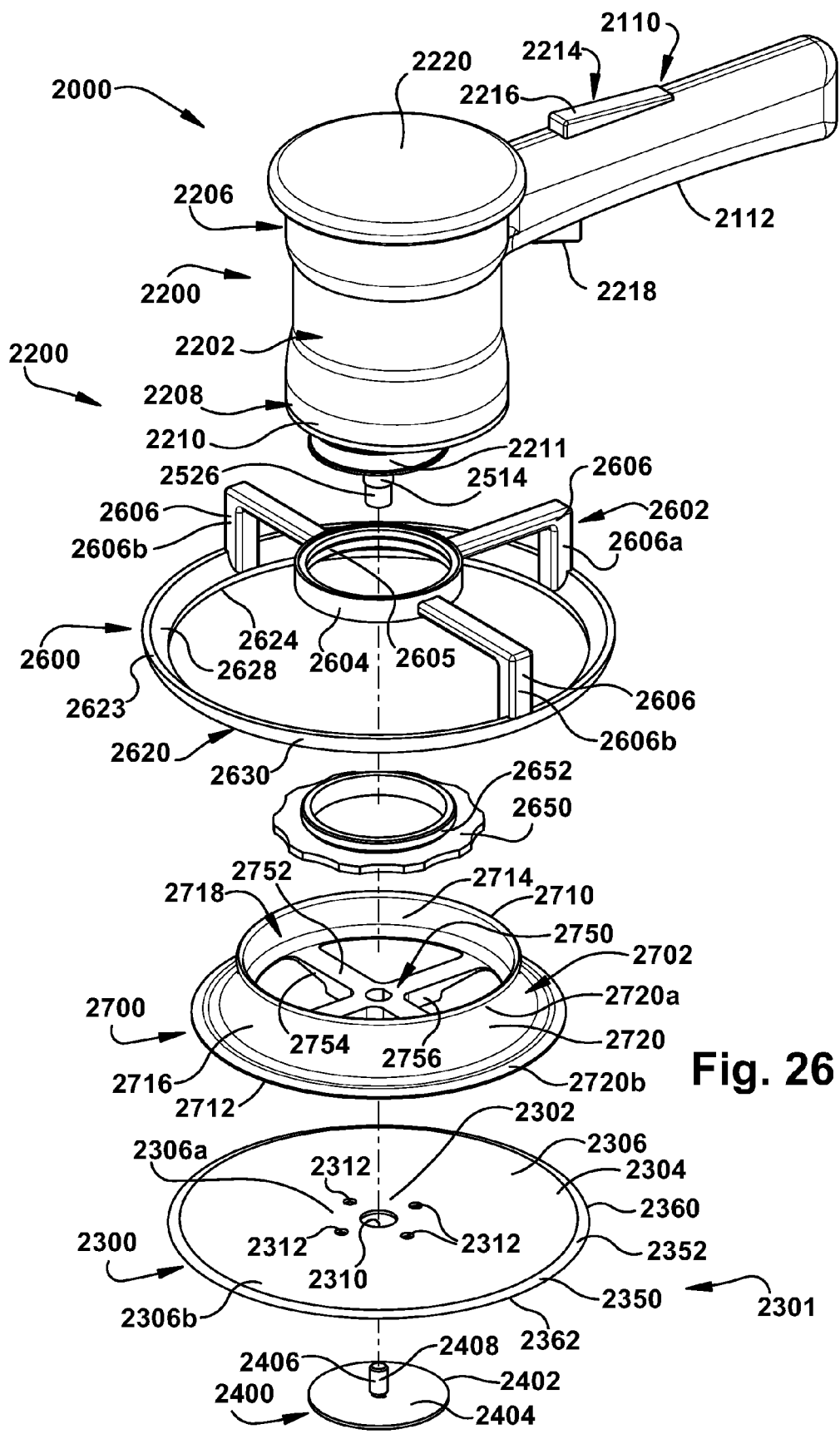
FIG. 26 is a schematic exploded top perspective view of the power operated debridement tool of FIG. 25.
Figure 27:
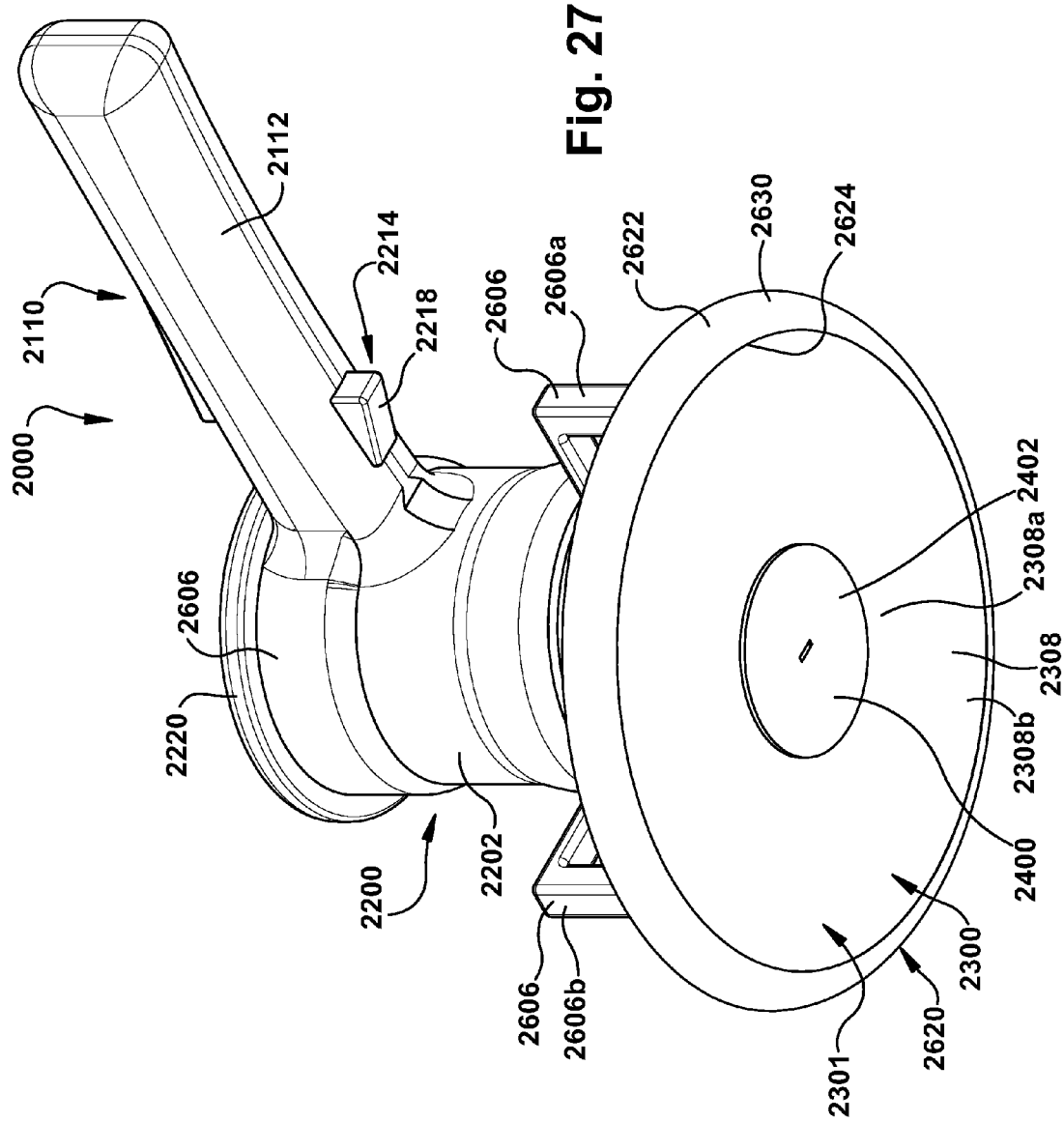
FIG. 27 is a schematic bottom perspective view of the power operated debridement tool of FIG. 25.
Figure 28:
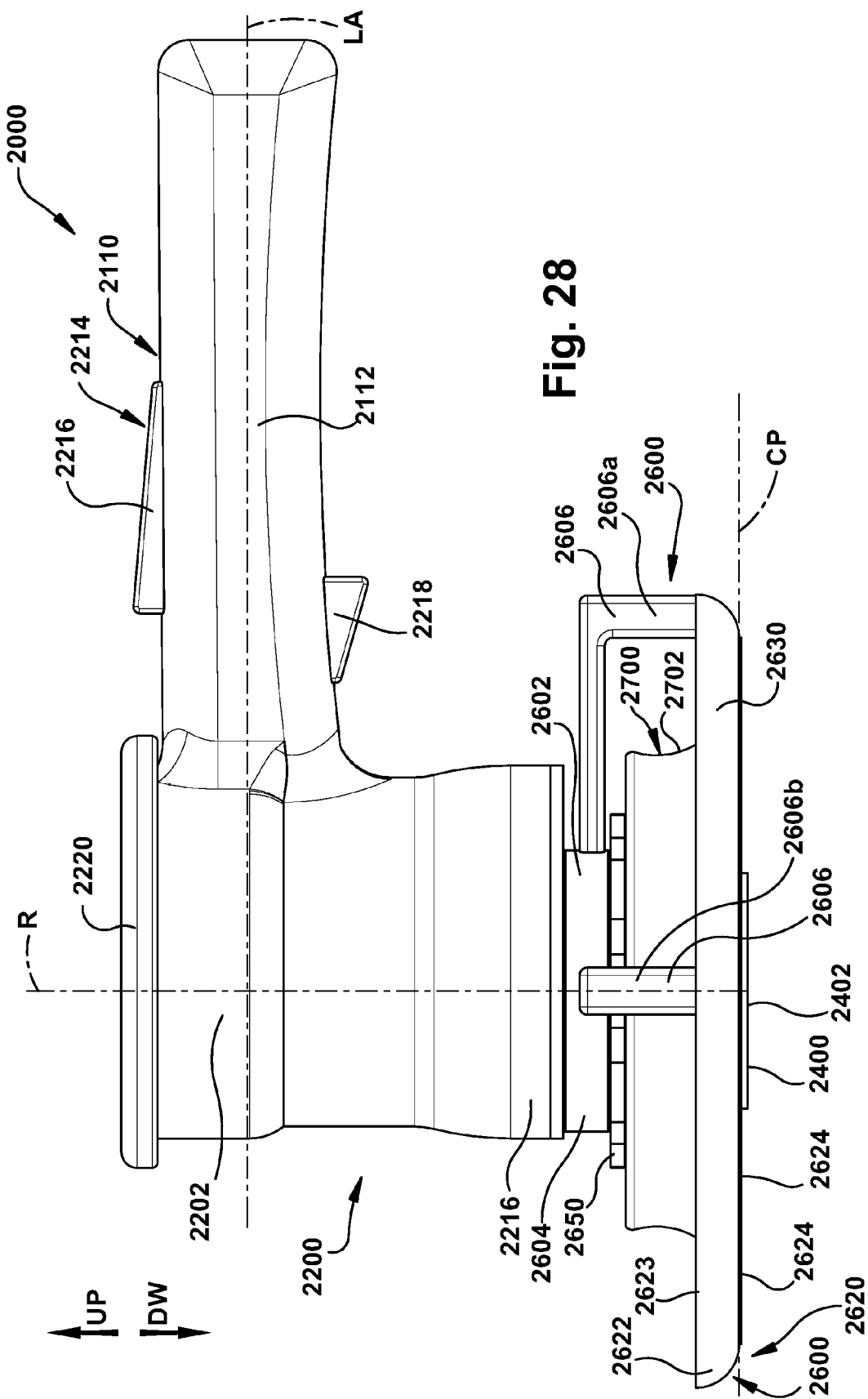
FIG. 28 is a schematic side elevation view of the power operated debridement tool of FIG. 25.
Figure 29:
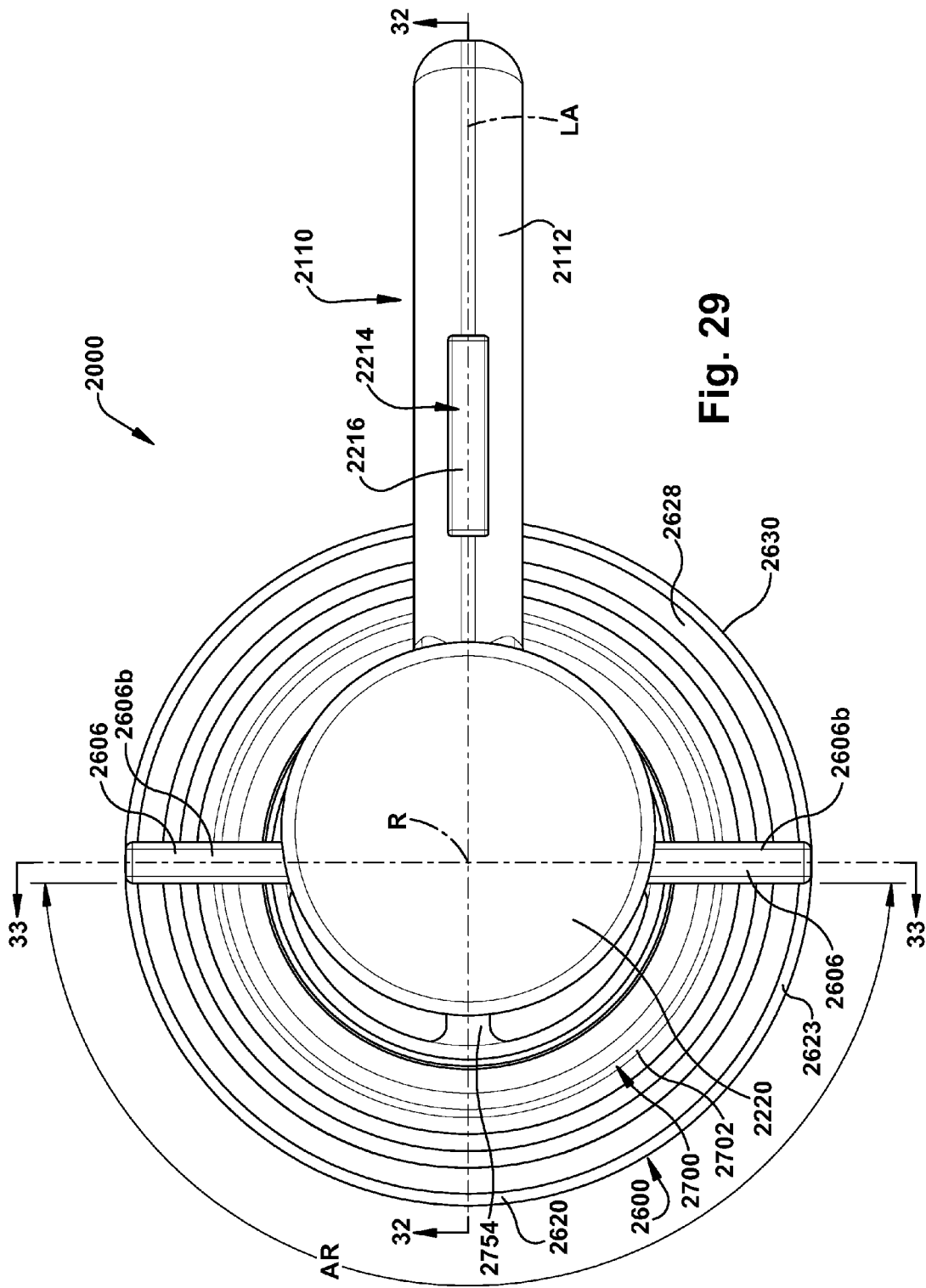
FIG. 29 is a schematic top plan view of the power operated debridement tool of FIG. 25.

A second exemplary embodiment of a hand-held, power operated dermatome of the present disclosure is schematically shown at 1000 in FIGS. 22-24. The power operated dermatome 1000 is similar in configuration and operation to the power operated dermatome 100, as described above, and the description of the dermatome 100, as set forth above, is referenced and incorporated herein with respect to the dermatome 1000.

The power operated dermatome includes an elongated handle assembly 1110, similar to the handle assembly 110, and a head assembly 1200, similar to the head assembly 200, extending from a forward or distal end 1160 of the handle assembly 1110. The handle assembly 1110 includes a handle 1112 and an actuation lever 1150 and extends between the distal end 1160 adjacent the head assembly 1200 and a proximal end 1162. A cover 1170 at the proximal end 1162 of the handle assembly 1110 is coupled to an air hose 1180 which provides motive power to the drive assembly 1500, similar to the drive assembly 500, of the dermatome 1000. An attachment assembly 1120, similar to the attachment assembly 120, releasably affixes the head assembly 1200 to the handle assembly 1110.

The dermatome 1000 includes the drive assembly 1500, similar to the drive assembly 500, including a drive motor assembly 1501, similar to the drive motor assembly 501, and a gear train 1520, similar to the gear train 520. The gear train 1520, in one exemplary embodiment, comprises a pinion gear 1522, similar to the pinion gear 522.

The head assembly 1200 includes a frame body or frame housing 1202, similar to the frame body 202, a rotary knife blade 1300, similar to the rotary knife blade 300, a blade housing assembly 1400, including a blade housing 1410 and a blade lock ring 1450, similar to the blade housing assembly 400, and a depth gauge assembly 1600, similar to the depth gauge assembly 600. The frame body 1202 includes a rearward handle attachment portion 1204 comprising a cylindrical body 1205 and a forward interface portion 1206. The frame body 1202 includes a gearbox housing 1203 defined by a throughbore 1209 through the frame body 1202. The gear train 1520 is supported within the gearbox housing 1203. The forward interface portion 1206 of the frame body 1202 includes a lower interface region 1210 that extends or transitions between the rearward handle attachment portion 1204 and the annular blade housing 1410 of the blade housing assembly 1400. The lower interface region 1210 includes a generally Y-shaped support 1212. The forward interface portion 1206 of the frame body 1202 also includes an upper interface region 1220 that extends or transitions between the rearward handle attachment portion 1204 and a central cylindrical support 1602 of the depth gauge assembly 1600. The upper interface region 1220 includes a generally V-shaped rib 1222 that converges proceeding toward and has a vertex generally at the central cylindrical support 1602.

The depth gauge assembly 1600 includes the depth gauge central cylindrical support 1602, similar to the central cylindrical support 602, that extends from the V-shaped rib 1222 of the upper interface region 1220 of the forward interface portion 1206 of the frame body 1202. The depth gauge assembly 1600 also includes a depth gauge 1620, similar to the depth gauge 620. The depth gauge 1620 includes the depth gauge shaft 1640 and a depth gauge plate 1622. The depth gauge assembly 1600 further includes a depth adjustment knob 1650 and a stop ring 1670, similar to the depth adjustment knob 650 and stop ring 670.

The rotary knife blade 1300 is supported for rotation about an axis of rotation R', similar to the axis of rotation R, by the blade housing assembly 1400. The rotary knife blade 1300 includes a cutting edge 1360 which defines a cutting plane CP', similar to the cutting plane CP, and further includes a continuous rolling bearing structure 1370, similar to the continuous rolling bearing structure 370, which defines a rotational plane RP' of the blade 1300, similar to the rotational plane RP of the blade 300. The blade housing assembly 1400 includes an annular blade housing 1410, similar to the blade housing 400, and a blade lock ring 1450, similar to the blade lock ring 1450, which is releasably affixed to the blade housing 1410 to trap and secure the rotary knife blade 1300 for rotation with respect to the blade housing assembly 1400.

As can best be seen in FIG. 24, the handle assembly 1110 extends along a longitudinal axis LA' which is canted or angled upwardly at a handle angle HA' with respect to the cutting plane CP' and the rotational plane RP' of the rotary knife blade 1300 and with respect to the planar lower surface 1624 of the depth gauge plate 1622. That is, a proximal end 1162 of the handle assembly 1110 is spaced higher in an upward direction UP' above the cutting plane CP' of the rotary knife blade 1300 or the planar lower surface 1624 of the depth gauge plate 1622 than is the distal end 1160 of the handle assembly 1110. In the dermatome 100, the handle angle was substantially 0°. In one exemplary embodiment of the dermatome 1000, the handle angle HA' with respect to the cutting plane CP' or the rotational plane RP' of the rotary knife blade is in a range of 10°-20° and, more particularly, in one exemplary embodiment, the handle angle HA' may be approximately 15°. The handle angle HA' advantageously provides for ease of operation and clearance for the fingers of the operator. Recall that with the dermatomes 100, 1000 of the present disclosure, when excising a layer of skin tissue ST, the operator generally keeps the cutting plane CP' of the dermatome 1000 flush or flat against the surface SST of the skin tissue ST as the dermatome 1000 is moved along its path of travel PT. The upward angle HA' of the handle assembly 1110 of the dermatome 1000 facilitates keeping the cutting plane CP' of the dermatome head assembly 1200 flush or flat against the surface SST of the skin tissue ST during an excising procedure.

The rearward handle attachment portion 1204 of the frame body 1202 of the dermatome 1000 is slightly different than the corresponding rearward handle attachment portion 204 of the frame body 202 of the dermatome 100. To match the upward canted or tilted handle angle HA' of the handle assembly 1100, the rearward handle attachment portion 1204 is also angled upwardly to match the handle angle of the handle assembly 1100. This can best be seen in FIG. 24. Similarly, the gear train 1520 of the head assembly 1200 is modified accordingly to account for the different angle of contact between the pinion gear 1522 and the set of gear teeth of the rotary knife blade 1300.

Another difference between the dermatomes 100, 1000 involves an axial length of the respective depth gauge central cylindrical supports 602, 1602. To provide additional laterally stability and accuracy to the depth gauge plate 1622, in the dermatome 1000, an axial length AL' was increased slightly. Recall that the axial length AL of the cylindrical support 602 of the dermatome 100, in one exemplary embodiment, was approximately 1.05 in., while the overall axial length of the cylindrical support 602 extending between the upper end 604 of the cylindrical support 602 and the lower end 606 of the cylindrical support 602 was approximately 1.25 in. In one exemplary embodiment of the dermatome 100, the axial length AL' of the cylindrical support is approximately 1.30 in., while the overall axial length of the cylindrical support 1602 between the upper and lower ends is approximately 1.50 in.

Alternate Embodiment—Power Operated Debridement Tool 2000

An alternate exemplary embodiment of a hand-held, power operated debridement tool of the present disclosure is schematically shown at 2000 in FIGS. 25-33. In contrast to the power operated dermatomes 100, 1000 discussed above, the power operated debridement tool 2000 includes a disk-shaped rotary cutting blade or disk knife blade 2300 having a cutting edge 2360 at an outer peripheral edge 2362 of a blade section 2304 of the disk knife blade 2300. The power operated debridement tool 2000 is alternately referred to herein as a disk debridement tool 2000.

The disk debridement tool 2000 is suited for various medical procedures described in connection with the power operated dermatomes 100, 1000 such as split-thickness and full-thickness skin grafting, skin debriding, lesion/tumor removal, etc. In one exemplary embodiment, the configuration of the disk knife blade 2300 of the disk debridement tool 2000 is such that a cutting angle CA (FIGS. 35 and 36) of the disk knife blade 2300 is on the order of 5-10°. Thus, the cutting angle CA of the disk knife blade 2300 is much smaller or shallower than, for example, the cutting angle CA of rotary knife blade 300 of the power operated dermatome 100, which, as described previously, is on the order of 30°. Additionally, since the cutting angle CA of the disk debridement tool 2000 is on the order of 5-10°, when used for cutting a layer of skin tissue ST, a skin tissue cutting angle STCA of the disk debridement tool 2000 is correspondingly smaller or shallower than the skin tissue cutting angle STCA of the power operated dermatome 100. That is, the skin tissue cutting angle STCA of the disk debridement tool 2000 is on the order of approximately 5-10° versus the vs. the skin tissue cutting angle STCA of approximately 30° for the power operated dermatome 100. For certain procedures, the shallower cutting angle CA of the disk debridement tool 2000 is particularly advantageous and suitable. The configuration of the disk debridement tool 200 may allow for greater ease of cutting or trimming a layer the skin tissue ST to be excised, allow easier manipulation and control of the disk debridement tool 2000, and/or provide for greater visibility of the grafting region GR in the area where the cutting edge 2360 cuts or trims the skin tissue ST to produce the excised skin tissue layer EST.

As can best be seen in FIGS. 25-33, the disk debridement tool 2000 includes a head assembly 2200, including a generally cylindrical frame body or frame housing 2202, a handle assembly 2110, extending generally orthogonally from the head assembly 2200 and grasped by an operator to actuate and manipulate the disk debridement tool 2000 using a single hand. The disk debridement tool 2000 additionally includes a drive assembly 2500 which, when actuated, rotatably drives the disk knife blade 2300 about a central axis of rotation R. The description of the power operated dermatomes 100, 1000, as set forth above, are referenced and incorporated herein with respect to the disk debridement tool 2000.

Head Assembly 2200

Figures 36, 37:
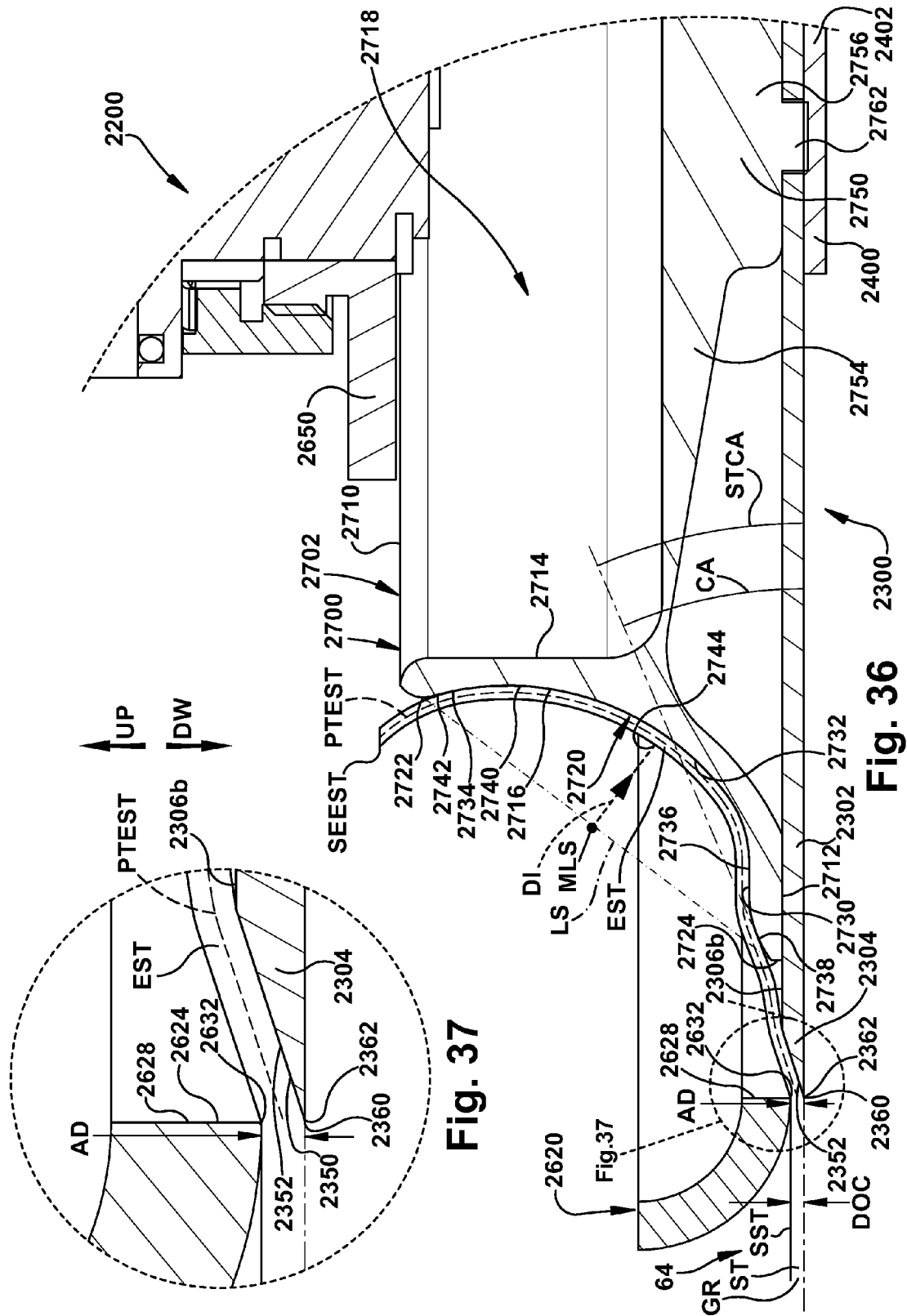
FIG. 36 is a schematic section view of the power operated debridement tool of FIG. 25 as used to debride or excise a layer of skin tissue, illustrating the flow of the debrided skin tissue along an annular skin guide of the skin guide assembly of the debridement tool.
FIG. 37 is a schematic enlarged section view of a portion of the head assembly shown in FIG. 36 that is within a dashed circle labeled FIG. 37 in FIG. 36.

The head assembly 2200 of the disk debridement tool 2000 comprises the frame housing or frame body 2202 and a disk knife blade assembly 2301, which includes the disk knife blade 2300. The head assembly 2200 also includes a skin guide assembly 2700. The skin guide assembly 2700 includes an annular skin guide 2702 disposed axially above (that is, in the direction labeled UP in FIGS. 28, 31-33 and 36) the disk knife blade 2300 to direct a cut or excised section of skin tissue EST (FIGS. 36 and 37) axially upwardly and away from the disk knife blade 2300 as the disk debridement tool 2000 is moved along a section of skin tissue ST to be debrided or excised. A schematic depiction of a section of skin tissue ST being excised by the disk debridement tool 200 is shown in FIGS. 36 and 37. The head assembly 2200 additionally includes a depth gauge assembly 2600 that allows the operator to accurately set a depth of cut DOC of the excised skin tissue EST, as cut by the disk debridement tool 2000. The depth gauge assembly 2600 of the disk debridement tool 2000 advantageously facilitates obtaining excised skin tissue sections EST that are of a uniform in depth and allows for easy adjustment of the depth of cut DOC, as described with respect to the depth gauge assembly 600 of the power operated dermatome 100. That is, using the disk debridement tool 2000, the ability of an operator to obtain an excised skin tissue section of a desired, uniform depth is less dependent upon operator skill than with prior dermatomes.

Moreover, the skin guide assembly 2700, by directing the excised skin tissue section EST upwardly and away from the disk knife blade 2300, advantageously facilitates use of the disk debridement tool by a single operator, without an assistant providing counter-traction in a skin grafting region GR (FIG. 36). Typically, in operating the disk debridement tool 2000, the operator will use one hand to manipulate the disk debridement tool and the other hand, as necessary, to grasp and pull excised skin tissue EST, which is directly upwardly by the skin guide assembly 2700, up and away from the disk knife blade 2300 and the skin grafting region GR.

Disk Rotary Knife Blade Assembly 2301

As can best be seen in FIGS. 26, 27, 30, and 32-36, the disk rotary knife blade assembly 2301 includes the disk knife blade 2300 and a blade retainer 2400 that releasably secures the disk knife blade 2300 to an output shaft 2514 of a gearbox 2512 of the drive assembly 2500. The disk knife blade 2300 of the disk debridement tool 2000 includes a central body section 2302 and a blade section 2304 extending radially outwardly from the central body section 2302. The disk knife blade 2300 includes an outer wall 2350 that is part of the blade section 2304. The disk knife blade 2300 includes a generally planar upper surface 2306 and an axially spaced apart generally planar lower surface 2308. The upper surface 2306 of the disk knife blade 2300 includes an upper surface region 2306a in the central body section 2302 and an upper surface region 2306b in the blade section 2304. The lower surface 2308 of the disk knife blade 2300 includes a lower surface region 2308a in the central body section 2302 and a lower surface region 2308b in the blade section 2304.

The outer wall 2350 of the disk knife blade 2300 defines a generally frustoconical, tapered cutting surface 2352 that terminates at the cutting edge 2360 adjacent the lower surface region 2308b of the blade section 2304. Specifically, the cutting edge 2360 is defined at the outer peripheral edge 2362 of the disk knife blade 2300 at the intersection of the lower surface region 2308b of the blade section 2304 and the outer wall 2350. The cutting edge 2360 of the disk knife blade 2300 defines a cutting plane CP (FIG. 32) of the knife blade 2300, which is substantially orthogonal to the blade axis of rotation R.

Figure 30:
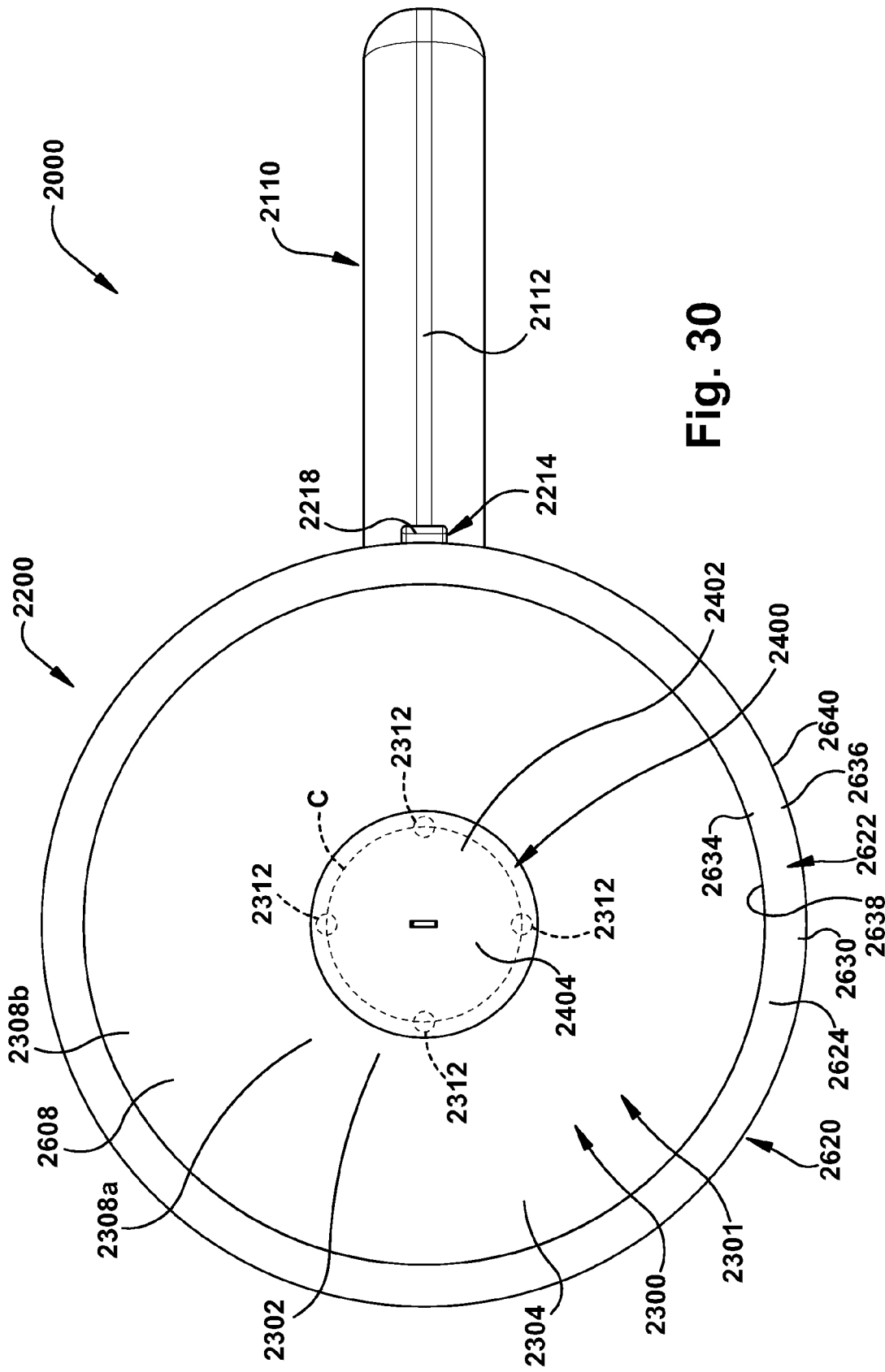
FIG. 30 is a schematic bottom plan view of the power operated debridement tool of FIG. 25.

The disk knife blade 2300 further includes a center opening 2310 (FIGS. 32 and 34) in the central body section 2302 to receive a connector 2406 of the blade retainer 2400. The central body section 2302 of the disk knife blade 2300 also includes a plurality of openings 2312 spaced radially outward from the center opening 2310, the plurality of openings 2312 being spaced uniformly apart on a common circumference C (FIG. 30). In one exemplary embodiment, the number of openings 2312 is four openings spaced uniformly at 90° apart.

While in the exemplary embodiment of the disk debridement tool 2000 depicted in FIGS. 25-30, the lower surface regions 2308b, 2306b of the blade section 2304 and the central body section 2302 are coplanar with the blade cutting plane CP, in other contemplated exemplary embodiments, the central body section 2302 may be axially offset above (in the direction labeled UP) the blade section 2304 to such that the lower surface region 2306b of the central body section 2302 is axially offset from and above the lower surface region 2308b of the blade section 2304. Such an offset of the body section lower surface region 2306b provides for relief of the central body section 2302 from an upper surface SST of the skin tissue ST in the grafting region GR during a procedure thereby reducing an area of contact between the bottom surface 2308 of the disk knife blade 2300 and/or the blade retainer 2400 and the upper surface SST of the skin tissue ST during use of the disk debridement tool 2000.

The disk knife blade 2300 is releasably affixed to and rotates with the gearbox output shaft 2514 by the blade retainer 2400 (FIGS. 30, 33 and 34) of the disk blade assembly 2301. In one exemplary embodiment, the blade retainer 2400 of the disk blade assembly 2301 comprises a blade locking screw 2402. The blade locking screw 2402 includes a generally planar body section 2404 and a connector 2406 extending upwardly from the planar body section 2404. The connector 2406 defines external threads 2308. The connector 2404 passes through the central opening 2310 of the disk knife blade 2300 and threads into a threaded recess 2518 in a lower end 2516 of the gearbox output shaft 2514. When the connector 2404 of the blade locking screw 2402 threads into the gearbox output shaft 2514, the planar body section 2404 of the blade locking screw 2402 bears against the lower surface region 2308a of the central body section 2302 of the disk knife blade 2300 to sandwich and secure the disk knife blade 2300 between a bottom wall 2760 of the skin guide hub 2750 of the skin guide assembly 2700 and the planar body section 2404 of the blade locking screw 2402. A plurality of axial projections 2762 extending from the bottom wall 2760 of the skin guide hub 2750 extend into the plurality of mating openings 2312 in the body section 2302 of disk knife blade 2300 to accurately locate the blade 2300 and insure that the blade 2300 and the skin guide assembly 2700 rotate in unison.

It should be recognized that the skin guide assembly 2700 and the disk knife blade 2300 may be fabricated as separate components, as is shown in the depicted exemplary embodiment of the disk debridement tool 2000. Alternately, the skin guide assembly 2700 and disk knife blade 2300 may be fabricated as an integral single component. Further, while in the depicted exemplary embodiment of the disk debridement tool 2000, a mechanical interconnection between the axial projections 2762 of the bottom wall 2760 of the skin guide hub 2750 extending into the plurality of mating openings 2312 in the body section 2302 of disk knife blade 2300 result in the skin guide assembly 2700 rotating with the disk knife blade 2300, it should be understood that in an alternate exemplary embodiment, the skin guide assembly 2700 may be configured to be stationary (e.g., affixed to an end plate 2210 of the frame body 2202 or to the frame body 2202) and thereby not rotate with the disk knife blade 2300. Each of these options, among others that would be understood by one of skill in the art, should be understood to be contemplated by the present disclosure.

Frame Body 2202

As is best seen in FIGS. 25-28 and 31-33, the frame body 2202 of the head assembly 2200 is generally cylindrical in shape and defines an axially extending opening or throughbore 2204 that extends along the axis of rotation R of the disk knife blade 2300. The throughbore 2204 of the frame body 2202 receives and supports at least a portion of the drive assembly 2500 of the disk debridement tool 2000. An upper end 2206 of the frame body 2202 is overlied and sealed by a top cover 2220, while a lower end 2208 of the frame body 2202 is overlied and sealed by the end plate 2210. The end plate 2210, in addition to sealing the lower end 2208 of the frame body 2202, also supports a sealing assembly 2212 (FIG. 34). The sealing assembly 2212 provides a seal between the rotating output shaft 2514 of a drive assembly gearbox 2512 and the stationary end plate 2210 affixed to the frame body 2202.

Drive Assembly 2500

Figure 31:
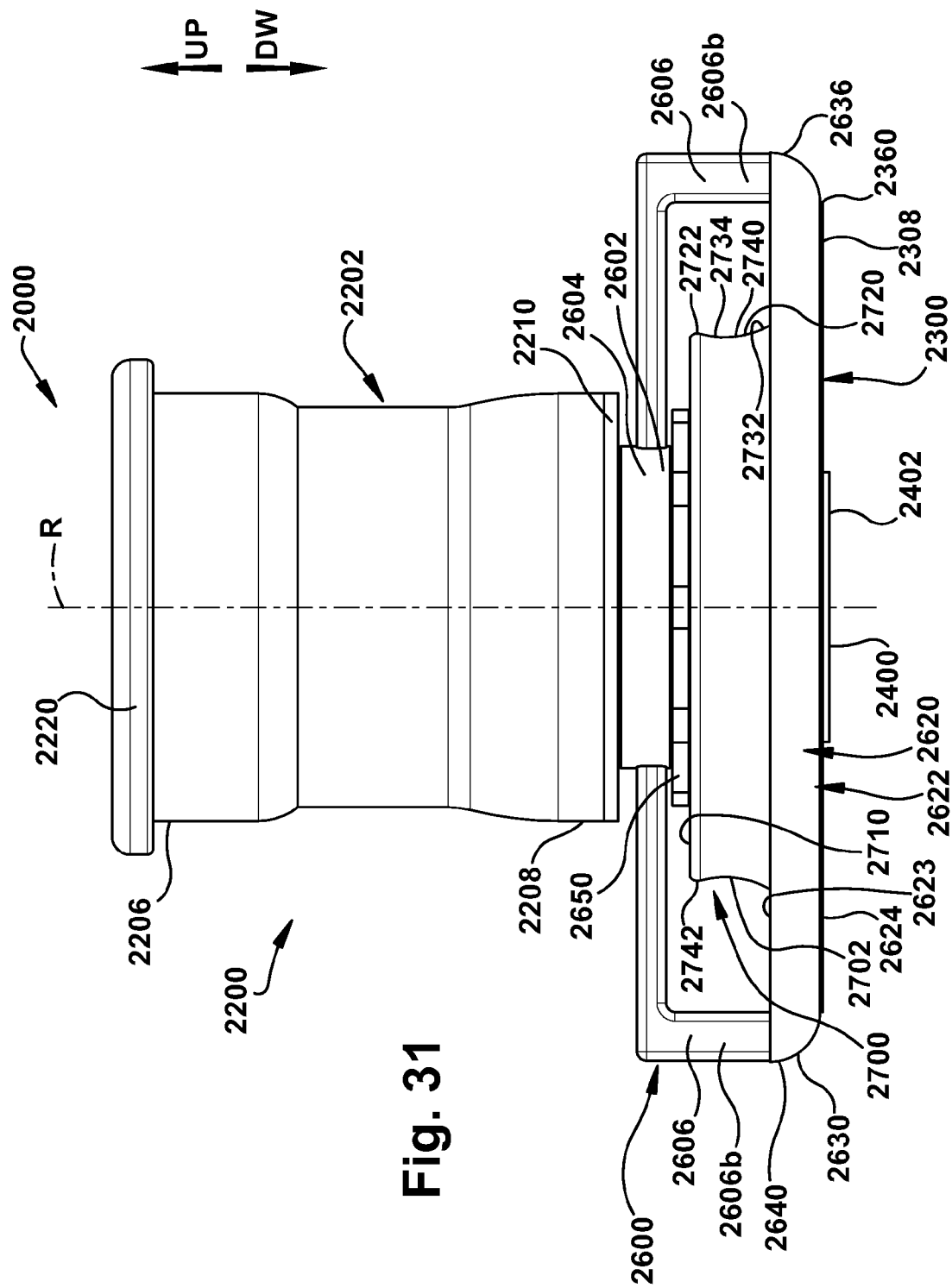
FIG. 31 is a schematic front elevation view of the power operated debridement tool of FIG. 26.
Figure 32:
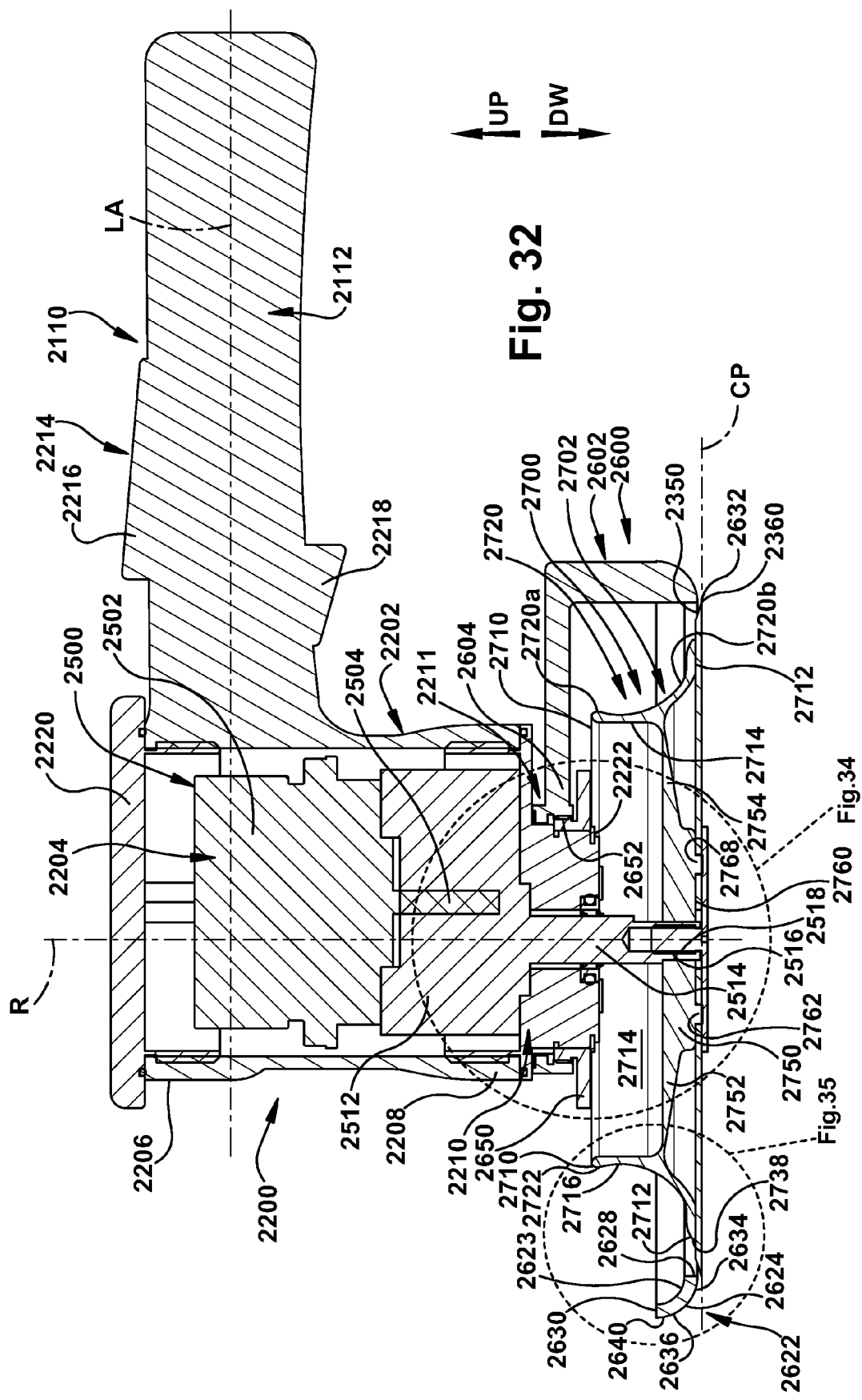
FIG. 32 is a schematic section view of the power operated debridement tool of FIG. 26 as seen from a plane indicated by the line 32-32 in FIG. 29.
Figure 33:
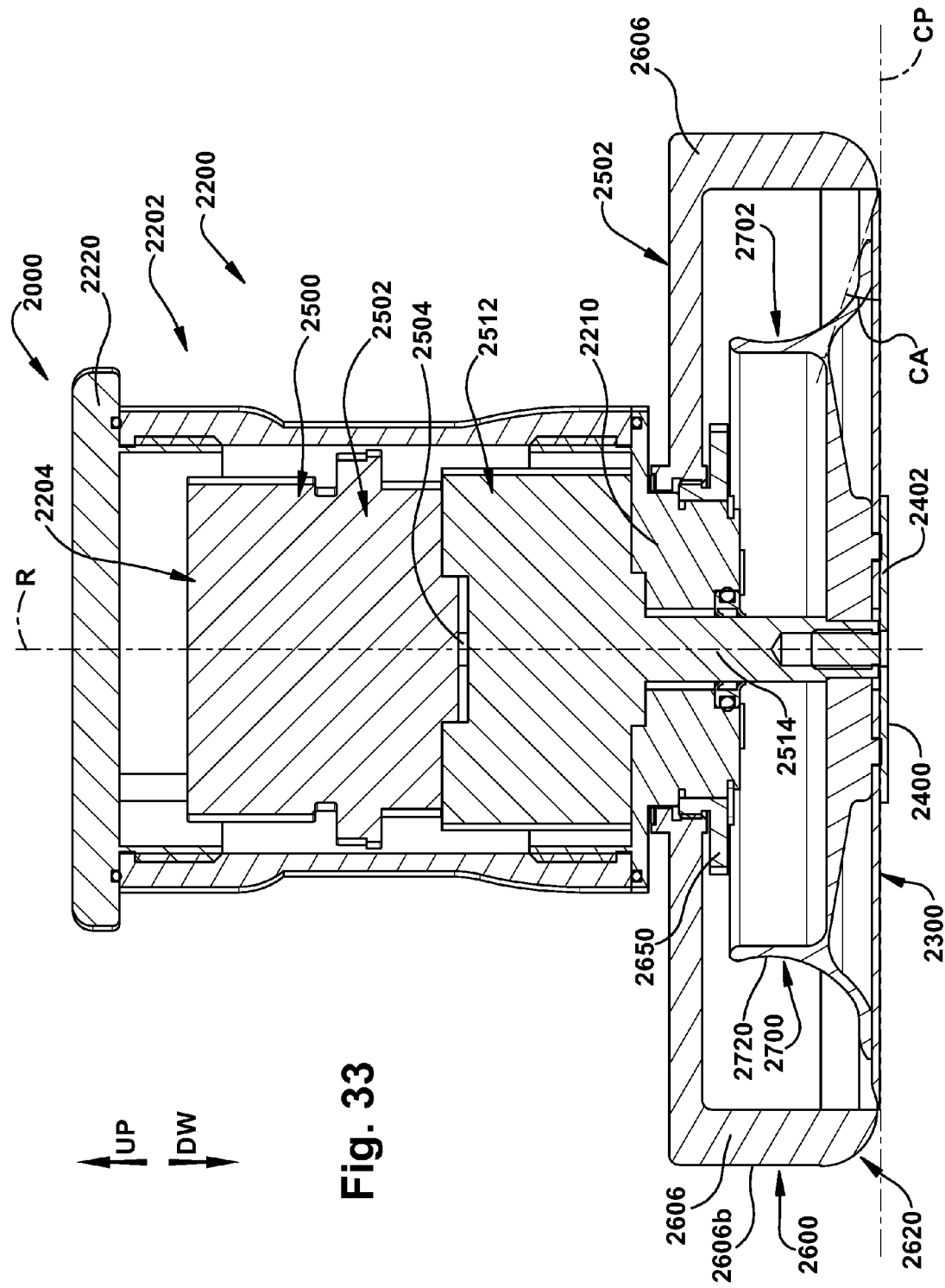
FIG. 33 is a schematic section view of the power operated debridement tool of FIG. 26 as seen from a plane indicated by the line 33-33 in FIG. 29.
Figure 34:
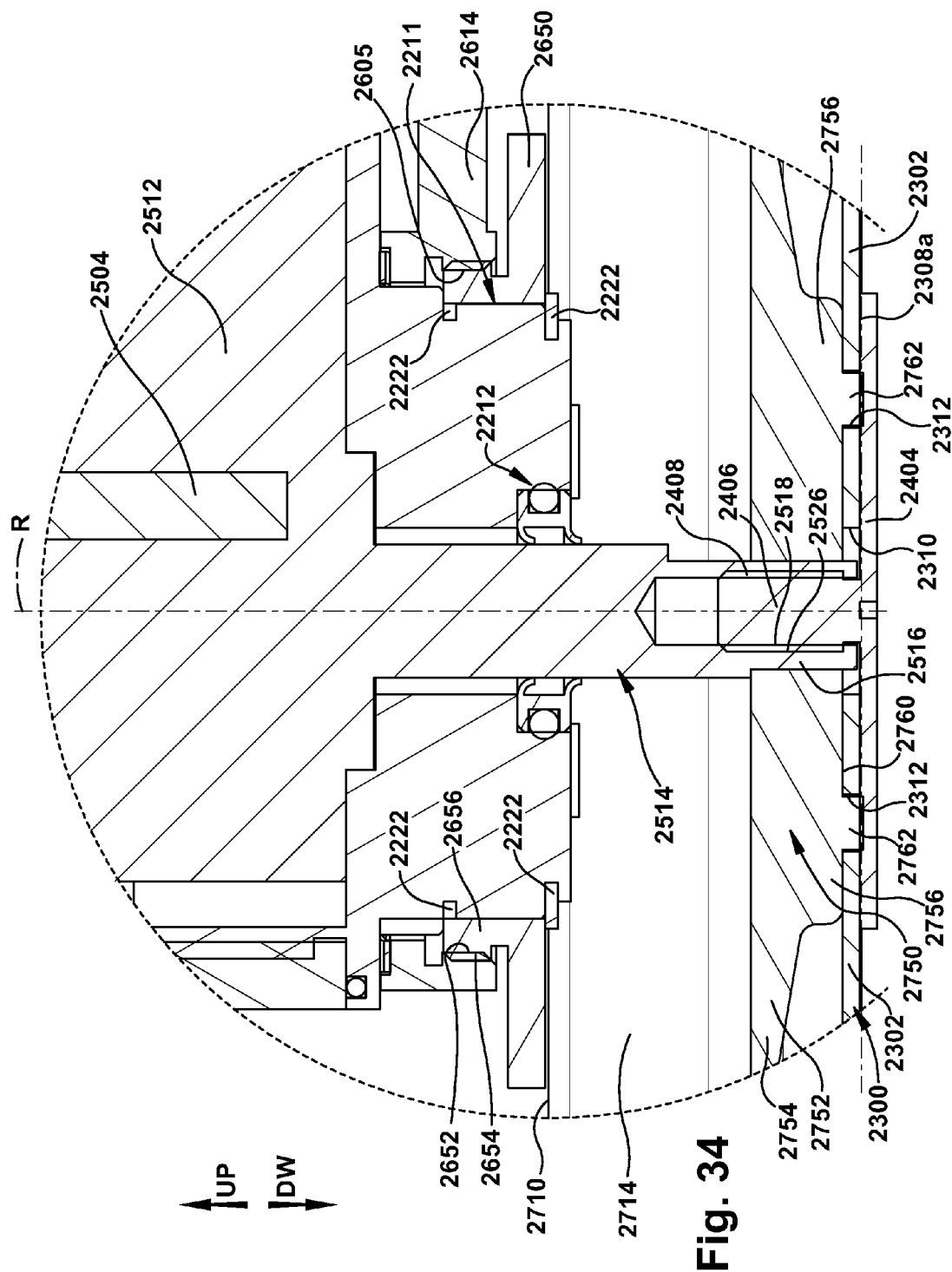
FIG. 34 is a schematic enlarged section view of a portion of the head assembly shown in FIG. 32 that is within a dashed circle labeled FIG. 34 in FIG. 32.

In one exemplary embodiment, as schematically shown in FIGS. 32 and 33, the drive assembly 2500 of the disk debridement tool 2000 includes a drive motor 2502 and the gear reduction unit or gearbox 2512 disposed within the throughbore 2204 of the frame body or housing 2202. The drive motor 2502, in one exemplary embodiment may be a DC drive motor, as shown in FIGS. 30 and 31. Alternately, the drive assembly 2500 may comprise an air motor and planetary gear reduction unit, as described with respect to the power operated dermatome 100. Further, the drive assembly 2500 may comprise an external drive motor coupled through a flexible shaft drive transmission (not shown) extending through the throughbore 2204 in the frame housing 2202 to provide motive power to rotate the disk knife blade 2300 with respect to the frame housing 2202 about its axis of rotation R.

The gearbox 2412 receives a rotating output shaft 2504 of the DC drive motor 2502 and through an appropriate gearing arrangement, such a planetary gearing arrangement (not shown), provides a desired rotational speed to the disk knife blade 2300 (on the order of 500-1,500 RPM). The gearbox 2512 includes the output shaft 2514. The output shaft 2514 includes the threaded recess 2518 at the lower end 2516 of the output shaft 2514. The gearbox output shaft 2514 rotates about and indeed defines the disk knife blade axis of rotation R. A suitable DC electric motor, for example, the Maxon Model No. EC22 386680 and an associated gear reduction unit or gearbox, for example, the Maxon Model No. GPM 22M 305130, may be obtained from Maxon Motor AG, Sachsein, Switzerland (www.maxonmotor.com).

Handle Assembly 2110

As seen in FIGS. 25-30, the handle assembly 2110 of the disk debridement tool 2000 includes an elongated handle 2112 that extends from the frame body 2202 along a longitudinal axis LA. The longitudinal axis L is generally orthogonal to and intersects the axis of rotation R of the disk knife blade 2300. The handle 2112 is sized and contoured for ease of gripping and manipulation by the operator of the disk debridement tool 2000. The handle assembly 2110 may include an actuation trigger 2214 to actuate the drive assembly 2500. In one exemplary embodiment, the actuation trigger 2214 may be a two-part trigger that includes both an upper trigger 2216 and a lower trigger 2218, both of which must be depressed by the operator to actuate the drive assembly 2500. Alternatively, an actuation lever (not shown) pivotally mounted to the handle 2112, of the type described with respect to the power operated dermatome 100, may be provided to actuate the disk knife blade 2300. Yet another alternative for actuation of the disk knife blade 2300 would be a foot pedal valve or actuation switch positioned at the feet of the operator that would be tripped to actuate the drive assembly 2500. As shown in FIGS. 25-30, the handle assembly 2110 may be fabricated as integral with the frame body 2202 or, alternatively, may fabricated as a separate component and affixed to the frame housing 2202 by suitable means.

Annular Skin Guide Assembly 2700

Figure 35:
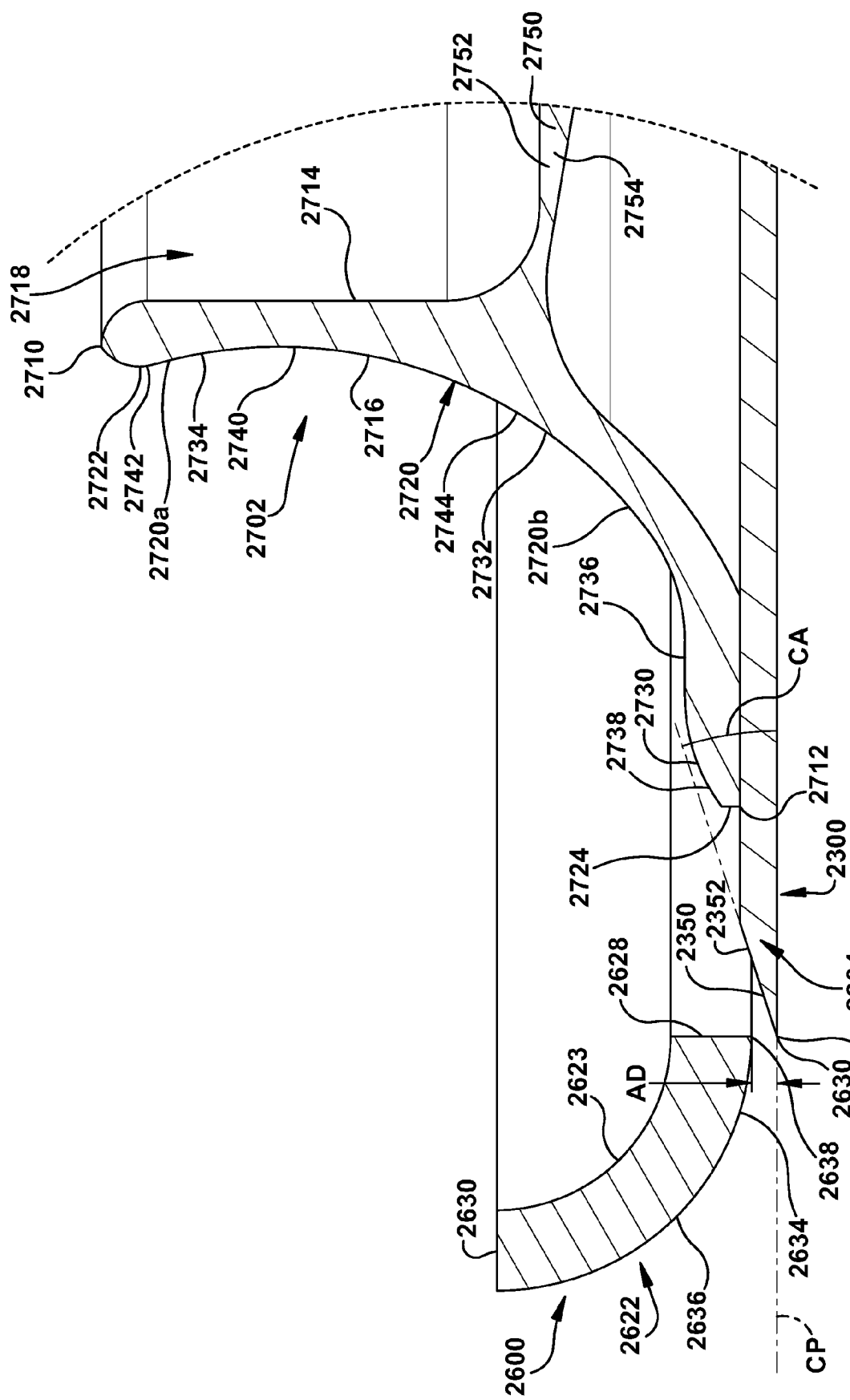
FIG. 35 is a schematic enlarged section view of a portion of the head assembly shown in FIG. 32 that is within a dashed circle labeled FIG. 35 in FIG. 32.

As is best seen in FIGS. 33, 35 and 36, the head assembly 2200 of the disk debridement tool 2000 includes the annular skin guide assembly 2700 including the annular skin guide 2702 and a skin guide hub 2750, which supports the skin guide 2702 and affixes the skin guide assembly 2700 to the disk knife blade 2300. In the power operated dermatome 100, because the cutting edge 360 of the rotary knife blade 300 was defined at an inner wall 354 of the blade section 304, an excised section of skin tissue EST passed through the interior region 301 of the rotary knife blade 300. In contrast, in the power operated disk debridement tool 2000 of the present invention, the cutting edge 2360 of the disk knife blade 2300 is defined at the radial outer periphery 2362 of the disk knife blade 2300. Accordingly, when used to excise a layer of skin tissue ST, an excised section of skin tissue EST severed by the cutting edge 2360 of the disk knife blade 2300 passes over the upper surface 2306b of the blade section 2304 of the disk knife blade 2300.

To facilitate one-handed operation of the disk debridement tool 2000, the excised section of skin tissue EST is guided along a path of travel PTEST (FIGS. 36 and 37) in a generally upward direction UP away from the upper surface 2306b of the blade section 2304 of the disk knife blade 2300 by the annular skin guide 2702. The annular skin guide 2702 is disposed above the upper surface 2306b of the blade section 2304 and, being annular, defines a 360° annulus above the blade section 2304. Thus, advantageously, no matter what the direction of movement of disk debridement tool 2000 along the skin tissue ST to be excised, a longitudinal central axis of the excised skin tissue section EST will move generally radially inwardly along the upper surface 2306b of the blade section 2304 toward the axis of rotation R of the disk knife blade 2300. The excised skin tissue section EST therefore will contact the annular skin guide 2702 and be directed upwardly along a generally arcuate path by the skin guide 2700 away from the blade section upper surface 2306b. Thus, while the operator operates and manipulates the disk debridement tool 2000 with one hand, in the case of an excised skin tissue section EST having a significant longitudinal length, the operator may utilize his or her other hand to pull upwardly on the excised skin tissue section EST to prevent a portion of the excised skin tissue section EST from folding or flopping back onto the grafting region GR thereby interfering with or impeding the cutting procedure or otherwise impairing the ability of the operator to see the grafting region GR in the area where the disk knife blade 2300 is cutting the skin tissue ST.

The annular skin guide 2702 includes an upper end 2710 and an axially spaced apart lower end 2712, and an inner wall 2714 and a radially spaced outer wall 2716. The lower end 2712 of the skin guide 2702 abuts the upper surface region 2306b of the blade section 2304 of the disk knife blade 2300. Viewed in an axial direction, the lower end 2712 of the skin guide 2702 is adjacent or near, but is radially offset, from the cutting edge 2360 of the disk knife blade 2300. The inner wall 2714 of the annular skin guide 2700 defines a central open region 2718.

The outer wall 2716 of the annular skin guide 2702 defines a skin contact surface 2720. When viewed in section along the blade axis of rotation R, the skin contact surface 2720 extends axially between a first, upper outer edge 2722 adjacent the upper end 2710 of the skin guide 2702 and a second, lower outer edge 2724 adjacent the lower end 2712 of the skin guide 2702. The skin contact surface 2720 of the skin guide 2702 includes a leading end portion 2730, commencing at the second, lower outer edge 2724 adjacent the blade section upper surface 2306b, an arcuate central extent 2732 axially above and radially inwardly of the leading end portion 2730, and a trailing end portion 2734 axially above the central extent 2732 and terminating at the first, upper outer edge 2722 adjacent the lower end 2712 of the skin guide 2720. The leading end portion 2730 including a first region 2736 closest to the cutting edge 2360 of the disk knife blade 2300. The first region 2736 is substantially parallel to the cutting plane CP of the disk knife blade 2300 and includes a tapered terminal end or terminus 2738 that is angled in a downward direction toward the upper surface region 2306b of the blade section 2304 of the disk knife blade 2300 to provide for a smooth surface for the excised skin tissue section EST to move along as the section EST transitions or moves along the path of travel PTEST radially inwardly from the upper surface region 2306b of the blade section 2304 to the skin contact surface 2720 of the skin guide 2702. The tapered terminus 2738 of the first region 2736 of the leading end portion 2730 defines the second, lower outer edge 2724 of the skin contact surface 2720.

In one exemplary embodiment, the arcuate central extent 2732 of the skin contact surface 2720, when viewed in section along the blade axis of rotation R, defines an arc of substantially 90° and includes a second region 2740 that is substantially parallel to the axis of rotation R of the disk knife blade 2300. The trailing end portion 2734 of the skin contact surface 2720, when viewed in section along the blade axis of rotation R, includes a third region 2742 that curves away from the axis of rotation R of the disk knife blade 2300. A terminus of the trailing end portion 2734 defines the first, upper outer edge 2722 of the skin contact surface 2720. Thus, when considering the skin contact surface 2720 of the skin guide 2700 in its entirety, in one exemplary embodiment, the path of travel PTEST of the excised skin tissue section EST as it moves along the skin contact surface 2730 is arcuate, moving in a direction that is axially upwardly with respect to the cutting plane CP of the disk knife blade 2300 and generally radially inwardly toward the blade axis of rotation R (except in the third region 2742 where the excised skin tissue section EST is directed slightly radially outwardly).

In one exemplary embodiment, the skin contact outer surface 2720 is generally arcuate in shape and, when viewed from the axis of rotation R of the disk knife blade 2300, is generally concave with respect to the axis of rotation R. That is, if the skin contact outer surface 2720 is viewed in longitudinal section, the outer surface 2720 bows inwardly toward the axis of rotation R. Stated another way, if a line segment LS were drawn between the first, upper outer edge 2722 and the second, lower outer surface 2724 of the skin contact surface 2720 of the skin guide 2702, the skin contact surface 2720 is recessed radially inwardly with respect to the line segment LS. Stated another way, the skin contact surface 2720 is concave with respect to the line segment LS in a direction DI (FIG. 36) that is generally toward the disk knife blade axis of rotation R. The direction DI is taken from a midpoint MLS of the line segment LS to an approximate midpoint 2744 of the skin contact surface 2720 between the first, upper outer edge 2722 and the second, lower outer edge 2724. The skin contact surface 2720 of the skin guide 2702 is axially below the first upper outer edge 2722 and is radially inward of the second, lower outer edge 2724.

The arcuate skin contact surface 2720, when viewed in longitudinal cross section along the disk knife blade axis of rotation R, circumscribes an arc of slightly in excess of 90° and has upper and lower end portions 2720a, 2720b (FIG. 35) that curve away from the axis of rotation R. Thus, the skin contact surface 2720 is concave with respect to the disk knife blade axis of rotation R. It should be understood, however, that, in other exemplary embodiments, an arc defined by the skin contact surface may be 90°, less than 90° or more than 90°, depending on the characteristics of the tissue being excised or cut, including, the desired depth of cut DOC, the nature of the tissue, the size and rotational speed of the disk knife blade 2300, among other factors.

By way of example and without limitation, an outer diameter of the disk knife blade 2300 of the disk debridement tool 2000 may be in a range of 1-6 in. The second, lower outer edge 2724 of the skin contact surface 2720 is offset radially inwardly in a range of approximately 0.125-1.0 in. from the cutting edge 2360 of the disk knife blade 2300. In one exemplary embodiment, wherein the outer diameter of the disk knife blade 2300 is approximately 4.5 in., an axial height of between the first, upper outer edge 2722 and the second, lower outer edge 2724 of the skin contact surface 2720 of the skin guide 2702 is approximately 0.67 in. and the radial offset between the second, lower outer edge and the first, upper outer edge 2722 of the skin contact surface 2720 is approximately 0.50 in.

As is best seen in FIGS. 31-33, the skin guide assembly 2700 includes the annular skin guide 2702 and the skin guide hub 2750. The skin guide 2702 is located and supported above the upper surface 2306 of the disk knife blade 2300 by the skin guide hub 2750. In one exemplary embodiment, the annular skin guide 2700 may be integral, i.e., one-piece construction, with the skin guide hub 2750. The skin guide hub 2750 is disposed in the central open region 2718 defined by the annular skin guide 2700. An upper portion 2752 of the skin guide hub 2750 includes a radially extending rib 2754 which extends between the inner wall 2714 of the skin guide 2702 and a body or base 2756 of the skin guide hub 2750 to affix the hub 2750 and the skin guide 2702 to rotate in unison. As noted previous, the bottom wall 2760 defined by the base 2756 of the skin guide hub 2750 includes the plurality of projections 2762. The projections 2762 extend axially downwardly from the bottom wall 2760 and fit into the plurality of mating openings 2312 in the body section 2302 of disk knife blade 2300 to accurately locate the blade 2300 and insure that the blade 2300 and the skin guide assembly 2700 rotate in unison. By virtue of the securement of the skin guide assembly 2700 to the disk knife blade 2300, the skin guide assembly 2700 rotates about the blade axis of rotation R.

Depth Gauge Assembly 2600

As can be seen in FIGS. 31-34, the depth of cut DOC of the disk debridement tool 2000 is determined by the depth gauge assembly 2600. Although the configuration and axial adjustment of the depth gauge assembly 2600 is similar in certain respects to the depth gauge assembly 600 of the power operated dermatome 100, a depth gauge 2620 of the depth gauge assembly 2600 is positioned radially outwardly of the cutting edge 2360 of the disk knife blade 2300 and axially above the cutting plane CP of the disk knife blade 2300. The depth gauge 2620 must be positioned outwardly of the cutting edge 2360 of the disk knife blade 2300 because the cutting edge 2360 is formed on the outer peripheral edge 2362 of the blade section 2304 of the disk knife blade 2300.

The depth gauge assembly 2600 includes the depth gauge 2620 comprising an annular depth gauge plate 2622 and a depth gauge support 2602 that supports the depth gauge 2620. In one exemplary embodiment, the annular depth gauge plate 2622 extends around a complete 360° circumference of the disk knife blade 2300 and is spaced radially outwardly from the peripheral edge 2362 defining the cutting edge 2360 by a distance of approximately 0.25 in.

The depth gauge plate includes an upper surface 2623 and a lower surface 2624 and an inner wall 2628 and an outer wall 2630. An axial distance AD between the lower surface 2624 of the depth gauge plate 2622 and the cutting plane CP of the disk knife blade 2300 determines the depth of cut DOC of the disk debridement tool 2000 and, thus, a depth DEST of the excised skin tissue EST, as explained previously. In one exemplary embodiment, a range of depth of cut DOC for the disk debridement tool 2000 is between 0.00-0.50 in. Of course, a depth of cut DOC of zero would typically not be of value for a medical procedure because little or no skin tissue ST would be excised by the disk debridement tool 2000, that is, the axial distance AD (FIGS. 35-37) between the lower surface 2624 of the depth gauge plate 2622 and the cutting plane CP of the disk knife blade 2300 would be essentially 0.000 in. At the intersection of the lower surface 2624 and the inner wall 2628 is a lower, inner edge region 2632. The skin tissue ST being excised passes between the lower, inner edge region 2632 of the depth gauge plate 2622 and the cutting edge 2360 of the disk knife blade 2300 where it is severed by the cutting edge 2360.

As can best be seen in FIGS. 36 and 37, the excised skin tissue EST moves along the tapered cutting surface 2352 of the outer wall 2350 of the disk knife blade. The excised skin tissue EST then moves along the upper surface region 2306b of the blade section 2304 of the disk knife blade 2300 until it encounters or contacts the tapered terminus 2738 of the first region 2736 of the leading end portion 2730 of the skin contact surface 2720 of the annular skin guide 2702. The excised skin tissue EST is then directed axially upwardly and radially inwardly by the leading end portion 2730 of the skin contact surface 2720. The excised skin tissue EST is then directed axially upwardly and radially inwardly by the central extent 2732 of the skin contact surface 2720. Finally, the excised skin tissue EST is then directed axially upwardly above the upper end 2710 of the annular skin guide 2702 by the trailing end portion 2734 of the skin contact surface 2720 and, at the same time, radially away from blade axis of rotation R by the third region 2742 of the trailing end portion 2734.

The lower surface 2624 of the depth gauge plate 2622 includes an inner portion 2634 and a radially outer portion 2636. The inner portion 2634 of the lower surface 2624 of the depth gauge plate 2622 includes a region 2638 closest to the cutting edge 2360 of the disk knife blade 2300 that is substantially parallel to the cutting plane CP of the disk knife blade 2300. The lower surface 2624 of the depth gauge plate 2622 is convex in shape with respect to the cutting plane CP of the disk knife blade 2300. The outer portion 2636 of the lower surface 2624 of the depth gauge plate 2622 includes a region 2640 that is substantially parallel to the axis of rotation R of the disk knife blade 2300.

The depth gauge support 2602 includes a central body or disk 2604 and a plurality of radially spaced apart right-angled arms 2606 that extend between the central disk 2604 and the depth gauge plate 2622 to provide support and adequate stiffening to the depth gauge plate 2622 to minimize undesirable flexing of the depth gauge plate 2622 as the plate 2622 is urged against and moved along the upper layer or surface SST of the skin tissue ST to be excised during a grafting or debriding procedure. In one exemplary embodiment, the number of arms 2606 is three and the arms 2606 are spaced approximately 90° apart, with a center arm 2606a of the three arms 2606 being aligned with the elongated handle 2112 of the handle assembly 2110. In this way, an uninterrupted arcuate region AR of approximately 180° is provided for cutting of skin tissue ST between the two outlying arms 2606b.

The central disk 2604 of the depth gauge support 2602 is coupled to the end plate 2210 of the frame body 2202 and is movable axially with respect to the frame body 2202. A rotatable depth adjustment collar 2650 (FIG. 31) is coupled to a necked down portion 2211 of the end plate 2210. A pair of retaining rings 2222 (FIG. 33) prevent the depth adjustment collar 2650 from axial movement along the necked down portion 2211 of the end plate 2210, while permitting rotation of the depth adjustment collar 2650 with respect to the frame body 2202 about the disk knife blade axis of rotation R. There is a threaded interconnection 2652 between a threaded outer surface 2654 of an upper portion 2656 of the depth adjustment collar 2650 and a threaded inner surface 2605 of the central disk 2604 of the depth gauge support 2602. Thus, as the depth adjustment collar 2650 is rotated in one direction, the depth gauge support 2602 and the affixed depth gauge plate 2622 move axially upwardly, that is, axially up away from the cutting edge 2360, increasing the depth of cut DOC of the disk debridement tool 2000. Conversely, as the depth adjustment collar 2650 is rotated in the opposite direction, the depth gauge support 2602 and the affixed depth gauge plate 2622 move axially downwardly, that is, axially down toward the cutting edge 2360, decreasing the depth of cut DOC of the tool 2000.

Operation of Disk Debridement Tool 2000

As is schematically depicted in FIGS. 36 and 37, when the disk debridement tool 2000 is operated to cut or excise a section of skin tissue ST in a grafting region GR, an initial or starting end SEEST of the excised skin tissue EST passes between the lower, inner edge region 2632 of the depth gauge plate 2622 and the cutting edge 2360 of the disk knife blade 2300 where it is severed by the cutting edge 2360. As is schematically illustrated in FIG. 36, the excised skin tissue EST follows a path of travel PTEST and moves along the tapered cutting surface 2352 of the outer wall 2350 of the disk knife blade 2300 and then along the upper surface region 2306*b* of the blade section 2304 of the disk knife blade 2300 in a direction generally toward the blade axis of rotation R.

As the excised skin tissue EST continues to move along the upper surface region 2306*b* of the blade section 2304 of the disk knife blade 2300, the starting end SEEST of the excised skin tissue section EST contacts the skin contact surface 2720 of the annular skin guide 2702 at the tapered terminus 2738 of the first region 2736 of the leading end portion 2730. The excised skin tissue EST, lead by the starting end SEEST, follows the path of travel PTEST, along the arcuate skin contract surface 2720 from the leading end portion 2730, to the central extent 2732 and to the trailing end portion 2732.

Thus, in the region of the skin contact surface 2720, the excised skin tissue follows an arcuate path of travel that is part of the overall path of travel PTEST of the excised skin tissue EST. Ultimately, the starting end SEEST of the excised skin tissue EST exits upwardly from the skin contact surface 2720 and at an angle that this slight away from the blade axis of rotation R. As noted previously, the operator of the disk debridement tool 2000, in the case of an excised skin tissue section EST having a lengthy longitudinal extent, the operator may grasp the starting end SEEST of the excised skin tissue section EST to keep the start end SEEST of the excised skin tissue section EST from falling or flopping onto the grafting region GR when the starting end SEEST leaves the trailing end portion 2732 of the skin contact surface 2720.

As used herein, terms of orientation and/or direction such as front, rear, forward, rearward, distal, proximal, distally, proximally, upper, lower, inward, outward, inwardly, outwardly, horizontal, horizontally, vertical, vertically, axial, radial, longitudinal, axially, radially, longitudinally, etc., are provided for convenience purposes and relate generally to the orientation shown in the Figures and/or discussed in the Detailed Description. Such orientation/direction terms are not intended to limit the scope of the present disclosure, this application, and/or the invention or inventions described therein, and/or any of the claims appended hereto. Further, as used herein, the terms comprise, comprises, and comprising are taken to specify the presence of stated features, elements, integers, steps or components, but do not preclude the presence or addition of one or more other features, elements, integers, steps or components.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A head assembly for a power operated debridement tool, the head assembly comprising:
   a frame body;
   a disk knife blade coupled to the frame body and rotated about an axis of rotation, the disk knife blade including a cutting edge on an outer peripheral edge of the disk knife blade defining a cutting plane of the disk knife blade that is orthogonal to the axis of rotation; and
   an annular skin guide including an upper end, an axially spaced apart lower end adjacent the disk knife blade, and an outer wall defining a skin contact surface extending between the upper and lower ends of the annular skin guide, the skin contact surface positioned above the cutting plane of the disk knife blade and radially inwardly of the disk knife blade cutting edge to receive and direct a layer of skin tissue cut by the disk knife blade upwardly away from the blade cutting edge, the skin contact surface being recessed radially inwardly in a direction proceeding toward the disk knife blade axis of rotation with respect to a line segment extending between a first outer edge of the skin contact surface adjacent the upper end of the annular skin guide and a second outer edge of the skin contact surface adjacent the lower end of the annular skin guide.

2. The head assembly of claim 1 wherein the skin contact surface of the annular skin guide is arcuate with respect to a longitudinal cross section taken along the disk knife blade axis of rotation.

3. The head assembly of claim 2 wherein the skin contact surface of the annular skin guide includes a leading end portion, closest to the cutting edge of the disk knife blade and adjacent the lower end of the annular skin guide, a central extent, and a trailing end portion, furthest from the cutting edge of the disk knife blade and adjacent the upper end of the annular skin guide, the leading end portion including a first region substantially parallel to the cutting plane of the disk knife blade.

4. The head assembly of claim 3 wherein the central extent of the skin contact surface defines an arc of substantially 90° and includes a second region that is substantially parallel to the axis of rotation of the disk knife blade.

5. The head assembly of claim 3 wherein the trailing end portion includes a third region that curves away from the axis of rotation of the disk knife blade.

6. The head assembly of claim 1 wherein the skin contact surface of the annular skin guide is concave in shape with respect to the disk knife blade axis of rotation.

7. The head assembly of claim 1 wherein the annular skin guide is affixed to and rotates with the disk knife blade.

8. The head assembly of claim 3 wherein a terminus of the leading end portion of the annular skin guide is radially offset from the cutting edge of the disk blade a distance in a range of 0.125-1.0 in.

9. The head assembly of claim 1 further including an axially adjustable depth gauge assembly including a depth gauge support and a depth gauge plate, the depth gauge support attached to and extending from the frame body and the depth gauge plate supported by the depth gauge support for axial movement along the axis of rotation of the disk knife blade, the depth gauge plate positioned above the cutting plane of the disk knife blade and radially outwardly of the cutting edge of the disk knife blade.

10. The head assembly of claim 9 wherein the depth gauge plate of the depth gauge assembly includes a lower surface, an axial distance between the lower surface and the cutting plane of the disk knife blade defining a depth of cut of the debridement tool, the lower surface of the depth gauge plate including an inner portion and a radially outer portion, the inner portion including a region closest to the cutting edge of the disk knife blade that is substantially parallel to the cutting plane of the disk knife blade.

11. The head assembly of claim 10 wherein the lower surface of the depth gauge plate is convex in shape.

12. The head assembly of claim 10 wherein the outer portion of the lower surface of the depth gauge plate includes a region that is substantially parallel to the axis of rotation of the disk knife blade.

13. The head assembly of claim 1 wherein the disk knife blade includes a central body section and a radially outlying blade section, the blade section including the cutting edge of the disk knife blade.

14. The head assembly of claim 13 wherein the central body section of the disk knife blade is axially offset above the cutting plane of the disk knife blade.

15. A power operated debridement tool comprising:
a frame body;
a drive assembly supported by the frame body;
a disk knife blade coupled to the frame body and rotated by the drive assembly about an axis of rotation, the disk knife blade including a cutting edge on an outer peripheral edge of the disk knife blade defining a cutting plane of the disk knife blade that is orthogonal to the axis of rotation; and
an annular skin guide including an upper end, an axially spaced apart lower end adjacent the disk knife blade, and an outer wall defining a skin contact surface extending between the upper and lower ends of the annular skin guide, the skin contact surface positioned above the cutting plane of the disk knife blade and radially inwardly of the disk knife blade cutting edge to receive and direct a layer of skin tissue cut by the disk knife blade upwardly away from the blade cutting edge, the skin contact surface being recessed radially inwardly in a direction proceeding toward the disk knife blade axis of rotation with respect to a line segment extending between a first outer edge of the skin contact surface adjacent the upper end and a second outer edge of the skin contact surface adjacent the lower end of the annular skin guide.

16. The power operated debridement tool of claim 15 wherein the skin contact surface of the annular skin guide is arcuate in a longitudinal cross section taken along the disk knife blade axis of rotation.

17. The power operated debridement tool of claim 16 wherein the skin contact surface of the annular skin guide includes a leading end portion, closest to the cutting edge of the disk knife blade and adjacent the lower end of the annular skin guide, a central extent, and a trailing end portion, furthest from the cutting edge of the disk knife blade and adjacent the upper end of the annular skin guide, the leading end portion including a first region substantially parallel to the cutting plane of the disk knife blade.

18. The power operated debridement tool of claim 17 wherein the central extent of the skin contact surface defines an arc of substantially 90° and includes a second region that is substantially parallel to the axis of rotation of the disk knife blade.

19. The power operated debridement tool of claim 17 wherein the trailing end portion includes a third region that curves away from the axis of rotation of the disk knife blade.

20. The power operated debridement tool of claim 15 wherein the skin contact surface of the annular skin guide is concave in shape with respect to the disk knife blade axis of rotation.

21. The power operated debridement tool of claim 15 wherein the annular skin guide is affixed to and rotates with the disk knife blade.

22. The power operated debridement tool of claim 17 wherein a terminus of the leading end portion of the annular skin guide is radially offset from the cutting edge of the disk blade a distance in a range of 0.125-1.0 in.

23. The power operated debridement tool of claim 15 further including an axially adjustable depth gauge assembly including a depth gauge support and a depth gauge plate, the depth gauge support attached to and extending from the frame body and the depth gauge plate supported by the depth gauge support for axial movement along the axis of rotation of the disk knife blade, the depth gauge plate positioned above the cutting plane of the disk knife blade and radially outwardly of the cutting edge of the disk knife blade.

24. The power operated debridement tool of claim 23 wherein the depth gauge plate of the depth gauge assembly includes a lower surface, an axial distance between the lower surface and the cutting plane of the disk knife blade defining a depth of cut of the debridement tool, the lower surface of the depth gauge plate including an inner portion and a radially outer portion, the inner portion including a region closest to the cutting edge of the disk knife blade that is substantially parallel to the cutting plane of the disk knife blade.

25. The power operated debridement tool of claim 24 wherein the lower surface of the depth gauge plate is convex in shape.

26. The power operated debridement tool of claim 24 wherein the outer portion of the lower surface of the depth gauge plate includes a region that is substantially parallel to the axis of rotation of the disk knife blade.

27. The power operated debridement tool of claim 15 wherein the disk knife blade includes a central body section and a radially outlying blade section, the blade section including the cutting edge of the disk knife blade.

28. The power operated debridement tool of claim 27 wherein the central body section of the disk knife blade is axially offset above the cutting plane of the disk knife blade.

* * * * *